(12) United States Patent
Svendsen et al.

(10) Patent No.: US 9,115,346 B2
(45) Date of Patent: Aug. 25, 2015

(54) LIPOLYTIC ENZYMES

(75) Inventors: Allan Svendsen, Hørsholm (DK); Jesper Vind, Værløse (DK); Hans Peter Heldt-Hansen, Virum (DK); Luise Erlandsen, Copenhagen (DK)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 12/826,960

(22) Filed: Jun. 30, 2010

(65) Prior Publication Data

US 2011/0165655 A1 Jul. 7, 2011

Related U.S. Application Data

(63) Continuation of application No. 10/495,597, filed as application No. PCT/DK03/00028 on Jan. 16, 2003, now abandoned.

(60) Provisional application No. 60/353,557, filed on Feb. 4, 2002.

(30) Foreign Application Priority Data

Jan. 16, 2002  (DK) .................................. 2002 00074

(51) Int. Cl.
*C12N 9/00* (2006.01)
*A61K 38/43* (2006.01)
*C12N 9/20* (2006.01)

(52) U.S. Cl.
CPC ........... *C12N 9/20* (2013.01); *C12Y 301/01003* (2013.01)

(58) Field of Classification Search
None
See application file for complete search history.

(56) References Cited

U.S. PATENT DOCUMENTS

| | | | |
|---|---|---|---|
| 3,368,903 | A | 2/1968 | Johnson et al. |
| 4,567,046 | A | 1/1986 | Inoue et al. |
| 5,352,594 | A | 10/1994 | Poulouse |
| 5,821,102 | A | 10/1998 | Berka et al. |
| 5,892,013 | A | 4/1999 | Svendsen et al. |
| 6,140,094 | A | 10/2000 | Loffler et al. |
| 6,143,545 | A | 11/2000 | Clausen et al. |
| 6,265,197 | B1 | 7/2001 | Bisgard-Frantzen et al. |
| 7,312,062 | B2 | 12/2007 | Bojsen et al. |
| 2008/0131951 | A1 | 6/2008 | Bojsen et al. |
| 2009/0047384 | A1 | 2/2009 | Bojsen et al. |

FOREIGN PATENT DOCUMENTS

| | | |
|---|---|---|
| CA | 2715086 A1 | 6/2000 |
| EP | 0 109 244 | 5/1984 |
| EP | 0 260 105 | 3/1988 |
| EP | 0 575 133 | 12/1993 |
| EP | 0 585 988 | 9/1994 |
| EP | 0 870 840 | 10/1998 |
| JP | 2-49593 | 2/1990 |
| JP | 4-135456 | 5/1992 |
| JP | 6-113845 | 4/1994 |
| JP | 10-42884 | 2/1998 |
| WO | WO 92/05249 | 4/1992 |
| WO | WO 93/01285 | 1/1993 |
| WO | WO 94/03578 | 2/1994 |
| WO | WO 94/04035 | 3/1994 |
| WO | WO 94/14964 | 7/1994 |
| WO | WO 94/25577 | 11/1994 |
| WO | WO 97/07202 | 2/1997 |
| WO | 98/14594 A2 | 4/1998 |
| WO | WO 98/26057 | 6/1998 |
| WO | WO 98/45453 | 10/1998 |
| WO | WO 99/53769 | 10/1999 |
| WO | WO 00/32758 | 6/2000 |
| WO | WO 01/29222 | 4/2001 |
| WO | WO 01/39602 | 6/2001 |
| WO | WO 01/83770 | 11/2001 |
| WO | WO 02/00852 | 1/2002 |
| WO | WO01/18163 | * 3/2011 ......................... 17/6 |

OTHER PUBLICATIONS

Guo et al., Protein tolerance to random amino acid change, 2004, Proc. Natl. Acad. Sci. USA 101: 9205-9210.*
Lazar et al., Transforming Growth Factor α: Mutation of Aspartic Acid 47 and Leucine 48 Results in Different Biological Activity, 1988, Mol. Cell. Biol. 8:1247-1252.*
Hill et al., Functional Analysis of conserved Histidines in ADP-Glucose Pyrophosphorylase from Escherichia coli, 1998, Biochem. Biophys. Res. Comm. 244:573-577.*
Wacey et al., Disentangling the perturbational effects of amino acid substitutions in the DNA-binding domain of p53., Hum Genet, 1999, vol. 104, pp. 15-22.*
Lynch, Michael, Evolution of the mutation rate., Trends in Genetics, (2010) vol. 26, pp. 345-352.*
Branden et al, "Introduction to Protein Structure", Garland Publishing Inc., NY p. 247 and p. 350 (1991).
Brzozowski et al., Biochemistry, vol. 39, pp. 15071-15082 (2000).
Brzozowski et al., Nature, vol. 351, pp. 491-494 (1991).
Brzozowski et al., Metabolic Engineering, vol. 1, pp. 224-231 (1999).
Cajal et al., Biochemistry, vol. 39, pp. 413-423 (2000).
Dec. 12, 2008 Office Action in U.S. Appl. No. 11/951,597 (US 2008/0131951).
Gaskin et al., Biotechnology and Bioengineering, vol. 73, pp. 433-441 (2001).
Guo et al., Proc. Natl. Acad. Sci. vol. 101, pp. 9205-9210 (2004).

(Continued)

*Primary Examiner* — Alexander Kim
(74) *Attorney, Agent, or Firm* — Kristin J. McNamara

(57) ABSTRACT

The inventors have developed a method using protein engineering to produce lipolytic enzymes having a relatively high activity for one ester bond in an amphiphilic substrate with two lipophilic groups) and a relatively low activity for the ester bond in an amphiphilic substrate with one lipophilic group, e.g. a relatively high phospholipase activity and a relatively low lysophospholipase activity.

12 Claims, 40 Drawing Sheets

(56) References Cited

OTHER PUBLICATIONS

Hill et al., Biochemical Biophysical Res. Comm. vol. 244, pp. 573-577 (1998).
Klein et al., Lipids, vol. 32, pp. 123-130 (1997).
Lawson et al, Protein Engineering, vol. 7, pp. 543-550 (1994).
Lazar et al., Mol. Cell. Biol. vol. 8, pp. 1247-1252 (1988).
Peters et al, Protein Engineering, vol. 10, pp. 149-158 (1997).
Witkowski et al., Biochemistry, vol. 38, pp. 11643-11650 (1999).
Online NEFA-C Assay Test Kit Product Description, Obtained from www.clpmag.com, last reviewed on Mar. 19, 2010, 3 pages.
Online Dictionary Definition of "Polyol", Obtained from Encarta. Msn.com, last viewed on Mar. 19, 2010, 2 pages.

* cited by examiner

Fig. 1
3D structure of *Thermomyces lanuginosus* lipase docked with lecithin

```
ATOM      1  N   GLU B   1     -20.466  -0.687  -7.615  0.00  0.00           N
ATOM      2  CA  GLU B   1     -20.359  -1.989  -6.986  0.00  0.00           C
ATOM      3  C   GLU B   1     -19.088  -2.775  -7.345  0.00  0.00           C
ATOM      4  O   GLU B   1     -18.379  -2.717  -8.352  0.00  0.00           O
ATOM      5  CB  GLU B   1     -21.505  -2.986  -7.267  0.00  0.00           C
ATOM      6  CG  GLU B   1     -22.640  -3.127  -6.294  0.00  0.00           C
ATOM      7  CD  GLU B   1     -22.816  -3.646  -4.918  0.00  0.00           C
ATOM      8  OE1 GLU B   1     -23.898  -4.183  -4.595  0.00  0.00           O
ATOM      9  OE2 GLU B   1     -21.911  -3.529  -4.045  0.00  0.00           O
ATOM     10  N   VAL B   2     -18.891  -3.622  -6.331  0.00  0.00           N
ATOM     11  CA  VAL B   2     -17.758  -4.540  -6.297  0.00  0.00           C
ATOM     12  C   VAL B   2     -17.940  -5.789  -5.453  0.00  0.00           C
ATOM     13  O   VAL B   2     -18.520  -5.817  -4.344  0.00  0.00           O
ATOM     14  CB  VAL B   2     -16.625  -3.596  -5.795  0.00  0.00           C
ATOM     15  CG1 VAL B   2     -16.528  -3.620  -4.292  0.00  0.00           C
ATOM     16  CG2 VAL B   2     -15.360  -3.922  -6.542  0.00  0.00           C
ATOM     17  N   SER B   3     -17.361  -6.824  -6.068  0.00  0.00           N
ATOM     18  CA  SER B   3     -17.298  -8.144  -5.411  0.00  0.00           C
ATOM     19  C   SER B   3     -16.576  -7.883  -4.089  0.00  0.00           C
ATOM     20  O   SER B   3     -15.806  -6.889  -4.045  0.00  0.00           O
ATOM     21  CB  SER B   3     -16.515  -9.110  -6.270  0.00  0.00           C
ATOM     22  OG  SER B   3     -15.546  -9.683  -5.389  0.00  0.00           O
ATOM     23  N   GLN B   4     -16.743  -8.657  -3.040  0.00  0.00           N
ATOM     24  CA  GLN B   4     -15.969  -8.293  -1.796  0.00  0.00           C
ATOM     25  C   GLN B   4     -14.564  -8.801  -2.124  0.00  0.00           C
ATOM     26  O   GLN B   4     -13.647  -8.204  -1.547  0.00  0.00           O
ATOM     27  CB  GLN B   4     -16.623  -8.685  -0.541  0.00  0.00           C
ATOM     28  CG  GLN B   4     -16.654  -8.513   0.906  0.00  0.00           C
ATOM     29  CD  GLN B   4     -16.396  -7.253   1.657  0.00  0.00           C
ATOM     30  OE1 GLN B   4     -15.532  -6.465   1.274  0.00  0.00           O
ATOM     31  NE2 GLN B   4     -17.094  -6.999   2.770  0.00  0.00           N
ATOM     32  N   ASP B   5     -14.435  -9.846  -2.923  0.00  0.00           N
ATOM     33  CA  ASP B   5     -13.122 -10.372  -3.317  0.00  0.00           C
ATOM     34  C   ASP B   5     -12.524  -9.498  -4.444  0.00  0.00           C
ATOM     35  O   ASP B   5     -11.328  -9.717  -4.741  0.00  0.00           O
ATOM     36  CB  ASP B   5     -12.934 -11.835  -3.756  0.00  0.00           C
ATOM     37  CG  ASP B   5     -11.448 -12.248  -3.619  0.00  0.00           C
ATOM     38  OD1 ASP B   5     -10.664 -12.482  -4.568  0.00  0.00           O
ATOM     39  OD2 ASP B   5     -11.016 -12.294  -2.432  0.00  0.00           O
ATOM     40  N   LEU B   6     -13.332  -8.722  -5.157  0.00  0.00           N
ATOM     41  CA  LEU B   6     -12.674  -7.931  -6.220  0.00  0.00           C
ATOM     42  C   LEU B   6     -12.054  -6.747  -5.478  0.00  0.00           C
ATOM     43  O   LEU B   6     -10.898  -6.366  -5.536  0.00  0.00           O
ATOM     44  CB  LEU B   6     -13.562  -7.459  -7.347  0.00  0.00           C
ATOM     45  CG  LEU B   6     -12.813  -6.791  -8.502  0.00  0.00           C
ATOM     46  CD1 LEU B   6     -11.383  -7.312  -8.617  0.00  0.00           C
ATOM     47  CD2 LEU B   6     -13.611  -7.084  -9.774  0.00  0.00           C
ATOM     48  N   PHE B   7     -12.981  -6.261  -4.658  0.00  0.00           N
ATOM     49  CA  PHE B   7     -12.747  -5.102  -3.803  0.00  0.00           C
ATOM     50  C   PHE B   7     -11.401  -5.345  -3.134  0.00  0.00           C
ATOM     51  O   PHE B   7     -10.436  -4.593  -3.256  0.00  0.00           O
ATOM     52  CB  PHE B   7     -13.882  -4.975  -2.775  0.00  0.00           C
ATOM     53  CG  PHE B   7     -13.684  -3.819  -1.846  0.00  0.00           C
ATOM     54  CD1 PHE B   7     -14.259  -2.582  -2.150  0.00  0.00           C
```

```
ATOM     55  CD2 PHE B   7     -12.885  -3.954  -0.722  0.00  0.00           C
ATOM     56  CE1 PHE B   7     -14.033  -1.506  -1.320  0.00  0.00           C
ATOM     57  CE2 PHE B   7     -12.660  -2.875   0.130  0.00  0.00           C
ATOM     58  CZ  PHE B   7     -13.246  -1.642  -0.176  0.00  0.00           C
ATOM     59  N   ASN B   8     -11.355  -6.490  -2.507  0.00  0.00           N
ATOM     60  CA  ASN B   8     -10.198  -6.952  -1.722  0.00  0.00           C
ATOM     61  C   ASN B   8      -8.904  -6.951  -2.523  0.00  0.00           C
ATOM     62  O   ASN B   8      -7.919  -6.377  -1.964  0.00  0.00           O
ATOM     63  CB  ASN B   8     -10.664  -8.270  -1.072  0.00  0.00           C
ATOM     64  CG  ASN B   8     -11.217  -8.078   0.333  0.00  0.00           C
ATOM     65  OD1 ASN B   8     -10.712  -7.260   1.111  0.00  0.00           O
ATOM     66  ND2 ASN B   8     -12.247  -8.837   0.679  0.00  0.00           N
ATOM     67  N   GLN B   9      -8.842  -7.446  -3.740  0.00  0.00           N
ATOM     68  CA  GLN B   9      -7.563  -7.399  -4.483  0.00  0.00           C
ATOM     69  C   GLN B   9      -7.145  -5.943  -4.695  0.00  0.00           C
ATOM     70  O   GLN B   9      -6.014  -5.512  -4.363  0.00  0.00           O
ATOM     71  CB  GLN B   9      -7.669  -8.111  -5.815  0.00  0.00           C
ATOM     72  CG  GLN B   9      -8.771  -9.152  -5.839  0.00  0.00           C
ATOM     73  CD  GLN B   9      -8.305 -10.386  -6.564  0.00  0.00           C
ATOM     74  OE1 GLN B   9      -7.162 -10.790  -6.347  0.00  0.00           O
ATOM     75  NE2 GLN B   9      -9.150 -10.943  -7.410  0.00  0.00           N
ATOM     76  N   PHE B  10      -8.083  -5.111  -5.120  0.00  0.00           N
ATOM     77  CA  PHE B  10      -7.988  -3.698  -5.423  0.00  0.00           C
ATOM     78  C   PHE B  10      -7.230  -2.939  -4.340  0.00  0.00           C
ATOM     79  O   PHE B  10      -6.509  -2.009  -4.674  0.00  0.00           O
ATOM     80  CB  PHE B  10      -9.328  -2.959  -5.466  0.00  0.00           C
ATOM     81  CG  PHE B  10     -10.128  -3.134  -6.707  0.00  0.00           C
ATOM     82  CD1 PHE B  10      -9.601  -3.828  -7.793  0.00  0.00           C
ATOM     83  CD2 PHE B  10     -11.389  -2.561  -6.779  0.00  0.00           C
ATOM     84  CE1 PHE B  10     -10.319  -3.980  -8.958  0.00  0.00           C
ATOM     85  CE2 PHE B  10     -12.129  -2.708  -7.959  0.00  0.00           C
ATOM     86  CZ  PHE B  10     -11.580  -3.414  -9.035  0.00  0.00           C
ATOM     87  N   ASN B  11      -7.499  -3.364  -3.154  0.00  0.00           N
ATOM     88  CA  ASN B  11      -6.851  -2.799  -1.990  0.00  0.00           C
ATOM     89  C   ASN B  11      -5.360  -3.072  -1.799  0.00  0.00           C
ATOM     90  O   ASN B  11      -4.469  -2.220  -1.689  0.00  0.00           O
ATOM     91  CB  ASN B  11      -7.731  -3.465  -0.897  0.00  0.00           C
ATOM     92  CG  ASN B  11      -7.901  -2.270   0.044  0.00  0.00           C
ATOM     93  OD1 ASN B  11      -8.910  -1.601  -0.177  0.00  0.00           O
ATOM     94  ND2 ASN B  11      -6.872  -2.145   0.870  0.00  0.00           N
ATOM     95  N   LEU B  12      -5.077  -4.365  -1.812  0.00  0.00           N
ATOM     96  CA  LEU B  12      -3.764  -4.979  -1.623  0.00  0.00           C
ATOM     97  C   LEU B  12      -2.773  -4.582  -2.720  0.00  0.00           C
ATOM     98  O   LEU B  12      -1.603  -4.282  -2.407  0.00  0.00           O
ATOM     99  CB  LEU B  12      -3.962  -6.511  -1.509  0.00  0.00           C
ATOM    100  CG  LEU B  12      -2.706  -7.270  -1.944  0.00  0.00           C
ATOM    101  CD1 LEU B  12      -1.876  -7.434  -0.686  0.00  0.00           C
ATOM    102  CD2 LEU B  12      -3.105  -8.566  -2.607  0.00  0.00           C
ATOM    103  N   PHE B  13      -3.263  -4.607  -3.947  0.00  0.00           N
ATOM    104  CA  PHE B  13      -2.482  -4.200  -5.114  0.00  0.00           C
ATOM    105  C   PHE B  13      -2.294  -2.684  -5.081  0.00  0.00           C
ATOM    106  O   PHE B  13      -1.384  -2.192  -5.747  0.00  0.00           O
ATOM    107  CB  PHE B  13      -3.070  -4.668  -6.433  0.00  0.00           C
ATOM    108  CG  PHE B  13      -3.208  -6.165  -6.446  0.00  0.00           C
ATOM    109  CD1 PHE B  13      -4.428  -6.756  -6.744  0.00  0.00           C
ATOM    110  CD2 PHE B  13      -2.109  -6.969  -6.154  0.00  0.00           C
ATOM    111  CE1 PHE B  13      -4.575  -8.127  -6.734  0.00  0.00           C
ATOM    112  CE2 PHE B  13      -2.216  -8.354  -6.129  0.00  0.00           C
ATOM    113  CZ  PHE B  13      -3.471  -8.917  -6.421  0.00  0.00           C
```

FIG. 1 (cont'd)

```
ATOM    114  N   ALA B  14     -3.180  -1.986  -4.391  0.00  0.00           N
ATOM    115  CA  ALA B  14     -3.124  -0.540  -4.236  0.00  0.00           C
ATOM    116  C   ALA B  14     -1.882  -0.274  -3.383  0.00  0.00           C
ATOM    117  O   ALA B  14     -1.146   0.666  -3.628  0.00  0.00           O
ATOM    118  CB  ALA B  14     -4.318   0.060  -3.550  0.00  0.00           C
ATOM    119  N   GLN B  15     -1.756  -1.128  -2.394  0.00  0.00           N
ATOM    120  CA  GLN B  15     -0.704  -1.247  -1.375  0.00  0.00           C
ATOM    121  C   GLN B  15      0.559  -1.754  -2.048  0.00  0.00           C
ATOM    122  O   GLN B  15      1.654  -1.190  -1.939  0.00  0.00           O
ATOM    123  CB  GLN B  15     -1.188  -2.116  -0.206  0.00  0.00           C
ATOM    124  CG  GLN B  15     -2.449  -1.571   0.394  0.00  0.00           C
ATOM    125  CD  GLN B  15     -2.970  -1.835   1.764  0.00  0.00           C
ATOM    126  OE1 GLN B  15     -4.107  -1.456   2.111  0.00  0.00           O
ATOM    127  NE2 GLN B  15     -2.164  -2.466   2.610  0.00  0.00           N
ATOM    128  N   TYR B  16      0.452  -2.767  -2.869  0.00  0.00           N
ATOM    129  CA  TYR B  16      1.567  -3.317  -3.641  0.00  0.00           C
ATOM    130  C   TYR B  16      2.258  -2.273  -4.500  0.00  0.00           C
ATOM    131  O   TYR B  16      3.491  -2.305  -4.656  0.00  0.00           O
ATOM    132  CB  TYR B  16      1.012  -4.476  -4.512  0.00  0.00           C
ATOM    133  CG  TYR B  16      1.501  -5.737  -3.838  0.00  0.00           C
ATOM    134  CD1 TYR B  16      2.833  -6.087  -4.067  0.00  0.00           C
ATOM    135  CD2 TYR B  16      0.746  -6.508  -2.982  0.00  0.00           C
ATOM    136  CE1 TYR B  16      3.392  -7.213  -3.464  0.00  0.00           C
ATOM    137  CE2 TYR B  16      1.292  -7.641  -2.384  0.00  0.00           C
ATOM    138  CZ  TYR B  16      2.610  -8.000  -2.625  0.00  0.00           C
ATOM    139  OH  TYR B  16      3.154  -9.119  -2.057  0.00  0.00           O
ATOM    140  N   SER B  17      1.497  -1.384  -5.124  0.00  0.00           N
ATOM    141  CA  SER B  17      1.893  -0.269  -5.978  0.00  0.00           C
ATOM    142  C   SER B  17      2.422   0.945  -5.181  0.00  0.00           C
ATOM    143  O   SER B  17      3.353   1.669  -5.548  0.00  0.00           O
ATOM    144  CB  SER B  17      0.790   0.316  -6.843  0.00  0.00           C
ATOM    145  OG  SER B  17     -0.135  -0.480  -7.501  0.00  0.00           O
ATOM    146  N   ALA B  18      1.764   1.193  -4.077  0.00  0.00           N
ATOM    147  CA  ALA B  18      2.010   2.304  -3.159  0.00  0.00           C
ATOM    148  C   ALA B  18      3.390   2.255  -2.537  0.00  0.00           C
ATOM    149  O   ALA B  18      4.116   3.200  -2.225  0.00  0.00           O
ATOM    150  CB  ALA B  18      0.907   2.295  -2.102  0.00  0.00           C
ATOM    151  N   ALA B  19      3.768   1.031  -2.322  0.00  0.00           N
ATOM    152  CA  ALA B  19      4.938   0.445  -1.745  0.00  0.00           C
ATOM    153  C   ALA B  19      6.150   0.686  -2.612  0.00  0.00           C
ATOM    154  O   ALA B  19      7.223   0.600  -2.018  0.00  0.00           O
ATOM    155  CB  ALA B  19      4.773  -1.064  -1.589  0.00  0.00           C
ATOM    156  N   ALA B  20      5.930   0.899  -3.888  0.00  0.00           N
ATOM    157  CA  ALA B  20      7.065   1.078  -4.819  0.00  0.00           C
ATOM    158  C   ALA B  20      7.666   2.467  -4.756  0.00  0.00           C
ATOM    159  O   ALA B  20      8.719   2.812  -5.320  0.00  0.00           O
ATOM    160  CB  ALA B  20      6.578   0.651  -6.193  0.00  0.00           C
ATOM    161  N   TYR B  21      6.978   3.337  -4.029  0.00  0.00           N
ATOM    162  CA  TYR B  21      7.486   4.702  -3.859  0.00  0.00           C
ATOM    163  C   TYR B  21      8.584   4.536  -2.816  0.00  0.00           C
ATOM    164  O   TYR B  21      9.631   5.109  -3.127  0.00  0.00           O
ATOM    165  CB  TYR B  21      6.405   5.726  -3.539  0.00  0.00           C
ATOM    166  CG  TYR B  21      5.690   6.063  -4.829  0.00  0.00           C
ATOM    167  CD1 TYR B  21      6.026   7.147  -5.628  0.00  0.00           C
ATOM    168  CD2 TYR B  21      4.660   5.228  -5.249  0.00  0.00           C
ATOM    169  CE1 TYR B  21      5.345   7.426  -6.811  0.00  0.00           C
ATOM    170  CE2 TYR B  21      3.966   5.497  -6.433  0.00  0.00           C
ATOM    171  CZ  TYR B  21      4.308   6.597  -7.213  0.00  0.00           C
ATOM    172  OH  TYR B  21      3.587   6.756  -8.355  0.00  0.00           O
```

FIG. 1 (cont'd)

```
ATOM    173  N   CYS B  22       8.357   3.790  -1.762  0.00  0.00           N
ATOM    174  CA  CYS B  22       9.346   3.537  -0.698  0.00  0.00           C
ATOM    175  C   CYS B  22      10.706   3.061  -1.219  0.00  0.00           C
ATOM    176  O   CYS B  22      10.976   1.911  -1.618  0.00  0.00           O
ATOM    177  CB  CYS B  22       8.865   2.514   0.328  0.00  0.00           C
ATOM    178  SG  CYS B  22       7.222   2.816   0.947  0.00  0.00           S
ATOM    179  N   GLY B  23      11.631   4.004  -1.120  0.00  0.00           N
ATOM    180  CA  GLY B  23      13.031   3.972  -1.513  0.00  0.00           C
ATOM    181  C   GLY B  23      13.829   2.809  -0.956  0.00  0.00           C
ATOM    182  O   GLY B  23      14.857   2.395  -1.536  0.00  0.00           O
ATOM    183  N   LYS B  24      13.386   2.274   0.167  0.00  0.00           N
ATOM    184  CA  LYS B  24      13.938   1.097   0.834  0.00  0.00           C
ATOM    185  C   LYS B  24      13.631  -0.095  -0.085  0.00  0.00           C
ATOM    186  O   LYS B  24      14.483  -0.954  -0.379  0.00  0.00           O
ATOM    187  CB  LYS B  24      13.362   0.979   2.236  0.00  0.00           C
ATOM    188  CG  LYS B  24      13.741  -0.174   3.157  0.00  0.00           C
ATOM    189  CD  LYS B  24      13.192  -0.065   4.589  0.00  0.00           C
ATOM    190  CE  LYS B  24      13.833  -0.999   5.606  0.00  0.00           C
ATOM    191  NZ  LYS B  24      13.491  -0.704   7.025  0.00  0.00           N
ATOM    192  N   ASN B  25      12.429  -0.171  -0.645  0.00  0.00           N
ATOM    193  CA  ASN B  25      12.002  -1.280  -1.502  0.00  0.00           C
ATOM    194  C   ASN B  25      12.473  -1.194  -2.950  0.00  0.00           C
ATOM    195  O   ASN B  25      12.139  -2.050  -3.808  0.00  0.00           O
ATOM    196  CB  ASN B  25      10.482  -1.415  -1.382  0.00  0.00           C
ATOM    197  CG  ASN B  25       9.960  -1.596   0.017  0.00  0.00           C
ATOM    198  OD1 ASN B  25       8.764  -1.844   0.251  0.00  0.00           O
ATOM    199  ND2 ASN B  25      10.826  -1.493   1.023  0.00  0.00           N
ATOM    200  N   ASN B  26      13.276  -0.201  -3.245  0.00  0.00           N
ATOM    201  CA  ASN B  26      13.757  -0.040  -4.632  0.00  0.00           C
ATOM    202  C   ASN B  26      15.110  -0.651  -4.905  0.00  0.00           C
ATOM    203  O   ASN B  26      15.326  -0.959  -6.072  0.00  0.00           O
ATOM    204  CB  ASN B  26      13.756   1.453  -4.934  0.00  0.00           C
ATOM    205  CG  ASN B  26      12.399   1.831  -5.475  0.00  0.00           C
ATOM    206  OD1 ASN B  26      12.348   3.012  -5.821  0.00  0.00           O
ATOM    207  ND2 ASN B  26      11.469   0.898  -5.548  0.00  0.00           N
ATOM    208  N   ASP B  27      15.897  -0.716  -3.862  0.00  0.00           N
ATOM    209  CA  ASP B  27      17.231  -1.325  -3.966  0.00  0.00           C
ATOM    210  C   ASP B  27      17.608  -1.565  -2.484  0.00  0.00           C
ATOM    211  O   ASP B  27      18.175  -0.768  -1.761  0.00  0.00           O
ATOM    212  CB  ASP B  27      18.242  -0.649  -4.840  0.00  0.00           C
ATOM    213  CG  ASP B  27      18.413  -1.386  -6.171  0.00  0.00           C
ATOM    214  OD1 ASP B  27      18.457  -0.761  -7.248  0.00  0.00           O
ATOM    215  OD2 ASP B  27      18.517  -2.636  -6.209  0.00  0.00           O
ATOM    216  N   ALA B  28      17.156  -2.743  -2.174  0.00  0.00           N
ATOM    217  CA  ALA B  28      16.934  -3.807  -1.278  0.00  0.00           C
ATOM    218  C   ALA B  28      17.392  -5.178  -1.831  0.00  0.00           C
ATOM    219  O   ALA B  28      17.369  -5.454  -3.039  0.00  0.00           O
ATOM    220  CB  ALA B  28      15.434  -4.089  -1.007  0.00  0.00           C
ATOM    221  N   PRO B  29      17.775  -6.044  -0.888  0.00  0.00           N
ATOM    222  CA  PRO B  29      18.296  -7.387  -1.168  0.00  0.00           C
ATOM    223  C   PRO B  29      17.273  -8.465  -1.437  0.00  0.00           C
ATOM    224  O   PRO B  29      16.174  -8.628  -0.881  0.00  0.00           O
ATOM    225  CB  PRO B  29      19.170  -7.711   0.041  0.00  0.00           C
ATOM    226  CG  PRO B  29      18.957  -6.649   1.078  0.00  0.00           C
ATOM    227  CD  PRO B  29      17.831  -5.767   0.567  0.00  0.00           C
ATOM    228  N   ALA B  30      17.672  -9.351  -2.318  0.00  0.00           N
ATOM    229  CA  ALA B  30      16.910 -10.491  -2.816  0.00  0.00           C
ATOM    230  C   ALA B  30      16.166 -11.355  -1.816  0.00  0.00           C
ATOM    231  O   ALA B  30      15.312 -12.173  -2.282  0.00  0.00           O
```

FIG. 1 (cont'd)

```
ATOM    232  CB   ALA B  30      17.910 -11.310  -3.670  0.00  0.00           C
ATOM    233  N    GLY B  31      16.362 -11.293  -0.517  0.00  0.00           N
ATOM    234  CA   GLY B  31      15.579 -12.209   0.331  0.00  0.00           C
ATOM    235  C    GLY B  31      14.662 -11.499   1.304  0.00  0.00           C
ATOM    236  O    GLY B  31      13.683 -12.078   1.800  0.00  0.00           O
ATOM    237  N    THR B  32      15.037 -10.278   1.541  0.00  0.00           N
ATOM    238  CA   THR B  32      14.358  -9.366   2.473  0.00  0.00           C
ATOM    239  C    THR B  32      12.854  -9.431   2.419  0.00  0.00           C
ATOM    240  O    THR B  32      12.248  -9.999   1.492  0.00  0.00           O
ATOM    241  CB   THR B  32      15.049  -7.976   2.137  0.00  0.00           C
ATOM    242  OG1  THR B  32      16.408  -8.228   2.685  0.00  0.00           O
ATOM    243  CG2  THR B  32      14.470  -6.666   2.657  0.00  0.00           C
ATOM    244  N    ASN B  33      12.226  -8.845   3.424  0.00  0.00           N
ATOM    245  CA   ASN B  33      10.767  -8.746   3.607  0.00  0.00           C
ATOM    246  C    ASN B  33      10.216  -7.432   3.061  0.00  0.00           C
ATOM    247  O    ASN B  33      10.762  -6.417   3.533  0.00  0.00           O
ATOM    248  CB   ASN B  33      10.545  -8.934   5.114  0.00  0.00           C
ATOM    249  CG   ASN B  33       9.530 -10.011   5.460  0.00  0.00           C
ATOM    250  OD1  ASN B  33       9.752 -10.846   6.362  0.00  0.00           O
ATOM    251  ND2  ASN B  33       8.396 -10.006   4.735  0.00  0.00           N
ATOM    252  N    ILE B  34       9.239  -7.310   2.175  0.00  0.00           N
ATOM    253  CA   ILE B  34       8.760  -6.007   1.672  0.00  0.00           C
ATOM    254  C    ILE B  34       7.968  -5.254   2.747  0.00  0.00           C
ATOM    255  O    ILE B  34       6.778  -5.406   3.005  0.00  0.00           O
ATOM    256  CB   ILE B  34       8.020  -6.090   0.296  0.00  0.00           C
ATOM    257  CG1  ILE B  34       6.869  -7.113   0.145  0.00  0.00           C
ATOM    258  CG2  ILE B  34       9.022  -6.426  -0.843  0.00  0.00           C
ATOM    259  CD1  ILE B  34       6.721  -7.771  -1.281  0.00  0.00           C
ATOM    260  N    THR B  35       8.660  -4.348   3.411  0.00  0.00           N
ATOM    261  CA   THR B  35       8.248  -3.465   4.496  0.00  0.00           C
ATOM    262  C    THR B  35       7.982  -2.054   3.991  0.00  0.00           C
ATOM    263  O    THR B  35       8.667  -1.714   3.009  0.00  0.00           O
ATOM    264  CB   THR B  35       9.349  -3.508   5.633  0.00  0.00           C
ATOM    265  OG1  THR B  35       9.551  -2.079   5.916  0.00  0.00           O
ATOM    266  CG2  THR B  35      10.646  -4.240   5.278  0.00  0.00           C
ATOM    267  N    CYS B  36       7.071  -1.297   4.588  0.00  0.00           N
ATOM    268  CA   CYS B  36       6.762   0.067   4.124  0.00  0.00           C
ATOM    269  C    CYS B  36       6.857   1.120   5.230  0.00  0.00           C
ATOM    270  O    CYS B  36       6.224   1.052   6.288  0.00  0.00           O
ATOM    271  CB   CYS B  36       5.390   0.154   3.447  0.00  0.00           C
ATOM    272  SG   CYS B  36       5.298  -0.969   2.017  0.00  0.00           S
ATOM    273  N    THR B  37       7.692   2.103   4.937  0.00  0.00           N
ATOM    274  CA   THR B  37       8.015   3.264   5.759  0.00  0.00           C
ATOM    275  C    THR B  37       6.712   3.847   6.316  0.00  0.00           C
ATOM    276  O    THR B  37       5.967   4.504   5.572  0.00  0.00           O
ATOM    277  CB   THR B  37       8.882   4.339   4.992  0.00  0.00           C
ATOM    278  OG1  THR B  37      10.252   3.815   4.873  0.00  0.00           O
ATOM    279  CG2  THR B  37       8.919   5.708   5.678  0.00  0.00           C
ATOM    280  N    GLY B  38       6.477   3.569   7.597  0.00  0.00           N
ATOM    281  CA   GLY B  38       5.263   4.009   8.301  0.00  0.00           C
ATOM    282  C    GLY B  38       3.989   3.569   7.558  0.00  0.00           C
ATOM    283  O    GLY B  38       3.807   2.435   7.076  0.00  0.00           O
ATOM    284  N    ASN B  39       3.086   4.519   7.454  0.00  0.00           N
ATOM    285  CA   ASN B  39       1.755   4.458   6.849  0.00  0.00           C
ATOM    286  C    ASN B  39       1.617   3.286   5.880  0.00  0.00           C
ATOM    287  O    ASN B  39       1.386   2.125   6.249  0.00  0.00           O
ATOM    288  CB   ASN B  39       1.388   5.822   6.247  0.00  0.00           C
ATOM    289  CG   ASN B  39       1.971   7.015   6.989  0.00  0.00           C
ATOM    290  OD1  ASN B  39       1.992   7.062   8.233  0.00  0.00           O
```

FIG. 1 (cont'd)

```
ATOM    291  ND2 ASN B  39       2.487   8.035   6.283  0.00  0.00           N
ATOM    292  N   ALA B  40       1.719   3.610   4.635  0.00  0.00           N
ATOM    293  CA  ALA B  40       1.687   2.879   3.407  0.00  0.00           C
ATOM    294  C   ALA B  40       1.391   1.424   3.149  0.00  0.00           C
ATOM    295  O   ALA B  40       0.983   1.266   1.949  0.00  0.00           O
ATOM    296  CB  ALA B  40       3.193   2.962   2.934  0.00  0.00           C
ATOM    297  N   CYS B  41       1.605   0.398   3.958  0.00  0.00           N
ATOM    298  CA  CYS B  41       1.279  -0.974   3.424  0.00  0.00           C
ATOM    299  C   CYS B  41       1.041  -2.130   4.377  0.00  0.00           C
ATOM    300  O   CYS B  41       1.651  -3.189   4.239  0.00  0.00           O
ATOM    301  CB  CYS B  41       2.385  -1.253   2.433  0.00  0.00           C
ATOM    302  SG  CYS B  41       3.830  -2.286   2.566  0.00  0.00           S
ATOM    303  N   PRO B  42       0.073  -2.014   5.271  0.00  0.00           N
ATOM    304  CA  PRO B  42      -0.260  -3.024   6.261  0.00  0.00           C
ATOM    305  C   PRO B  42      -0.574  -4.416   5.776  0.00  0.00           C
ATOM    306  O   PRO B  42      -0.172  -5.381   6.432  0.00  0.00           O
ATOM    307  CB  PRO B  42      -1.507  -2.441   6.965  0.00  0.00           C
ATOM    308  CG  PRO B  42      -1.393  -0.935   6.811  0.00  0.00           C
ATOM    309  CD  PRO B  42      -0.719  -0.768   5.460  0.00  0.00           C
ATOM    310  N   GLU B  43      -1.287  -4.560   4.694  0.00  0.00           N
ATOM    311  CA  GLU B  43      -1.748  -5.771   4.026  0.00  0.00           C
ATOM    312  C   GLU B  43      -0.641  -6.615   3.409  0.00  0.00           C
ATOM    313  O   GLU B  43      -0.770  -7.850   3.306  0.00  0.00           O
ATOM    314  CB  GLU B  43      -2.769  -5.490   2.898  0.00  0.00           C
ATOM    315  CG  GLU B  43      -4.224  -5.876   3.155  0.00  0.00           C
ATOM    316  CD  GLU B  43      -5.010  -5.022   4.098  0.00  0.00           C
ATOM    317  OE1 GLU B  43      -6.232  -4.990   4.063  0.00  0.00           O
ATOM    318  OE2 GLU B  43      -4.405  -4.338   4.961  0.00  0.00           O
ATOM    319  N   VAL B  44       0.369  -5.933   2.908  0.00  0.00           N
ATOM    320  CA  VAL B  44       1.548  -6.572   2.292  0.00  0.00           C
ATOM    321  C   VAL B  44       2.482  -7.084   3.388  0.00  0.00           C
ATOM    322  O   VAL B  44       2.929  -8.250   3.426  0.00  0.00           O
ATOM    323  CB  VAL B  44       2.117  -5.536   1.309  0.00  0.00           C
ATOM    324  CG1 VAL B  44       3.582  -5.676   0.930  0.00  0.00           C
ATOM    325  CG2 VAL B  44       1.216  -5.561   0.081  0.00  0.00           C
ATOM    326  N   GLU B  45       2.723  -6.181   4.347  0.00  0.00           N
ATOM    327  CA  GLU B  45       3.613  -6.451   5.478  0.00  0.00           C
ATOM    328  C   GLU B  45       3.099  -7.736   6.123  0.00  0.00           C
ATOM    329  O   GLU B  45       3.741  -8.813   5.991  0.00  0.00           O
ATOM    330  CB  GLU B  45       3.616  -5.486   6.651  0.00  0.00           C
ATOM    331  CG  GLU B  45       3.559  -3.980   6.455  0.00  0.00           C
ATOM    332  CD  GLU B  45       4.935  -3.425   6.197  0.00  0.00           C
ATOM    333  OE1 GLU B  45       5.893  -4.156   6.389  0.00  0.00           O
ATOM    334  OE2 GLU B  45       5.015  -2.243   5.813  0.00  0.00           O
ATOM    335  N   LYS B  46       1.857  -7.657   6.607  0.00  0.00           N
ATOM    336  CA  LYS B  46       1.268  -8.849   7.261  0.00  0.00           C
ATOM    337  C   LYS B  46       1.258 -10.043   6.309  0.00  0.00           C
ATOM    338  O   LYS B  46       0.673 -11.017   6.838  0.00  0.00           O
ATOM    339  CB  LYS B  46       0.056  -8.580   8.090  0.00  0.00           C
ATOM    340  CG  LYS B  46      -1.246  -7.968   7.687  0.00  0.00           C
ATOM    341  CD  LYS B  46      -2.391  -8.744   8.364  0.00  0.00           C
ATOM    342  CE  LYS B  46      -2.643  -8.208   9.768  0.00  0.00           C
ATOM    343  NZ  LYS B  46      -3.220  -6.827   9.617  0.00  0.00           N
ATOM    344  N   ALA B  47       1.646 -10.075   5.040  0.00  0.00           N
ATOM    345  CA  ALA B  47       1.636 -11.403   4.383  0.00  0.00           C
ATOM    346  C   ALA B  47       3.024 -12.034   4.547  0.00  0.00           C
ATOM    347  O   ALA B  47       3.766 -11.717   5.524  0.00  0.00           O
ATOM    348  CB  ALA B  47       1.139 -11.216   2.949  0.00  0.00           C
ATOM    349  N   ASP B  48       3.696 -12.555   3.571  0.00  0.00           N
```

FIG. 1 (cont'd)

```
ATOM    350  CA  ASP B  48       4.980 -13.223   3.428  0.00  0.00           C
ATOM    351  C   ASP B  48       5.474 -12.868   2.012  0.00  0.00           C
ATOM    352  O   ASP B  48       5.419 -13.703   1.081  0.00  0.00           O
ATOM    353  CB  ASP B  48       4.846 -14.731   3.623  0.00  0.00           C
ATOM    354  CG  ASP B  48       6.062 -15.586   3.305  0.00  0.00           C
ATOM    355  OD1 ASP B  48       6.945 -15.783   4.180  0.00  0.00           O
ATOM    356  OD2 ASP B  48       6.141 -16.074   2.150  0.00  0.00           O
ATOM    357  N   ALA B  49       5.927 -11.618   1.950  0.00  0.00           N
ATOM    358  CA  ALA B  49       6.366 -11.113   0.611  0.00  0.00           C
ATOM    359  C   ALA B  49       7.812 -10.721   0.802  0.00  0.00           C
ATOM    360  O   ALA B  49       8.289  -9.998   1.672  0.00  0.00           O
ATOM    361  CB  ALA B  49       5.346 -10.093   0.194  0.00  0.00           C
ATOM    362  N   THR B  50       8.519 -11.344  -0.105  0.00  0.00           N
ATOM    363  CA  THR B  50       9.972 -11.363  -0.218  0.00  0.00           C
ATOM    364  C   THR B  50      10.201 -10.907  -1.645  0.00  0.00           C
ATOM    365  O   THR B  50       9.476 -11.443  -2.495  0.00  0.00           O
ATOM    366  CB  THR B  50      10.631 -12.772   0.110  0.00  0.00           C
ATOM    367  OG1 THR B  50      10.516 -13.752  -1.012  0.00  0.00           O
ATOM    368  CG2 THR B  50      10.085 -13.458   1.388  0.00  0.00           C
ATOM    369  N   PHE B  51      11.228 -10.107  -1.759  0.00  0.00           N
ATOM    370  CA  PHE B  51      11.555  -9.543  -3.066  0.00  0.00           C
ATOM    371  C   PHE B  51      12.320 -10.624  -3.824  0.00  0.00           C
ATOM    372  O   PHE B  51      12.993 -11.336  -3.049  0.00  0.00           O
ATOM    373  CB  PHE B  51      12.552  -8.410  -2.920  0.00  0.00           C
ATOM    374  CG  PHE B  51      12.227  -7.206  -2.120  0.00  0.00           C
ATOM    375  CD1 PHE B  51      11.833  -6.049  -2.806  0.00  0.00           C
ATOM    376  CD2 PHE B  51      12.323  -7.176  -0.730  0.00  0.00           C
ATOM    377  CE1 PHE B  51      11.521  -4.883  -2.118  0.00  0.00           C
ATOM    378  CE2 PHE B  51      12.024  -6.005  -0.011  0.00  0.00           C
ATOM    379  CZ  PHE B  51      11.626  -4.849  -0.716  0.00  0.00           C
ATOM    380  N   LEU B  52      12.129 -10.782  -5.151  0.00  0.00           N
ATOM    381  CA  LEU B  52      13.014 -11.819  -5.701  0.00  0.00           C
ATOM    382  C   LEU B  52      13.758 -11.090  -6.817  0.00  0.00           C
ATOM    383  O   LEU B  52      14.749 -11.684  -7.302  0.00  0.00           O
ATOM    384  CB  LEU B  52      12.224 -12.943  -6.339  0.00  0.00           C
ATOM    385  CG  LEU B  52      10.712 -12.901  -6.297  0.00  0.00           C
ATOM    386  CD1 LEU B  52      10.012 -13.831  -7.279  0.00  0.00           C
ATOM    387  CD2 LEU B  52      10.385 -13.317  -4.864  0.00  0.00           C
ATOM    388  N   TYR B  53      13.540  -9.800  -6.884  0.00  0.00           N
ATOM    389  CA  TYR B  53      14.198  -8.857  -7.786  0.00  0.00           C
ATOM    390  C   TYR B  53      13.697  -7.461  -7.373  0.00  0.00           C
ATOM    391  O   TYR B  53      12.464  -7.336  -7.445  0.00  0.00           O
ATOM    392  CB  TYR B  53      14.005  -9.070  -9.286  0.00  0.00           C
ATOM    393  CG  TYR B  53      14.978  -8.244 -10.117  0.00  0.00           C
ATOM    394  CD1 TYR B  53      16.329  -8.116  -9.768  0.00  0.00           C
ATOM    395  CD2 TYR B  53      14.548  -7.599 -11.281  0.00  0.00           C
ATOM    396  CE1 TYR B  53      17.194  -7.355 -10.551  0.00  0.00           C
ATOM    397  CE2 TYR B  53      15.400  -6.835 -12.077  0.00  0.00           C
ATOM    398  CZ  TYR B  53      16.729  -6.723 -11.705  0.00  0.00           C
ATOM    399  OH  TYR B  53      17.568  -5.982 -12.491  0.00  0.00           O
ATOM    400  N   SER B  54      14.590  -6.569  -7.056  0.00  0.00           N
ATOM    401  CA  SER B  54      14.169  -5.201  -6.641  0.00  0.00           C
ATOM    402  C   SER B  54      15.130  -4.272  -7.364  0.00  0.00           C
ATOM    403  O   SER B  54      16.353  -4.401  -7.203  0.00  0.00           O
ATOM    404  CB  SER B  54      14.128  -5.128  -5.136  0.00  0.00           C
ATOM    405  OG  SER B  54      14.909  -4.052  -4.674  0.00  0.00           O
ATOM    406  N   PHE B  55      14.573  -3.362  -8.147  0.00  0.00           N
ATOM    407  CA  PHE B  55      15.322  -2.476  -9.034  0.00  0.00           C
ATOM    408  C   PHE B  55      14.992  -1.006  -9.120  0.00  0.00           C
```

FIG. 1 (cont'd)

```
ATOM    409  O    PHE B  55      13.827  -0.604  -9.083  0.00  0.00           O
ATOM    410  CB   PHE B  55      15.104  -3.068 -10.445  0.00  0.00           C
ATOM    411  CG   PHE B  55      13.663  -3.167 -10.849  0.00  0.00           C
ATOM    412  CD1  PHE B  55      12.826  -4.171 -10.376  0.00  0.00           C
ATOM    413  CD2  PHE B  55      13.151  -2.216 -11.749  0.00  0.00           C
ATOM    414  CE1  PHE B  55      11.505  -4.247 -10.801  0.00  0.00           C
ATOM    415  CE2  PHE B  55      11.826  -2.287 -12.169  0.00  0.00           C
ATOM    416  CZ   PHE B  55      10.988  -3.304 -11.694  0.00  0.00           C
ATOM    417  N    GLU B  56      16.068  -0.259  -9.248  0.00  0.00           N
ATOM    418  CA   GLU B  56      16.130   1.201  -9.324  0.00  0.00           C
ATOM    419  C    GLU B  56      17.111   1.656 -10.403  0.00  0.00           C
ATOM    420  O    GLU B  56      17.960   0.981 -10.993  0.00  0.00           O
ATOM    421  CB   GLU B  56      16.489   1.911  -8.007  0.00  0.00           C
ATOM    422  CG   GLU B  56      17.867   2.498  -7.799  0.00  0.00           C
ATOM    423  CD   GLU B  56      18.354   2.943  -6.475  0.00  0.00           C
ATOM    424  OE1  GLU B  56      18.632   4.070  -6.102  0.00  0.00           O
ATOM    425  OE2  GLU B  56      18.548   2.045  -5.639  0.00  0.00           O
ATOM    426  N    ASP B  57      16.884   2.890 -10.774  0.00  0.00           N
ATOM    427  CA   ASP B  57      17.512   3.810 -11.717  0.00  0.00           C
ATOM    428  C    ASP B  57      17.927   3.104 -12.996  0.00  0.00           C
ATOM    429  O    ASP B  57      18.886   3.461 -13.672  0.00  0.00           O
ATOM    430  CB   ASP B  57      18.610   4.591 -10.959  0.00  0.00           C
ATOM    431  CG   ASP B  57      18.098   5.867 -10.288  0.00  0.00           C
ATOM    432  OD1  ASP B  57      18.050   6.034  -9.044  0.00  0.00           O
ATOM    433  OD2  ASP B  57      17.720   6.798 -11.056  0.00  0.00           O
ATOM    434  N    SER B  58      17.171   2.139 -13.442  0.00  0.00           N
ATOM    435  CA   SER B  58      17.216   1.216 -14.538  0.00  0.00           C
ATOM    436  C    SER B  58      16.722   1.489 -15.945  0.00  0.00           C
ATOM    437  O    SER B  58      15.525   1.769 -16.133  0.00  0.00           O
ATOM    438  CB   SER B  58      16.253   0.061 -14.119  0.00  0.00           C
ATOM    439  OG   SER B  58      16.883  -1.095 -13.656  0.00  0.00           O
ATOM    440  N    GLY B  59      17.567   1.292 -16.925  0.00  0.00           N
ATOM    441  CA   GLY B  59      17.249   1.426 -18.333  0.00  0.00           C
ATOM    442  C    GLY B  59      17.032   2.850 -18.835  0.00  0.00           C
ATOM    443  O    GLY B  59      17.780   3.778 -18.449  0.00  0.00           O
ATOM    444  N    VAL B  60      15.989   2.970 -19.684  0.00  0.00           N
ATOM    445  CA   VAL B  60      15.770   4.333 -20.215  0.00  0.00           C
ATOM    446  C    VAL B  60      14.984   5.232 -19.293  0.00  0.00           C
ATOM    447  O    VAL B  60      15.801   6.116 -18.825  0.00  0.00           O
ATOM    448  CB   VAL B  60      15.351   4.234 -21.683  0.00  0.00           C
ATOM    449  CG1  VAL B  60      15.503   5.572 -22.394  0.00  0.00           C
ATOM    450  CG2  VAL B  60      16.178   3.227 -22.458  0.00  0.00           C
ATOM    451  N    GLY B  61      13.744   5.269 -18.902  0.00  0.00           N
ATOM    452  CA   GLY B  61      13.363   6.397 -17.995  0.00  0.00           C
ATOM    453  C    GLY B  61      13.541   6.263 -16.525  0.00  0.00           C
ATOM    454  O    GLY B  61      12.576   6.613 -15.816  0.00  0.00           O
ATOM    455  N    ASP B  62      14.631   5.808 -15.949  0.00  0.00           N
ATOM    456  CA   ASP B  62      14.696   5.636 -14.492  0.00  0.00           C
ATOM    457  C    ASP B  62      13.712   4.510 -14.166  0.00  0.00           C
ATOM    458  O    ASP B  62      12.931   4.738 -13.216  0.00  0.00           O
ATOM    459  CB   ASP B  62      14.283   6.844 -13.657  0.00  0.00           C
ATOM    460  CG   ASP B  62      14.705   6.733 -12.205  0.00  0.00           C
ATOM    461  OD1  ASP B  62      15.057   7.681 -11.480  0.00  0.00           O
ATOM    462  OD2  ASP B  62      14.713   5.589 -11.710  0.00  0.00           O
ATOM    463  N    VAL B  63      13.692   3.386 -14.842  0.00  0.00           N
ATOM    464  CA   VAL B  63      12.698   2.348 -14.437  0.00  0.00           C
ATOM    465  C    VAL B  63      12.989   1.767 -13.050  0.00  0.00           C
ATOM    466  O    VAL B  63      13.992   1.159 -12.630  0.00  0.00           O
ATOM    467  CB   VAL B  63      12.626   1.422 -15.657  0.00  0.00           C
```

FIG. 1 (cont'd)

```
ATOM    468  CG1 VAL B  63      11.434   0.476 -15.550  0.00  0.00           C
ATOM    469  CG2 VAL B  63      12.629   2.188 -16.980  0.00  0.00           C
ATOM    470  N   THR B  64      12.043   1.890 -12.133  0.00  0.00           N
ATOM    471  CA  THR B  64      11.956   1.508 -10.753  0.00  0.00           C
ATOM    472  C   THR B  64      10.747   0.751 -10.245  0.00  0.00           C
ATOM    473  O   THR B  64       9.594   1.073 -10.546  0.00  0.00           O
ATOM    474  CB  THR B  64      11.924   2.883  -9.926  0.00  0.00           C
ATOM    475  OG1 THR B  64      13.206   3.478 -10.219  0.00  0.00           O
ATOM    476  CG2 THR B  64      11.615   2.647  -8.463  0.00  0.00           C
ATOM    477  N   GLY B  65      10.978  -0.269  -9.450  0.00  0.00           N
ATOM    478  CA  GLY B  65       9.835  -1.091  -8.935  0.00  0.00           C
ATOM    479  C   GLY B  65      10.585  -2.168  -8.137  0.00  0.00           C
ATOM    480  O   GLY B  65      11.589  -1.805  -7.538  0.00  0.00           O
ATOM    481  N   PHE B  66       9.969  -3.309  -8.033  0.00  0.00           N
ATOM    482  CA  PHE B  66      10.400  -4.572  -7.485  0.00  0.00           C
ATOM    483  C   PHE B  66       9.533  -5.712  -8.081  0.00  0.00           C
ATOM    484  O   PHE B  66       8.381  -5.542  -8.492  0.00  0.00           O
ATOM    485  CB  PHE B  66      10.388  -4.726  -5.961  0.00  0.00           C
ATOM    486  CG  PHE B  66       9.012  -4.583  -5.400  0.00  0.00           C
ATOM    487  CD1 PHE B  66       8.044  -5.570  -5.581  0.00  0.00           C
ATOM    488  CD2 PHE B  66       8.672  -3.428  -4.716  0.00  0.00           C
ATOM    489  CE1 PHE B  66       6.761  -5.420  -5.090  0.00  0.00           C
ATOM    490  CE2 PHE B  66       7.379  -3.262  -4.207  0.00  0.00           C
ATOM    491  CZ  PHE B  66       6.421  -4.263  -4.392  0.00  0.00           C
ATOM    492  N   LEU B  67      10.074  -6.904  -8.027  0.00  0.00           N
ATOM    493  CA  LEU B  67       9.318  -8.101  -8.436  0.00  0.00           C
ATOM    494  C   LEU B  67       9.289  -8.841  -7.090  0.00  0.00           C
ATOM    495  O   LEU B  67      10.380  -8.759  -6.464  0.00  0.00           O
ATOM    496  CB  LEU B  67       9.891  -8.877  -9.591  0.00  0.00           C
ATOM    497  CG  LEU B  67       9.088 -10.160  -9.863  0.00  0.00           C
ATOM    498  CD1 LEU B  67       7.772  -9.828 -10.557  0.00  0.00           C
ATOM    499  CD2 LEU B  67       9.903 -11.123 -10.729  0.00  0.00           C
ATOM    500  N   ALA B  68       8.176  -9.402  -6.673  0.00  0.00           N
ATOM    501  CA  ALA B  68       8.103 -10.060  -5.363  0.00  0.00           C
ATOM    502  C   ALA B  68       7.333 -11.383  -5.406  0.00  0.00           C
ATOM    503  O   ALA B  68       6.699 -11.701  -6.419  0.00  0.00           O
ATOM    504  CB  ALA B  68       7.469  -9.259  -4.249  0.00  0.00           C
ATOM    505  N   LEU B  69       7.503 -12.100  -4.298  0.00  0.00           N
ATOM    506  CA  LEU B  69       6.878 -13.383  -4.034  0.00  0.00           C
ATOM    507  C   LEU B  69       6.011 -13.207  -2.774  0.00  0.00           C
ATOM    508  O   LEU B  69       6.529 -12.840  -1.719  0.00  0.00           O
ATOM    509  CB  LEU B  69       7.836 -14.507  -3.706  0.00  0.00           C
ATOM    510  CG  LEU B  69       7.222 -15.902  -3.782  0.00  0.00           C
ATOM    511  CD1 LEU B  69       6.656 -16.103  -5.186  0.00  0.00           C
ATOM    512  CD2 LEU B  69       8.302 -16.921  -3.461  0.00  0.00           C
ATOM    513  N   ASP B  70       4.770 -13.549  -2.977  0.00  0.00           N
ATOM    514  CA  ASP B  70       3.742 -13.424  -1.906  0.00  0.00           C
ATOM    515  C   ASP B  70       3.368 -14.897  -1.836  0.00  0.00           C
ATOM    516  O   ASP B  70       2.692 -15.467  -2.678  0.00  0.00           O
ATOM    517  CB  ASP B  70       2.688 -12.444  -2.343  0.00  0.00           C
ATOM    518  CG  ASP B  70       1.652 -12.023  -1.343  0.00  0.00           C
ATOM    519  OD1 ASP B  70       0.867 -12.854  -0.885  0.00  0.00           O
ATOM    520  OD2 ASP B  70       1.630 -10.824  -1.000  0.00  0.00           O
ATOM    521  N   ASN B  71       3.849 -15.417  -0.730  0.00  0.00           N
ATOM    522  CA  ASN B  71       3.712 -16.890  -0.475  0.00  0.00           C
ATOM    523  C   ASN B  71       2.521 -17.085   0.444  0.00  0.00           C
ATOM    524  O   ASN B  71       2.230 -18.212   0.853  0.00  0.00           O
ATOM    525  CB  ASN B  71       5.086 -17.283  -0.129  0.00  0.00           C
ATOM    526  CG  ASN B  71       5.807 -18.547   0.016  0.00  0.00           C
```

FIG. 1 (cont'd)

```
ATOM    527  OD1 ASN B  71       6.316 -18.746   1.141  0.00  0.00           O
ATOM    528  ND2 ASN B  71       5.937 -19.359  -1.017  0.00  0.00           N
ATOM    529  N   THR B  72       1.821 -15.999   0.663  0.00  0.00           N
ATOM    530  CA  THR B  72       0.581 -16.054   1.467  0.00  0.00           C
ATOM    531  C   THR B  72      -0.585 -15.908   0.505  0.00  0.00           C
ATOM    532  O   THR B  72      -1.480 -16.784   0.507  0.00  0.00           O
ATOM    533  CB  THR B  72       0.748 -15.071   2.678  0.00  0.00           C
ATOM    534  OG1 THR B  72       1.691 -15.884   3.479  0.00  0.00           O
ATOM    535  CG2 THR B  72      -0.588 -14.659   3.279  0.00  0.00           C
ATOM    536  N   ASN B  73      -0.599 -14.943  -0.392  0.00  0.00           N
ATOM    537  CA  ASN B  73      -1.719 -14.802  -1.353  0.00  0.00           C
ATOM    538  C   ASN B  73      -1.523 -15.727  -2.541  0.00  0.00           C
ATOM    539  O   ASN B  73      -2.431 -15.988  -3.351  0.00  0.00           O
ATOM    540  CB  ASN B  73      -1.877 -13.313  -1.703  0.00  0.00           C
ATOM    541  CG  ASN B  73      -2.178 -12.693  -0.338  0.00  0.00           C
ATOM    542  OD1 ASN B  73      -1.303 -12.095   0.292  0.00  0.00           O
ATOM    543  ND2 ASN B  73      -3.416 -13.016   0.017  0.00  0.00           N
ATOM    544  N   LYS B  74      -0.296 -16.211  -2.611  0.00  0.00           N
ATOM    545  CA  LYS B  74       0.062 -17.125  -3.711  0.00  0.00           C
ATOM    546  C   LYS B  74      -0.099 -16.289  -4.976  0.00  0.00           C
ATOM    547  O   LYS B  74      -0.876 -16.578  -5.894  0.00  0.00           O
ATOM    548  CB  LYS B  74      -0.753 -18.414  -3.644  0.00  0.00           C
ATOM    549  CG  LYS B  74      -0.292 -19.287  -2.447  0.00  0.00           C
ATOM    550  CD  LYS B  74      -0.407 -20.776  -2.775  0.00  0.00           C
ATOM    551  CE  LYS B  74       0.572 -21.645  -2.006  0.00  0.00           C
ATOM    552  NZ  LYS B  74       0.790 -23.002  -2.588  0.00  0.00           N
ATOM    553  N   LEU B  75       0.708 -15.228  -4.942  0.00  0.00           N
ATOM    554  CA  LEU B  75       0.860 -14.208  -5.960  0.00  0.00           C
ATOM    555  C   LEU B  75       2.359 -13.889  -6.141  0.00  0.00           C
ATOM    556  O   LEU B  75       3.160 -13.963  -5.240  0.00  0.00           O
ATOM    557  CB  LEU B  75       0.259 -12.820  -5.746  0.00  0.00           C
ATOM    558  CG  LEU B  75      -0.766 -12.474  -4.718  0.00  0.00           C
ATOM    559  CD1 LEU B  75      -0.419 -11.126  -4.090  0.00  0.00           C
ATOM    560  CD2 LEU B  75      -2.148 -12.406  -5.357  0.00  0.00           C
ATOM    561  N   ILE B  76       2.663 -13.480  -7.328  0.00  0.00           N
ATOM    562  CA  ILE B  76       3.956 -13.002  -7.802  0.00  0.00           C
ATOM    563  C   ILE B  76       3.613 -11.603  -8.315  0.00  0.00           C
ATOM    564  O   ILE B  76       3.202 -11.445  -9.473  0.00  0.00           O
ATOM    565  CB  ILE B  76       4.463 -13.967  -8.913  0.00  0.00           C
ATOM    566  CG1 ILE B  76       4.578 -15.400  -8.357  0.00  0.00           C
ATOM    567  CG2 ILE B  76       5.780 -13.438  -9.533  0.00  0.00           C
ATOM    568  CD1 ILE B  76       5.168 -16.401  -9.392  0.00  0.00           C
ATOM    569  N   VAL B  77       3.921 -10.590  -7.545  0.00  0.00           N
ATOM    570  CA  VAL B  77       3.570  -9.211  -7.850  0.00  0.00           C
ATOM    571  C   VAL B  77       4.803  -8.463  -8.327  0.00  0.00           C
ATOM    572  O   VAL B  77       5.856  -8.608  -7.727  0.00  0.00           O
ATOM    573  CB  VAL B  77       2.964  -8.539  -6.606  0.00  0.00           C
ATOM    574  CG1 VAL B  77       1.931  -7.515  -7.052  0.00  0.00           C
ATOM    575  CG2 VAL B  77       2.434  -9.530  -5.581  0.00  0.00           C
ATOM    576  N   LEU B  78       4.558  -7.729  -9.403  0.00  0.00           N
ATOM    577  CA  LEU B  78       5.581  -6.905 -10.068  0.00  0.00           C
ATOM    578  C   LEU B  78       4.973  -5.497  -9.982  0.00  0.00           C
ATOM    579  O   LEU B  78       3.942  -5.266 -10.630  0.00  0.00           O
ATOM    580  CB  LEU B  78       5.845  -7.316 -11.509  0.00  0.00           C
ATOM    581  CG  LEU B  78       7.170  -6.967 -12.173  0.00  0.00           C
ATOM    582  CD1 LEU B  78       6.985  -6.589 -13.636  0.00  0.00           C
ATOM    583  CD2 LEU B  78       7.865  -5.790 -11.500  0.00  0.00           C
ATOM    584  N   SER B  79       5.660  -4.626  -9.297  0.00  0.00           N
ATOM    585  CA  SER B  79       5.181  -3.267  -9.083  0.00  0.00           C
```

FIG. 1 (cont'd)

```
ATOM    586  C    SER B  79       6.164  -2.263  -9.643  0.00  0.00           C
ATOM    587  O    SER B  79       7.336  -2.419  -9.260  0.00  0.00           O
ATOM    588  CB   SER B  79       5.083  -3.125  -7.583  0.00  0.00           C
ATOM    589  OG   SER B  79       4.329  -2.132  -6.979  0.00  0.00           O
ATOM    590  N    PHE B  80       5.640  -1.299 -10.403  0.00  0.00           N
ATOM    591  CA   PHE B  80       6.521  -0.241 -10.934  0.00  0.00           C
ATOM    592  C    PHE B  80       6.094   1.136 -10.343  0.00  0.00           C
ATOM    593  O    PHE B  80       4.963   1.561 -10.070  0.00  0.00           O
ATOM    594  CB   PHE B  80       6.640  -0.053 -12.410  0.00  0.00           C
ATOM    595  CG   PHE B  80       6.784  -1.157 -13.375  0.00  0.00           C
ATOM    596  CD1  PHE B  80       5.724  -2.038 -13.610  0.00  0.00           C
ATOM    597  CD2  PHE B  80       7.982  -1.297 -14.088  0.00  0.00           C
ATOM    598  CE1  PHE B  80       5.833  -3.070 -14.532  0.00  0.00           C
ATOM    599  CE2  PHE B  80       8.104  -2.336 -15.030  0.00  0.00           C
ATOM    600  CZ   PHE B  80       7.033  -3.229 -15.223  0.00  0.00           C
ATOM    601  N    ARG B  81       7.178   1.869 -10.131  0.00  0.00           N
ATOM    602  CA   ARG B  81       7.094   3.217  -9.560  0.00  0.00           C
ATOM    603  C    ARG B  81       6.624   4.230 -10.614  0.00  0.00           C
ATOM    604  O    ARG B  81       7.106   4.260 -11.739  0.00  0.00           O
ATOM    605  CB   ARG B  81       8.405   3.711  -8.927  0.00  0.00           C
ATOM    606  CG   ARG B  81       8.268   4.834  -7.898  0.00  0.00           C
ATOM    607  CD   ARG B  81       9.605   5.342  -7.478  0.00  0.00           C
ATOM    608  NE   ARG B  81      10.427   5.827  -8.567  0.00  0.00           N
ATOM    609  CZ   ARG B  81      11.546   6.527  -8.411  0.00  0.00           C
ATOM    610  NH1  ARG B  81      11.994   6.814  -7.193  0.00  0.00           N
ATOM    611  NH2  ARG B  81      12.233   6.957  -9.471  0.00  0.00           N
ATOM    612  N    GLY B  82       5.715   5.046 -10.134  0.00  0.00           N
ATOM    613  CA   GLY B  82       5.117   6.157 -10.859  0.00  0.00           C
ATOM    614  C    GLY B  82       6.262   7.186 -10.878  0.00  0.00           C
ATOM    615  O    GLY B  82       7.430   6.899 -10.576  0.00  0.00           O
ATOM    616  N    SER B  83       5.913   8.399 -11.243  0.00  0.00           N
ATOM    617  CA   SER B  83       6.981   9.408 -11.325  0.00  0.00           C
ATOM    618  C    SER B  83       7.433   9.979 -10.003  0.00  0.00           C
ATOM    619  O    SER B  83       6.682  10.264  -9.078  0.00  0.00           O
ATOM    620  CB   SER B  83       6.447  10.478 -12.293  0.00  0.00           C
ATOM    621  OG   SER B  83       5.756   9.722 -13.291  0.00  0.00           O
ATOM    622  N    ARG B  84       8.726  10.222  -9.968  0.00  0.00           N
ATOM    623  CA   ARG B  84       9.414  10.841  -8.861  0.00  0.00           C
ATOM    624  C    ARG B  84      10.555  11.736  -9.338  0.00  0.00           C
ATOM    625  O    ARG B  84      10.577  12.931  -9.031  0.00  0.00           O
ATOM    626  CB   ARG B  84      10.008   9.823  -7.876  0.00  0.00           C
ATOM    627  CG   ARG B  84      10.727  10.457  -6.693  0.00  0.00           C
ATOM    628  CD   ARG B  84      10.369   9.855  -5.388  0.00  0.00           C
ATOM    629  NE   ARG B  84       8.997  10.157  -5.025  0.00  0.00           N
ATOM    630  CZ   ARG B  84       8.344   9.490  -4.065  0.00  0.00           C
ATOM    631  NH1  ARG B  84       8.879   8.490  -3.373  0.00  0.00           N
ATOM    632  NH2  ARG B  84       7.078   9.829  -3.789  0.00  0.00           N
ATOM    633  N    SER B  85      11.505  11.152 -10.021  0.00  0.00           N
ATOM    634  CA   SER B  85      12.707  11.842 -10.469  0.00  0.00           C
ATOM    635  C    SER B  85      12.457  12.646 -11.713  0.00  0.00           C
ATOM    636  O    SER B  85      11.570  12.163 -12.421  0.00  0.00           O
ATOM    637  CB   SER B  85      13.825  10.844 -10.787  0.00  0.00           C
ATOM    638  OG   SER B  85      13.575  10.207 -12.019  0.00  0.00           O
ATOM    639  N    ILE B  86      13.251  13.675 -11.958  0.00  0.00           N
ATOM    640  CA   ILE B  86      13.029  14.436 -13.194  0.00  0.00           C
ATOM    641  C    ILE B  86      13.188  13.514 -14.403  0.00  0.00           C
ATOM    642  O    ILE B  86      12.459  13.832 -15.364  0.00  0.00           O
ATOM    643  CB   ILE B  86      13.835  15.766 -13.399  0.00  0.00           C
ATOM    644  CG1  ILE B  86      14.953  15.542 -14.455  0.00  0.00           C
```

FIG. 1 (cont'd)

```
ATOM    645  CG2 ILE B  86      14.412  16.391 -12.115  0.00  0.00           C
ATOM    646  CD1 ILE B  86      15.271  16.841 -15.228  0.00  0.00           C
ATOM    647  N   GLU B  87      14.034  12.507 -14.423  0.00  0.00           N
ATOM    648  CA  GLU B  87      14.188  11.631 -15.597  0.00  0.00           C
ATOM    649  C   GLU B  87      12.893  10.874 -15.890  0.00  0.00           C
ATOM    650  O   GLU B  87      12.668  10.406 -17.028  0.00  0.00           O
ATOM    651  CB  GLU B  87      15.344  10.673 -15.565  0.00  0.00           C
ATOM    652  CG  GLU B  87      16.078  10.249 -14.329  0.00  0.00           C
ATOM    653  CD  GLU B  87      17.169  11.108 -13.768  0.00  0.00           C
ATOM    654  OE1 GLU B  87      16.979  11.942 -12.897  0.00  0.00           O
ATOM    655  OE2 GLU B  87      18.282  10.848 -14.292  0.00  0.00           O
ATOM    656  N   ASN B  88      12.064  10.682 -14.896  0.00  0.00           N
ATOM    657  CA  ASN B  88      10.758  10.035 -14.966  0.00  0.00           C
ATOM    658  C   ASN B  88       9.781  10.982 -15.686  0.00  0.00           C
ATOM    659  O   ASN B  88       9.155  10.662 -16.689  0.00  0.00           O
ATOM    660  CB  ASN B  88      10.187   9.704 -13.600  0.00  0.00           C
ATOM    661  CG  ASN B  88      10.444   8.508 -12.754  0.00  0.00           C
ATOM    662  OD1 ASN B  88      10.749   8.620 -11.557  0.00  0.00           O
ATOM    663  ND2 ASN B  88      10.309   7.270 -13.216  0.00  0.00           N
ATOM    664  N   TRP B  89       9.699  12.166 -15.108  0.00  0.00           N
ATOM    665  CA  TRP B  89       8.822  13.281 -15.509  0.00  0.00           C
ATOM    666  C   TRP B  89       9.197  13.845 -16.871  0.00  0.00           C
ATOM    667  O   TRP B  89       8.246  13.894 -17.690  0.00  0.00           O
ATOM    668  CB  TRP B  89       8.812  14.263 -14.352  0.00  0.00           C
ATOM    669  CG  TRP B  89       8.019  14.122 -13.114  0.00  0.00           C
ATOM    670  CD1 TRP B  89       8.509  14.091 -11.835  0.00  0.00           C
ATOM    671  CD2 TRP B  89       6.586  14.087 -12.976  0.00  0.00           C
ATOM    672  NE1 TRP B  89       7.477  14.033 -10.928  0.00  0.00           N
ATOM    673  CE2 TRP B  89       6.292  13.994 -11.599  0.00  0.00           C
ATOM    674  CE3 TRP B  89       5.533  14.074 -13.894  0.00  0.00           C
ATOM    675  CZ2 TRP B  89       4.994  13.875 -11.115  0.00  0.00           C
ATOM    676  CZ3 TRP B  89       4.231  13.965 -13.425  0.00  0.00           C
ATOM    677  CH2 TRP B  89       3.963  13.867 -12.043  0.00  0.00           C
ATOM    678  N   ILE B  90      10.417  14.147 -17.266  0.00  0.00           N
ATOM    679  CA  ILE B  90      10.741  14.656 -18.605  0.00  0.00           C
ATOM    680  C   ILE B  90      10.349  13.599 -19.652  0.00  0.00           C
ATOM    681  O   ILE B  90      10.243  13.799 -20.879  0.00  0.00           O
ATOM    682  CB  ILE B  90      12.197  15.204 -18.809  0.00  0.00           C
ATOM    683  CG1 ILE B  90      12.612  16.387 -17.898  0.00  0.00           C
ATOM    684  CG2 ILE B  90      12.463  15.635 -20.295  0.00  0.00           C
ATOM    685  CD1 ILE B  90      13.902  17.121 -18.382  0.00  0.00           C
ATOM    686  N   GLY B  91      10.223  12.365 -19.261  0.00  0.00           N
ATOM    687  CA  GLY B  91       9.834  11.151 -19.953  0.00  0.00           C
ATOM    688  C   GLY B  91       8.342  11.121 -20.268  0.00  0.00           C
ATOM    689  O   GLY B  91       7.936  10.507 -21.267  0.00  0.00           O
ATOM    690  N   ASN B  92       7.555  11.732 -19.395  0.00  0.00           N
ATOM    691  CA  ASN B  92       6.083  11.757 -19.545  0.00  0.00           C
ATOM    692  C   ASN B  92       5.732  12.655 -20.717  0.00  0.00           C
ATOM    693  O   ASN B  92       4.739  12.406 -21.407  0.00  0.00           O
ATOM    694  CB  ASN B  92       5.380  12.054 -18.225  0.00  0.00           C
ATOM    695  CG  ASN B  92       5.670  10.911 -17.238  0.00  0.00           C
ATOM    696  OD1 ASN B  92       6.208  11.222 -16.159  0.00  0.00           O
ATOM    697  ND2 ASN B  92       5.364   9.662 -17.590  0.00  0.00           N
ATOM    698  N   LEU B  93       6.566  13.653 -20.927  0.00  0.00           N
ATOM    699  CA  LEU B  93       6.402  14.610 -22.005  0.00  0.00           C
ATOM    700  C   LEU B  93       7.057  14.063 -23.255  0.00  0.00           C
ATOM    701  O   LEU B  93       7.692  14.870 -23.937  0.00  0.00           O
ATOM    702  CB  LEU B  93       7.011  15.964 -21.653  0.00  0.00           C
ATOM    703  CG  LEU B  93       7.296  16.324 -20.209  0.00  0.00           C
```

FIG. 1 (cont'd)

```
ATOM    704  CD1 LEU B  93       8.493  17.270 -20.139  0.00  0.00           C
ATOM    705  CD2 LEU B  93       6.065  16.988 -19.605  0.00  0.00           C
ATOM    706  N   ASN B  94       6.962  12.806 -23.559  0.00  0.00           N
ATOM    707  CA  ASN B  94       7.532  12.165 -24.743  0.00  0.00           C
ATOM    708  C   ASN B  94       6.353  11.529 -25.460  0.00  0.00           C
ATOM    709  O   ASN B  94       6.494  10.359 -25.788  0.00  0.00           O
ATOM    710  CB  ASN B  94       8.600  11.095 -24.454  0.00  0.00           C
ATOM    711  CG  ASN B  94       9.822  11.680 -25.162  0.00  0.00           C
ATOM    712  OD1 ASN B  94       9.550  12.170 -26.266  0.00  0.00           O
ATOM    713  ND2 ASN B  94      10.974  11.644 -24.546  0.00  0.00           N
ATOM    714  N   PHE B  95       5.298  12.302 -25.551  0.00  0.00           N
ATOM    715  CA  PHE B  95       4.020  11.861 -26.101  0.00  0.00           C
ATOM    716  C   PHE B  95       4.072  11.598 -27.600  0.00  0.00           C
ATOM    717  O   PHE B  95       2.899  11.286 -27.989  0.00  0.00           O
ATOM    718  CB  PHE B  95       2.851  12.786 -25.931  0.00  0.00           C
ATOM    719  CG  PHE B  95       2.172  13.645 -24.981  0.00  0.00           C
ATOM    720  CD1 PHE B  95       0.813  13.975 -25.158  0.00  0.00           C
ATOM    721  CD2 PHE B  95       2.840  14.230 -23.890  0.00  0.00           C
ATOM    722  CE1 PHE B  95       0.156  14.839 -24.268  0.00  0.00           C
ATOM    723  CE2 PHE B  95       2.202  15.103 -22.991  0.00  0.00           C
ATOM    724  CZ  PHE B  95       0.835  15.387 -23.176  0.00  0.00           C
ATOM    725  N   ASP B  96       5.100  11.656 -28.424  0.00  0.00           N
ATOM    726  CA  ASP B  96       4.637  11.319 -29.812  0.00  0.00           C
ATOM    727  C   ASP B  96       4.261   9.832 -29.643  0.00  0.00           C
ATOM    728  O   ASP B  96       4.550   9.218 -28.609  0.00  0.00           O
ATOM    729  CB  ASP B  96       5.486  11.670 -30.975  0.00  0.00           C
ATOM    730  CG  ASP B  96       6.977  11.485 -30.809  0.00  0.00           C
ATOM    731  OD1 ASP B  96       7.379  10.780 -29.865  0.00  0.00           O
ATOM    732  OD2 ASP B  96       7.620  12.106 -31.693  0.00  0.00           O
ATOM    733  N   LEU B  97       3.670   9.374 -30.729  0.00  0.00           N
ATOM    734  CA  LEU B  97       3.243   7.956 -30.695  0.00  0.00           C
ATOM    735  C   LEU B  97       4.299   7.299 -31.604  0.00  0.00           C
ATOM    736  O   LEU B  97       4.476   7.650 -32.763  0.00  0.00           O
ATOM    737  CB  LEU B  97       1.799   7.835 -31.089  0.00  0.00           C
ATOM    738  CG  LEU B  97       0.605   8.375 -30.358  0.00  0.00           C
ATOM    739  CD1 LEU B  97       0.473   9.880 -30.517  0.00  0.00           C
ATOM    740  CD2 LEU B  97      -0.611   7.687 -30.986  0.00  0.00           C
ATOM    741  N   LYS B  98       4.909   6.307 -30.988  0.00  0.00           N
ATOM    742  CA  LYS B  98       6.014   5.501 -31.539  0.00  0.00           C
ATOM    743  C   LYS B  98       5.284   4.210 -31.845  0.00  0.00           C
ATOM    744  O   LYS B  98       4.296   3.999 -31.127  0.00  0.00           O
ATOM    745  CB  LYS B  98       7.093   5.381 -30.537  0.00  0.00           C
ATOM    746  CG  LYS B  98       8.518   5.045 -30.928  0.00  0.00           C
ATOM    747  CD  LYS B  98       9.165   4.397 -29.701  0.00  0.00           C
ATOM    748  CE  LYS B  98      10.477   3.719 -30.000  0.00  0.00           C
ATOM    749  NZ  LYS B  98      11.491   4.692 -30.515  0.00  0.00           N
ATOM    750  N   GLU B  99       5.728   3.445 -32.805  0.00  0.00           N
ATOM    751  CA  GLU B  99       5.027   2.246 -33.282  0.00  0.00           C
ATOM    752  C   GLU B  99       5.326   0.959 -32.540  0.00  0.00           C
ATOM    753  O   GLU B  99       6.476   0.711 -32.147  0.00  0.00           O
ATOM    754  CB  GLU B  99       5.470   1.992 -34.745  0.00  0.00           C
ATOM    755  CG  GLU B  99       5.389   3.020 -35.872  0.00  0.00           C
ATOM    756  CD  GLU B  99       4.816   2.677 -37.224  0.00  0.00           C
ATOM    757  OE1 GLU B  99       3.707   2.216 -37.467  0.00  0.00           O
ATOM    758  OE2 GLU B  99       5.541   2.892 -38.230  0.00  0.00           O
ATOM    759  N   ILE B 100       4.309   0.155 -32.207  0.00  0.00           N
ATOM    760  CA  ILE B 100       4.517  -1.112 -31.496  0.00  0.00           C
ATOM    761  C   ILE B 100       3.560  -2.182 -32.010  0.00  0.00           C
ATOM    762  O   ILE B 100       2.751  -2.823 -31.308  0.00  0.00           O
```

FIG. 1 (cont'd)

```
ATOM    763  CB  ILE B 100       4.247  -0.891 -29.972  0.00  0.00           C
ATOM    764  CG1 ILE B 100       2.963  -0.025 -29.783  0.00  0.00           C
ATOM    765  CG2 ILE B 100       5.395  -0.263 -29.176  0.00  0.00           C
ATOM    766  CD1 ILE B 100       2.252  -0.419 -28.457  0.00  0.00           C
ATOM    767  N   ASN B 101       3.879  -2.569 -33.253  0.00  0.00           N
ATOM    768  CA  ASN B 101       3.072  -3.590 -33.977  0.00  0.00           C
ATOM    769  C   ASN B 101       3.747  -4.947 -33.799  0.00  0.00           C
ATOM    770  O   ASN B 101       3.528  -5.936 -34.465  0.00  0.00           O
ATOM    771  CB  ASN B 101       2.688  -3.165 -35.380  0.00  0.00           C
ATOM    772  CG  ASN B 101       3.747  -2.952 -36.413  0.00  0.00           C
ATOM    773  OD1 ASN B 101       4.257  -1.827 -36.555  0.00  0.00           O
ATOM    774  ND2 ASN B 101       4.073  -3.998 -37.177  0.00  0.00           N
ATOM    775  N   ASP B 102       4.525  -4.980 -32.776  0.00  0.00           N
ATOM    776  CA  ASP B 102       5.383  -5.871 -32.023  0.00  0.00           C
ATOM    777  C   ASP B 102       4.491  -6.281 -30.831  0.00  0.00           C
ATOM    778  O   ASP B 102       4.657  -7.367 -30.254  0.00  0.00           O
ATOM    779  CB  ASP B 102       6.679  -5.173 -31.738  0.00  0.00           C
ATOM    780  CG  ASP B 102       7.447  -5.164 -30.462  0.00  0.00           C
ATOM    781  OD1 ASP B 102       7.303  -5.987 -29.543  0.00  0.00           O
ATOM    782  OD2 ASP B 102       8.303  -4.236 -30.370  0.00  0.00           O
ATOM    783  N   ILE B 103       3.541  -5.403 -30.520  0.00  0.00           N
ATOM    784  CA  ILE B 103       2.589  -5.705 -29.458  0.00  0.00           C
ATOM    785  C   ILE B 103       1.301  -6.163 -30.160  0.00  0.00           C
ATOM    786  O   ILE B 103       0.755  -7.217 -29.816  0.00  0.00           O
ATOM    787  CB  ILE B 103       2.228  -4.583 -28.437  0.00  0.00           C
ATOM    788  CG1 ILE B 103       3.465  -4.393 -27.540  0.00  0.00           C
ATOM    789  CG2 ILE B 103       0.929  -4.904 -27.649  0.00  0.00           C
ATOM    790  CD1 ILE B 103       3.261  -3.840 -26.106  0.00  0.00           C
ATOM    791  N   CYS B 104       0.875  -5.286 -31.064  0.00  0.00           N
ATOM    792  CA  CYS B 104      -0.369  -5.638 -31.779  0.00  0.00           C
ATOM    793  C   CYS B 104      -0.377  -4.812 -33.054  0.00  0.00           C
ATOM    794  O   CYS B 104       0.272  -3.794 -33.196  0.00  0.00           O
ATOM    795  CB  CYS B 104      -1.617  -5.473 -30.952  0.00  0.00           C
ATOM    796  SG  CYS B 104      -1.567  -4.045 -29.846  0.00  0.00           S
ATOM    797  N   SER B 105      -1.171  -5.430 -33.907  0.00  0.00           N
ATOM    798  CA  SER B 105      -1.363  -4.900 -35.274  0.00  0.00           C
ATOM    799  C   SER B 105      -2.227  -3.658 -35.165  0.00  0.00           C
ATOM    800  O   SER B 105      -3.328  -3.733 -34.596  0.00  0.00           O
ATOM    801  CB  SER B 105      -1.929  -5.960 -36.205  0.00  0.00           C
ATOM    802  OG  SER B 105      -0.898  -6.803 -36.743  0.00  0.00           O
ATOM    803  N   GLY B 106      -1.657  -2.576 -35.677  0.00  0.00           N
ATOM    804  CA  GLY B 106      -2.441  -1.321 -35.639  0.00  0.00           C
ATOM    805  C   GLY B 106      -2.009  -0.448 -34.482  0.00  0.00           C
ATOM    806  O   GLY B 106      -1.971   0.774 -34.727  0.00  0.00           O
ATOM    807  N   CYS B 107      -1.701  -1.026 -33.345  0.00  0.00           N
ATOM    808  CA  CYS B 107      -1.275  -0.282 -32.155  0.00  0.00           C
ATOM    809  C   CYS B 107      -0.146   0.714 -32.375  0.00  0.00           C
ATOM    810  O   CYS B 107       0.567   0.706 -33.391  0.00  0.00           O
ATOM    811  CB  CYS B 107      -0.911  -1.358 -31.133  0.00  0.00           C
ATOM    812  SG  CYS B 107      -2.286  -2.530 -31.050  0.00  0.00           S
ATOM    813  N   ARG B 108      -0.086   1.634 -31.426  0.00  0.00           N
ATOM    814  CA  ARG B 108       0.866   2.755 -31.316  0.00  0.00           C
ATOM    815  C   ARG B 108       0.879   3.159 -29.834  0.00  0.00           C
ATOM    816  O   ARG B 108      -0.153   3.115 -29.141  0.00  0.00           O
ATOM    817  CB  ARG B 108       0.501   3.882 -32.239  0.00  0.00           C
ATOM    818  CG  ARG B 108       1.282   4.818 -33.106  0.00  0.00           C
ATOM    819  CD  ARG B 108       0.751   5.009 -34.499  0.00  0.00           C
ATOM    820  NE  ARG B 108       1.324   6.106 -35.244  0.00  0.00           N
ATOM    821  CZ  ARG B 108       1.249   7.392 -34.863  0.00  0.00           C
```

FIG. 1 (cont'd)

```
ATOM    822  NH1 ARG B 108       0.620   7.723 -33.735  0.00  0.00           N
ATOM    823  NH2 ARG B 108       1.773   8.443 -35.523  0.00  0.00           N
ATOM    824  N   GLY B 109       2.022   3.565 -29.343  0.00  0.00           N
ATOM    825  CA  GLY B 109       2.249   3.987 -27.978  0.00  0.00           C
ATOM    826  C   GLY B 109       3.064   5.244 -27.722  0.00  0.00           C
ATOM    827  O   GLY B 109       3.887   5.780 -28.480  0.00  0.00           O
ATOM    828  N   HIS B 110       2.930   5.644 -26.475  0.00  0.00           N
ATOM    829  CA  HIS B 110       3.560   6.869 -25.959  0.00  0.00           C
ATOM    830  C   HIS B 110       5.020   6.506 -25.846  0.00  0.00           C
ATOM    831  O   HIS B 110       5.480   5.645 -25.107  0.00  0.00           O
ATOM    832  CB  HIS B 110       2.875   7.196 -24.634  0.00  0.00           C
ATOM    833  CG  HIS B 110       3.506   8.313 -23.873  0.00  0.00           C
ATOM    834  ND1 HIS B 110       4.854   8.458 -23.657  0.00  0.00           N
ATOM    835  CD2 HIS B 110       2.884   9.348 -23.247  0.00  0.00           C
ATOM    836  CE1 HIS B 110       5.014   9.555 -22.930  0.00  0.00           C
ATOM    837  NE2 HIS B 110       3.849  10.117 -22.678  0.00  0.00           N
ATOM    838  N   ASP B 111       5.775   7.280 -26.629  0.00  0.00           N
ATOM    839  CA  ASP B 111       7.219   7.145 -26.855  0.00  0.00           C
ATOM    840  C   ASP B 111       7.992   6.875 -25.561  0.00  0.00           C
ATOM    841  O   ASP B 111       8.772   5.909 -25.543  0.00  0.00           O
ATOM    842  CB  ASP B 111       7.811   8.387 -27.534  0.00  0.00           C
ATOM    843  CG  ASP B 111       9.260   8.248 -27.962  0.00  0.00           C
ATOM    844  OD1 ASP B 111       9.736   9.084 -28.762  0.00  0.00           O
ATOM    845  OD2 ASP B 111       9.942   7.289 -27.517  0.00  0.00           O
ATOM    846  N   GLY B 112       7.732   7.709 -24.575  0.00  0.00           N
ATOM    847  CA  GLY B 112       8.387   7.574 -23.291  0.00  0.00           C
ATOM    848  C   GLY B 112       8.040   6.304 -22.545  0.00  0.00           C
ATOM    849  O   GLY B 112       8.863   5.922 -21.707  0.00  0.00           O
ATOM    850  N   PHE B 113       6.869   5.733 -22.661  0.00  0.00           N
ATOM    851  CA  PHE B 113       6.466   4.519 -21.913  0.00  0.00           C
ATOM    852  C   PHE B 113       6.999   3.283 -22.640  0.00  0.00           C
ATOM    853  O   PHE B 113       7.577   2.327 -22.128  0.00  0.00           O
ATOM    854  CB  PHE B 113       4.965   4.537 -21.664  0.00  0.00           C
ATOM    855  CG  PHE B 113       4.219   5.638 -21.010  0.00  0.00           C
ATOM    856  CD1 PHE B 113       4.787   6.641 -20.240  0.00  0.00           C
ATOM    857  CD2 PHE B 113       2.827   5.679 -21.136  0.00  0.00           C
ATOM    858  CE1 PHE B 113       4.017   7.631 -19.634  0.00  0.00           C
ATOM    859  CE2 PHE B 113       2.016   6.672 -20.558  0.00  0.00           C
ATOM    860  CZ  PHE B 113       2.635   7.667 -19.791  0.00  0.00           C
ATOM    861  N   THR B 114       6.790   3.328 -23.943  0.00  0.00           N
ATOM    862  CA  THR B 114       7.181   2.309 -24.897  0.00  0.00           C
ATOM    863  C   THR B 114       8.673   2.042 -24.831  0.00  0.00           C
ATOM    864  O   THR B 114       9.156   0.920 -24.665  0.00  0.00           O
ATOM    865  CB  THR B 114       6.832   2.804 -26.367  0.00  0.00           C
ATOM    866  OG1 THR B 114       5.397   2.588 -26.396  0.00  0.00           O
ATOM    867  CG2 THR B 114       7.645   2.110 -27.461  0.00  0.00           C
ATOM    868  N   SER B 115       9.372   3.153 -24.939  0.00  0.00           N
ATOM    869  CA  SER B 115      10.835   3.193 -24.941  0.00  0.00           C
ATOM    870  C   SER B 115      11.361   2.609 -23.630  0.00  0.00           C
ATOM    871  O   SER B 115      12.077   1.590 -23.619  0.00  0.00           O
ATOM    872  CB  SER B 115      11.240   4.639 -25.185  0.00  0.00           C
ATOM    873  OG  SER B 115      12.613   4.844 -24.973  0.00  0.00           O
ATOM    874  N   SER B 116      10.863   3.217 -22.550  0.00  0.00           N
ATOM    875  CA  SER B 116      11.223   2.818 -21.194  0.00  0.00           C
ATOM    876  C   SER B 116      10.824   1.360 -21.018  0.00  0.00           C
ATOM    877  O   SER B 116      11.520   0.608 -20.298  0.00  0.00           O
ATOM    878  CB  SER B 116      10.582   3.604 -20.075  0.00  0.00           C
ATOM    879  OG  SER B 116      11.426   4.672 -19.665  0.00  0.00           O
ATOM    880  N   TRP B 117       9.716   0.957 -21.619  0.00  0.00           N
```

FIG. 1 (cont'd)

```
ATOM    881  CA   TRP B 117       9.473  -0.468 -21.342  0.00  0.00           C
ATOM    882  C    TRP B 117      10.499  -1.349 -22.036  0.00  0.00           C
ATOM    883  O    TRP B 117      11.326  -2.034 -21.390  0.00  0.00           O
ATOM    884  CB   TRP B 117       8.011  -0.885 -21.576  0.00  0.00           C
ATOM    885  CG   TRP B 117       8.097  -2.055 -20.628  0.00  0.00           C
ATOM    886  CD1  TRP B 117       8.517  -2.032 -19.323  0.00  0.00           C
ATOM    887  CD2  TRP B 117       7.902  -3.411 -20.993  0.00  0.00           C
ATOM    888  NE1  TRP B 117       8.545  -3.312 -18.818  0.00  0.00           N
ATOM    889  CE2  TRP B 117       8.169  -4.169 -19.825  0.00  0.00           C
ATOM    890  CE3  TRP B 117       7.502  -4.025 -22.171  0.00  0.00           C
ATOM    891  CZ2  TRP B 117       8.050  -5.550 -19.791  0.00  0.00           C
ATOM    892  CZ3  TRP B 117       7.388  -5.394 -22.141  0.00  0.00           C
ATOM    893  CH2  TRP B 117       7.660  -6.133 -20.987  0.00  0.00           C
ATOM    894  N    ARG B 118      10.583  -1.191 -23.348  0.00  0.00           N
ATOM    895  CA   ARG B 118      11.500  -1.897 -24.227  0.00  0.00           C
ATOM    896  C    ARG B 118      12.913  -1.863 -23.659  0.00  0.00           C
ATOM    897  O    ARG B 118      13.740  -2.688 -24.052  0.00  0.00           O
ATOM    898  CB   ARG B 118      11.508  -1.257 -25.611  0.00  0.00           C
ATOM    899  CG   ARG B 118      10.871  -1.909 -26.828  0.00  0.00           C
ATOM    900  CD   ARG B 118      11.405  -1.415 -28.139  0.00  0.00           C
ATOM    901  NE   ARG B 118      12.713  -1.911 -28.518  0.00  0.00           N
ATOM    902  CZ   ARG B 118      13.751  -1.533 -29.255  0.00  0.00           C
ATOM    903  NH1  ARG B 118      13.884  -0.395 -29.948  0.00  0.00           N
ATOM    904  NH2  ARG B 118      14.794  -2.388 -29.313  0.00  0.00           N
ATOM    905  N    SER B 119      13.289  -0.895 -22.850  0.00  0.00           N
ATOM    906  CA   SER B 119      14.588  -0.645 -22.252  0.00  0.00           C
ATOM    907  C    SER B 119      15.001  -1.703 -21.259  0.00  0.00           C
ATOM    908  O    SER B 119      15.987  -2.414 -21.353  0.00  0.00           O
ATOM    909  CB   SER B 119      14.496   0.711 -21.546  0.00  0.00           C
ATOM    910  OG   SER B 119      13.872   0.426 -20.331  0.00  0.00           O
ATOM    911  N    VAL B 120      14.200  -1.869 -20.269  0.00  0.00           N
ATOM    912  CA   VAL B 120      14.195  -2.765 -19.122  0.00  0.00           C
ATOM    913  C    VAL B 120      13.612  -4.094 -19.551  0.00  0.00           C
ATOM    914  O    VAL B 120      12.865  -4.758 -18.812  0.00  0.00           O
ATOM    915  CB   VAL B 120      13.651  -1.975 -17.917  0.00  0.00           C
ATOM    916  CG1  VAL B 120      12.149  -1.786 -17.918  0.00  0.00           C
ATOM    917  CG2  VAL B 120      14.125  -2.577 -16.599  0.00  0.00           C
ATOM    918  N    ALA B 121      13.588  -4.465 -20.772  0.00  0.00           N
ATOM    919  CA   ALA B 121      13.237  -5.563 -21.616  0.00  0.00           C
ATOM    920  C    ALA B 121      13.253  -7.047 -21.241  0.00  0.00           C
ATOM    921  O    ALA B 121      12.419  -7.744 -20.647  0.00  0.00           O
ATOM    922  CB   ALA B 121      14.385  -5.395 -22.706  0.00  0.00           C
ATOM    923  N    ASP B 122      14.344  -7.644 -21.674  0.00  0.00           N
ATOM    924  CA   ASP B 122      14.972  -8.925 -21.667  0.00  0.00           C
ATOM    925  C    ASP B 122      15.158  -9.329 -20.207  0.00  0.00           C
ATOM    926  O    ASP B 122      14.757 -10.449 -19.848  0.00  0.00           O
ATOM    927  CB   ASP B 122      16.289  -8.808 -22.460  0.00  0.00           C
ATOM    928  CG   ASP B 122      16.108  -9.110 -23.944  0.00  0.00           C
ATOM    929  OD1  ASP B 122      16.559 -10.192 -24.377  0.00  0.00           O
ATOM    930  OD2  ASP B 122      15.517  -8.270 -24.663  0.00  0.00           O
ATOM    931  N    THR B 123      15.662  -8.447 -19.366  0.00  0.00           N
ATOM    932  CA   THR B 123      15.855  -8.681 -17.951  0.00  0.00           C
ATOM    933  C    THR B 123      14.565  -8.935 -17.190  0.00  0.00           C
ATOM    934  O    THR B 123      14.579  -9.948 -16.483  0.00  0.00           O
ATOM    935  CB   THR B 123      16.516  -7.423 -17.246  0.00  0.00           C
ATOM    936  OG1  THR B 123      17.713  -7.195 -18.046  0.00  0.00           O
ATOM    937  CG2  THR B 123      16.729  -7.619 -15.748  0.00  0.00           C
ATOM    938  N    LEU B 124      13.553  -8.087 -17.329  0.00  0.00           N
ATOM    939  CA   LEU B 124      12.277  -8.251 -16.593  0.00  0.00           C
```

FIG. 1 (cont'd)

```
ATOM    940  C    LEU B 124      11.521   -9.489  -17.049  0.00  0.00           C
ATOM    941  O    LEU B 124      10.805  -10.076  -16.230  0.00  0.00           O
ATOM    942  CB   LEU B 124      11.442   -6.984  -16.646  0.00  0.00           C
ATOM    943  CG   LEU B 124      11.733   -5.761  -15.799  0.00  0.00           C
ATOM    944  CD1  LEU B 124      10.775   -5.681  -14.611  0.00  0.00           C
ATOM    945  CD2  LEU B 124      13.192   -5.834  -15.350  0.00  0.00           C
ATOM    946  N    ARG B 125      11.647   -9.862  -18.292  0.00  0.00           N
ATOM    947  CA   ARG B 125      11.015  -11.069  -18.840  0.00  0.00           C
ATOM    948  C    ARG B 125      11.523  -12.336  -18.160  0.00  0.00           C
ATOM    949  O    ARG B 125      10.766  -13.279  -17.890  0.00  0.00           O
ATOM    950  CB   ARG B 125      11.335  -11.135  -20.331  0.00  0.00           C
ATOM    951  CG   ARG B 125      10.964  -12.381  -21.104  0.00  0.00           C
ATOM    952  CD   ARG B 125      10.609  -12.026  -22.492  0.00  0.00           C
ATOM    953  NE   ARG B 125       9.892  -13.001  -23.292  0.00  0.00           N
ATOM    954  CZ   ARG B 125       9.057  -12.619  -24.280  0.00  0.00           C
ATOM    955  NH1  ARG B 125       8.821  -11.321  -24.562  0.00  0.00           N
ATOM    956  NH2  ARG B 125       8.422  -13.540  -25.006  0.00  0.00           N
ATOM    957  N    GLN B 126      12.820  -12.400  -17.913  0.00  0.00           N
ATOM    958  CA   GLN B 126      13.607  -13.492  -17.331  0.00  0.00           C
ATOM    959  C    GLN B 126      13.487  -13.792  -15.856  0.00  0.00           C
ATOM    960  O    GLN B 126      13.277  -14.990  -15.581  0.00  0.00           O
ATOM    961  CB   GLN B 126      15.122  -13.281  -17.601  0.00  0.00           C
ATOM    962  CG   GLN B 126      16.075  -14.430  -17.413  0.00  0.00           C
ATOM    963  CD   GLN B 126      17.534  -14.074  -17.202  0.00  0.00           C
ATOM    964  OE1  GLN B 126      17.893  -13.504  -16.160  0.00  0.00           O
ATOM    965  NE2  GLN B 126      18.456  -14.378  -18.133  0.00  0.00           N
ATOM    966  N    LYS B 127      13.573  -12.872  -14.913  0.00  0.00           N
ATOM    967  CA   LYS B 127      13.458  -13.218  -13.473  0.00  0.00           C
ATOM    968  C    LYS B 127      12.091  -13.842  -13.200  0.00  0.00           C
ATOM    969  O    LYS B 127      11.831  -14.702  -12.358  0.00  0.00           O
ATOM    970  CB   LYS B 127      13.755  -12.023  -12.565  0.00  0.00           C
ATOM    971  CG   LYS B 127      15.124  -11.445  -12.889  0.00  0.00           C
ATOM    972  CD   LYS B 127      16.186  -11.196  -11.833  0.00  0.00           C
ATOM    973  CE   LYS B 127      17.551  -11.433  -12.458  0.00  0.00           C
ATOM    974  NZ   LYS B 127      18.672  -10.555  -12.111  0.00  0.00           N
ATOM    975  N    VAL B 128      11.124  -13.374  -13.952  0.00  0.00           N
ATOM    976  CA   VAL B 128       9.698  -13.648  -14.062  0.00  0.00           C
ATOM    977  C    VAL B 128       9.410  -15.043  -14.605  0.00  0.00           C
ATOM    978  O    VAL B 128       8.292  -15.554  -14.353  0.00  0.00           O
ATOM    979  CB   VAL B 128       9.030  -12.460  -14.821  0.00  0.00           C
ATOM    980  CG1  VAL B 128       7.523  -12.597  -15.019  0.00  0.00           C
ATOM    981  CG2  VAL B 128       9.358  -11.132  -14.120  0.00  0.00           C
ATOM    982  N    GLU B 129      10.306  -15.598  -15.401  0.00  0.00           N
ATOM    983  CA   GLU B 129      10.081  -16.997  -15.945  0.00  0.00           C
ATOM    984  C    GLU B 129      10.646  -17.903  -14.851  0.00  0.00           C
ATOM    985  O    GLU B 129      10.050  -18.866  -14.361  0.00  0.00           O
ATOM    986  CB   GLU B 129      10.539  -17.106  -17.350  0.00  0.00           C
ATOM    987  CG   GLU B 129      10.932  -17.938  -18.517  0.00  0.00           C
ATOM    988  CD   GLU B 129      10.822  -17.401  -19.931  0.00  0.00           C
ATOM    989  OE1  GLU B 129      10.350  -16.307  -20.268  0.00  0.00           O
ATOM    990  OE2  GLU B 129      11.268  -18.222  -20.787  0.00  0.00           O
ATOM    991  N    ASP B 130      11.796  -17.485  -14.325  0.00  0.00           N
ATOM    992  CA   ASP B 130      12.493  -18.139  -13.232  0.00  0.00           C
ATOM    993  C    ASP B 130      11.440  -18.107  -12.096  0.00  0.00           C
ATOM    994  O    ASP B 130      11.339  -19.144  -11.423  0.00  0.00           O
ATOM    995  CB   ASP B 130      13.755  -17.507  -12.697  0.00  0.00           C
ATOM    996  CG   ASP B 130      14.895  -17.325  -13.666  0.00  0.00           C
ATOM    997  OD1  ASP B 130      14.808  -17.666  -14.864  0.00  0.00           O
ATOM    998  OD2  ASP B 130      15.903  -16.814  -13.110  0.00  0.00           O
```

FIG. 1 (cont'd)

```
ATOM    999  N   ALA B 131      10.772 -16.967 -11.966  0.00  0.00           N
ATOM   1000  CA  ALA B 131       9.784 -16.831 -10.900  0.00  0.00           C
ATOM   1001  C   ALA B 131       8.613 -17.792 -11.056  0.00  0.00           C
ATOM   1002  O   ALA B 131       8.260 -18.365 -10.007  0.00  0.00           O
ATOM   1003  CB  ALA B 131       9.246 -15.409 -10.778  0.00  0.00           C
ATOM   1004  N   VAL B 132       8.045 -17.918 -12.239  0.00  0.00           N
ATOM   1005  CA  VAL B 132       6.865 -18.823 -12.347  0.00  0.00           C
ATOM   1006  C   VAL B 132       7.198 -20.290 -12.493  0.00  0.00           C
ATOM   1007  O   VAL B 132       6.382 -21.101 -11.975  0.00  0.00           O
ATOM   1008  CB  VAL B 132       5.850 -18.268 -13.360  0.00  0.00           C
ATOM   1009  CG1 VAL B 132       4.713 -19.235 -13.650  0.00  0.00           C
ATOM   1010  CG2 VAL B 132       5.334 -16.941 -12.806  0.00  0.00           C
ATOM   1011  N   ARG B 133       8.309 -20.650 -13.118  0.00  0.00           N
ATOM   1012  CA  ARG B 133       8.637 -22.095 -13.181  0.00  0.00           C
ATOM   1013  C   ARG B 133       8.658 -22.621 -11.732  0.00  0.00           C
ATOM   1014  O   ARG B 133       7.875 -23.542 -11.473  0.00  0.00           O
ATOM   1015  CB  ARG B 133       9.987 -22.431 -13.710  0.00  0.00           C
ATOM   1016  CG  ARG B 133      10.463 -22.071 -15.114  0.00  0.00           C
ATOM   1017  CD  ARG B 133      11.731 -22.884 -15.295  0.00  0.00           C
ATOM   1018  NE  ARG B 133      12.327 -22.936 -13.951  0.00  0.00           N
ATOM   1019  CZ  ARG B 133      13.467 -22.403 -13.574  0.00  0.00           C
ATOM   1020  NH1 ARG B 133      14.289 -21.765 -14.402  0.00  0.00           N
ATOM   1021  NH2 ARG B 133      13.791 -22.527 -12.295  0.00  0.00           N
ATOM   1022  N   GLU B 134       9.422 -21.968 -10.855  0.00  0.00           N
ATOM   1023  CA  GLU B 134       9.426 -22.454  -9.478  0.00  0.00           C
ATOM   1024  C   GLU B 134       8.030 -22.548  -8.865  0.00  0.00           C
ATOM   1025  O   GLU B 134       7.778 -23.606  -8.217  0.00  0.00           O
ATOM   1026  CB  GLU B 134      10.136 -21.589  -8.448  0.00  0.00           C
ATOM   1027  CG  GLU B 134      11.043 -20.501  -9.014  0.00  0.00           C
ATOM   1028  CD  GLU B 134      12.486 -20.839  -8.720  0.00  0.00           C
ATOM   1029  OE1 GLU B 134      12.683 -21.541  -7.737  0.00  0.00           O
ATOM   1030  OE2 GLU B 134      13.247 -20.332  -9.557  0.00  0.00           O
ATOM   1031  N   HIS B 135       7.210 -21.499  -9.013  0.00  0.00           N
ATOM   1032  CA  HIS B 135       5.872 -21.568  -8.390  0.00  0.00           C
ATOM   1033  C   HIS B 135       4.674 -21.407  -9.297  0.00  0.00           C
ATOM   1034  O   HIS B 135       3.951 -20.386  -9.236  0.00  0.00           O
ATOM   1035  CB  HIS B 135       5.724 -20.493  -7.284  0.00  0.00           C
ATOM   1036  CG  HIS B 135       6.922 -20.273  -6.439  0.00  0.00           C
ATOM   1037  ND1 HIS B 135       6.958 -20.400  -5.070  0.00  0.00           N
ATOM   1038  CD2 HIS B 135       8.171 -19.898  -6.793  0.00  0.00           C
ATOM   1039  CE1 HIS B 135       8.194 -20.140  -4.645  0.00  0.00           C
ATOM   1040  NE2 HIS B 135       8.957 -19.848  -5.690  0.00  0.00           N
ATOM   1041  N   PRO B 136       4.356 -22.395 -10.131  0.00  0.00           N
ATOM   1042  CA  PRO B 136       3.201 -22.337 -11.035  0.00  0.00           C
ATOM   1043  C   PRO B 136       1.851 -22.566 -10.366  0.00  0.00           C
ATOM   1044  O   PRO B 136       0.894 -22.895 -11.128  0.00  0.00           O
ATOM   1045  CB  PRO B 136       3.463 -23.373 -12.136  0.00  0.00           C
ATOM   1046  CG  PRO B 136       4.777 -24.005 -11.802  0.00  0.00           C
ATOM   1047  CD  PRO B 136       5.069 -23.668 -10.334  0.00  0.00           C
ATOM   1048  N   ASP B 137       1.709 -22.402  -9.053  0.00  0.00           N
ATOM   1049  CA  ASP B 137       0.342 -22.613  -8.500  0.00  0.00           C
ATOM   1050  C   ASP B 137      -0.195 -21.194  -8.235  0.00  0.00           C
ATOM   1051  O   ASP B 137      -1.367 -20.976  -7.915  0.00  0.00           O
ATOM   1052  CB  ASP B 137       0.248 -23.615  -7.385  0.00  0.00           C
ATOM   1053  CG  ASP B 137       1.268 -23.781  -6.288  0.00  0.00           C
ATOM   1054  OD1 ASP B 137       2.495 -23.713  -6.526  0.00  0.00           O
ATOM   1055  OD2 ASP B 137       0.746 -23.998  -5.152  0.00  0.00           O
ATOM   1056  N   TYR B 138       0.717 -20.279  -8.425  0.00  0.00           N
ATOM   1057  CA  TYR B 138       0.667 -18.838  -8.272  0.00  0.00           C
```

FIG. 1 (cont'd)

```
ATOM   1058  C    TYR B 138       0.152 -18.017  -9.449  0.00  0.00           C
ATOM   1059  O    TYR B 138       0.467 -18.231 -10.641  0.00  0.00           O
ATOM   1060  CB   TYR B 138       2.139 -18.442  -7.969  0.00  0.00           C
ATOM   1061  CG   TYR B 138       2.621 -18.623  -6.554  0.00  0.00           C
ATOM   1062  CD1  TYR B 138       1.892 -19.283  -5.565  0.00  0.00           C
ATOM   1063  CD2  TYR B 138       3.871 -18.116  -6.187  0.00  0.00           C
ATOM   1064  CE1  TYR B 138       2.375 -19.400  -4.264  0.00  0.00           C
ATOM   1065  CE2  TYR B 138       4.363 -18.247  -4.887  0.00  0.00           C
ATOM   1066  CZ   TYR B 138       3.609 -18.871  -3.908  0.00  0.00           C
ATOM   1067  OH   TYR B 138       4.111 -18.945  -2.638  0.00  0.00           O
ATOM   1068  N    ARG B 139      -0.583 -16.986  -9.050  0.00  0.00           N
ATOM   1069  CA   ARG B 139      -1.220 -15.962  -9.876  0.00  0.00           C
ATOM   1070  C    ARG B 139      -0.200 -14.800  -9.917  0.00  0.00           C
ATOM   1071  O    ARG B 139       0.105 -14.247  -8.854  0.00  0.00           O
ATOM   1072  CB   ARG B 139      -2.481 -15.284  -9.341  0.00  0.00           C
ATOM   1073  CG   ARG B 139      -3.575 -14.969 -10.332  0.00  0.00           C
ATOM   1074  CD   ARG B 139      -4.168 -13.620 -10.392  0.00  0.00           C
ATOM   1075  NE   ARG B 139      -5.116 -13.253  -9.346  0.00  0.00           N
ATOM   1076  CZ   ARG B 139      -5.758 -12.068  -9.358  0.00  0.00           C
ATOM   1077  NH1  ARG B 139      -5.597 -11.141 -10.303  0.00  0.00           N
ATOM   1078  NH2  ARG B 139      -6.582 -11.883  -8.334  0.00  0.00           N
ATOM   1079  N    VAL B 140       0.233 -14.487 -11.106  0.00  0.00           N
ATOM   1080  CA   VAL B 140       1.227 -13.408 -11.285  0.00  0.00           C
ATOM   1081  C    VAL B 140       0.397 -12.152 -11.562  0.00  0.00           C
ATOM   1082  O    VAL B 140      -0.437 -12.267 -12.479  0.00  0.00           O
ATOM   1083  CB   VAL B 140       2.284 -13.797 -12.340  0.00  0.00           C
ATOM   1084  CG1  VAL B 140       2.238 -15.265 -12.792  0.00  0.00           C
ATOM   1085  CG2  VAL B 140       2.344 -12.904 -13.577  0.00  0.00           C
ATOM   1086  N    VAL B 141       0.546 -11.108 -10.758  0.00  0.00           N
ATOM   1087  CA   VAL B 141      -0.201  -9.849 -10.896  0.00  0.00           C
ATOM   1088  C    VAL B 141       0.702  -8.635 -11.174  0.00  0.00           C
ATOM   1089  O    VAL B 141       1.613  -8.414 -10.363  0.00  0.00           O
ATOM   1090  CB   VAL B 141      -1.092  -9.478  -9.694  0.00  0.00           C
ATOM   1091  CG1  VAL B 141      -2.078  -8.369 -10.092  0.00  0.00           C
ATOM   1092  CG2  VAL B 141      -1.796 -10.674  -9.116  0.00  0.00           C
ATOM   1093  N    PHE B 142       0.413  -7.870 -12.209  0.00  0.00           N
ATOM   1094  CA   PHE B 142       1.262  -6.683 -12.540  0.00  0.00           C
ATOM   1095  C    PHE B 142       0.644  -5.392 -12.037  0.00  0.00           C
ATOM   1096  O    PHE B 142      -0.462  -5.034 -12.434  0.00  0.00           O
ATOM   1097  CB   PHE B 142       1.530  -6.719 -14.040  0.00  0.00           C
ATOM   1098  CG   PHE B 142       2.630  -7.626 -14.500  0.00  0.00           C
ATOM   1099  CD1  PHE B 142       3.368  -8.396 -13.582  0.00  0.00           C
ATOM   1100  CD2  PHE B 142       2.922  -7.735 -15.866  0.00  0.00           C
ATOM   1101  CE1  PHE B 142       4.376  -9.254 -14.005  0.00  0.00           C
ATOM   1102  CE2  PHE B 142       3.927  -8.599 -16.318  0.00  0.00           C
ATOM   1103  CZ   PHE B 142       4.653  -9.353 -15.376  0.00  0.00           C
ATOM   1104  N    THR B 143       1.328  -4.706 -11.139  0.00  0.00           N
ATOM   1105  CA   THR B 143       0.833  -3.478 -10.487  0.00  0.00           C
ATOM   1106  C    THR B 143       1.675  -2.211 -10.657  0.00  0.00           C
ATOM   1107  O    THR B 143       2.841  -2.236 -11.118  0.00  0.00           O
ATOM   1108  CB   THR B 143       0.441  -3.731  -8.968  0.00  0.00           C
ATOM   1109  OG1  THR B 143      -0.698  -2.821  -8.720  0.00  0.00           O
ATOM   1110  CG2  THR B 143       1.531  -3.499  -7.936  0.00  0.00           C
ATOM   1111  N    GLY B 144       0.944  -1.090 -10.555  0.00  0.00           N
ATOM   1112  CA   GLY B 144       1.539   0.222 -10.715  0.00  0.00           C
ATOM   1113  C    GLY B 144       0.709   1.447 -10.523  0.00  0.00           C
ATOM   1114  O    GLY B 144      -0.346   1.497 -11.189  0.00  0.00           O
ATOM   1115  N    HIS B 145       1.147   2.465  -9.848  0.00  0.00           N
ATOM   1116  CA   HIS B 145       0.368   3.711  -9.752  0.00  0.00           C
```

FIG. 1 (cont'd)

```
ATOM   1117  C   HIS B 145       0.820   4.669 -10.860  0.00  0.00           C
ATOM   1118  O   HIS B 145       2.040   4.800 -11.106  0.00  0.00           O
ATOM   1119  CB  HIS B 145       0.567   4.508  -8.477  0.00  0.00           C
ATOM   1120  CG  HIS B 145       0.332   5.958  -8.315  0.00  0.00           C
ATOM   1121  ND1 HIS B 145       1.317   6.837  -7.940  0.00  0.00           N
ATOM   1122  CD2 HIS B 145      -0.793   6.720  -8.391  0.00  0.00           C
ATOM   1123  CE1 HIS B 145       0.819   8.059  -7.818  0.00  0.00           C
ATOM   1124  NE2 HIS B 145      -0.462   8.022  -8.102  0.00  0.00           N
ATOM   1125  N   SER B 146      -0.150   5.260 -11.534  0.00  0.00           N
ATOM   1126  CA  SER B 146       0.140   6.293 -12.546  0.00  0.00           C
ATOM   1127  C   SER B 146       1.170   5.951 -13.595  0.00  0.00           C
ATOM   1128  O   SER B 146       0.839   5.205 -14.530  0.00  0.00           O
ATOM   1129  CB  SER B 146       0.554   7.570 -11.761  0.00  0.00           C
ATOM   1130  OG  SER B 146       1.403   8.471 -12.379  0.00  0.00           O
ATOM   1131  N   LEU B 147       2.398   6.477 -13.458  0.00  0.00           N
ATOM   1132  CA  LEU B 147       3.441   6.191 -14.456  0.00  0.00           C
ATOM   1133  C   LEU B 147       3.561   4.664 -14.471  0.00  0.00           C
ATOM   1134  O   LEU B 147       3.487   4.139 -15.603  0.00  0.00           O
ATOM   1135  CB  LEU B 147       4.727   6.925 -14.174  0.00  0.00           C
ATOM   1136  CG  LEU B 147       5.810   7.093 -15.227  0.00  0.00           C
ATOM   1137  CD1 LEU B 147       7.185   6.801 -14.613  0.00  0.00           C
ATOM   1138  CD2 LEU B 147       5.621   6.186 -16.435  0.00  0.00           C
ATOM   1139  N   GLY B 148       3.640   4.035 -13.304  0.00  0.00           N
ATOM   1140  CA  GLY B 148       3.716   2.574 -13.248  0.00  0.00           C
ATOM   1141  C   GLY B 148       2.589   1.739 -13.832  0.00  0.00           C
ATOM   1142  O   GLY B 148       2.850   0.615 -14.311  0.00  0.00           O
ATOM   1143  N   GLY B 149       1.351   2.160 -13.752  0.00  0.00           N
ATOM   1144  CA  GLY B 149       0.136   1.531 -14.252  0.00  0.00           C
ATOM   1145  C   GLY B 149       0.182   1.569 -15.781  0.00  0.00           C
ATOM   1146  O   GLY B 149      -0.259   0.696 -16.532  0.00  0.00           O
ATOM   1147  N   ALA B 150       0.740   2.677 -16.219  0.00  0.00           N
ATOM   1148  CA  ALA B 150       1.004   3.001 -17.625  0.00  0.00           C
ATOM   1149  C   ALA B 150       2.106   2.032 -18.025  0.00  0.00           C
ATOM   1150  O   ALA B 150       1.975   1.362 -19.062  0.00  0.00           O
ATOM   1151  CB  ALA B 150       1.286   4.467 -17.630  0.00  0.00           C
ATOM   1152  N   LEU B 151       3.142   1.840 -17.229  0.00  0.00           N
ATOM   1153  CA  LEU B 151       4.250   0.904 -17.451  0.00  0.00           C
ATOM   1154  C   LEU B 151       3.858  -0.575 -17.366  0.00  0.00           C
ATOM   1155  O   LEU B 151       4.145  -1.456 -18.210  0.00  0.00           O
ATOM   1156  CB  LEU B 151       5.376   1.243 -16.441  0.00  0.00           C
ATOM   1157  CG  LEU B 151       6.601   1.872 -17.096  0.00  0.00           C
ATOM   1158  CD1 LEU B 151       7.655   2.384 -16.126  0.00  0.00           C
ATOM   1159  CD2 LEU B 151       7.174   0.766 -17.989  0.00  0.00           C
ATOM   1160  N   ALA B 152       3.115  -0.826 -16.292  0.00  0.00           N
ATOM   1161  CA  ALA B 152       2.573  -2.146 -15.939  0.00  0.00           C
ATOM   1162  C   ALA B 152       1.680  -2.689 -17.053  0.00  0.00           C
ATOM   1163  O   ALA B 152       1.819  -3.834 -17.510  0.00  0.00           O
ATOM   1164  CB  ALA B 152       1.802  -2.036 -14.632  0.00  0.00           C
ATOM   1165  N   THR B 153       0.790  -1.859 -17.556  0.00  0.00           N
ATOM   1166  CA  THR B 153      -0.082  -2.224 -18.665  0.00  0.00           C
ATOM   1167  C   THR B 153       0.749  -2.631 -19.885  0.00  0.00           C
ATOM   1168  O   THR B 153       0.548  -3.753 -20.398  0.00  0.00           O
ATOM   1169  CB  THR B 153      -1.072  -1.069 -19.140  0.00  0.00           C
ATOM   1170  OG1 THR B 153      -0.218   0.123 -19.244  0.00  0.00           O
ATOM   1171  CG2 THR B 153      -2.292  -0.670 -18.295  0.00  0.00           C
ATOM   1172  N   VAL B 154       1.685  -1.794 -20.328  0.00  0.00           N
ATOM   1173  CA  VAL B 154       2.459  -2.092 -21.560  0.00  0.00           C
ATOM   1174  C   VAL B 154       3.340  -3.350 -21.465  0.00  0.00           C
ATOM   1175  O   VAL B 154       3.642  -4.091 -22.405  0.00  0.00           O
```

FIG. 1 (cont'd)

```
ATOM   1176  CB  VAL B 154       3.299  -0.905 -22.098  0.00  0.00           C
ATOM   1177  CG1 VAL B 154       2.798   0.471 -21.706  0.00  0.00           C
ATOM   1178  CG2 VAL B 154       4.785  -1.077 -21.767  0.00  0.00           C
ATOM   1179  N   ALA B 155       3.796  -3.516 -20.237  0.00  0.00           N
ATOM   1180  CA  ALA B 155       4.629  -4.644 -19.838  0.00  0.00           C
ATOM   1181  C   ALA B 155       3.738  -5.841 -20.072  0.00  0.00           C
ATOM   1182  O   ALA B 155       4.080  -6.898 -20.607  0.00  0.00           O
ATOM   1183  CB  ALA B 155       4.958  -4.280 -18.410  0.00  0.00           C
ATOM   1184  N   GLY B 156       2.482  -5.680 -19.680  0.00  0.00           N
ATOM   1185  CA  GLY B 156       1.372  -6.623 -19.759  0.00  0.00           C
ATOM   1186  C   GLY B 156       1.042  -6.981 -21.201  0.00  0.00           C
ATOM   1187  O   GLY B 156       0.679  -8.144 -21.409  0.00  0.00           O
ATOM   1188  N   ALA B 157       1.155  -6.017 -22.103  0.00  0.00           N
ATOM   1189  CA  ALA B 157       0.843  -6.308 -23.518  0.00  0.00           C
ATOM   1190  C   ALA B 157       1.821  -7.282 -24.171  0.00  0.00           C
ATOM   1191  O   ALA B 157       1.372  -8.239 -24.839  0.00  0.00           O
ATOM   1192  CB  ALA B 157       0.713  -4.980 -24.264  0.00  0.00           C
ATOM   1193  N   ASP B 158       3.109  -7.086 -23.999  0.00  0.00           N
ATOM   1194  CA  ASP B 158       4.164  -7.917 -24.549  0.00  0.00           C
ATOM   1195  C   ASP B 158       4.295  -9.299 -23.920  0.00  0.00           C
ATOM   1196  O   ASP B 158       4.951 -10.157 -24.546  0.00  0.00           O
ATOM   1197  CB  ASP B 158       5.575  -7.274 -24.444  0.00  0.00           C
ATOM   1198  CG  ASP B 158       6.439  -7.713 -25.621  0.00  0.00           C
ATOM   1199  OD1 ASP B 158       6.725  -8.885 -25.938  0.00  0.00           O
ATOM   1200  OD2 ASP B 158       6.859  -6.753 -26.324  0.00  0.00           O
ATOM   1201  N   LEU B 159       3.987  -9.527 -22.676  0.00  0.00           N
ATOM   1202  CA  LEU B 159       4.191 -10.798 -21.977  0.00  0.00           C
ATOM   1203  C   LEU B 159       3.049 -11.776 -21.905  0.00  0.00           C
ATOM   1204  O   LEU B 159       3.210 -12.952 -21.545  0.00  0.00           O
ATOM   1205  CB  LEU B 159       4.700 -10.323 -20.596  0.00  0.00           C
ATOM   1206  CG  LEU B 159       6.026  -9.593 -20.771  0.00  0.00           C
ATOM   1207  CD1 LEU B 159       6.660  -9.461 -19.387  0.00  0.00           C
ATOM   1208  CD2 LEU B 159       6.969 -10.284 -21.750  0.00  0.00           C
ATOM   1209  N   ARG B 160       1.913 -11.139 -22.107  0.00  0.00           N
ATOM   1210  CA  ARG B 160       0.607 -11.796 -22.022  0.00  0.00           C
ATOM   1211  C   ARG B 160       0.693 -13.089 -22.799  0.00  0.00           C
ATOM   1212  O   ARG B 160       1.453 -13.191 -23.768  0.00  0.00           O
ATOM   1213  CB  ARG B 160      -0.526 -10.882 -22.494  0.00  0.00           C
ATOM   1214  CG  ARG B 160      -1.621 -10.827 -21.431  0.00  0.00           C
ATOM   1215  CD  ARG B 160      -1.872  -9.421 -21.038  0.00  0.00           C
ATOM   1216  NE  ARG B 160      -2.767  -9.301 -19.900  0.00  0.00           N
ATOM   1217  CZ  ARG B 160      -4.048  -8.947 -20.013  0.00  0.00           C
ATOM   1218  NH1 ARG B 160      -4.584  -8.687 -21.201  0.00  0.00           N
ATOM   1219  NH2 ARG B 160      -4.773  -8.864 -18.913  0.00  0.00           N
ATOM   1220  N   GLY B 161      -0.050 -14.047 -22.299  0.00  0.00           N
ATOM   1221  CA  GLY B 161      -0.179 -15.397 -22.848  0.00  0.00           C
ATOM   1222  C   GLY B 161       1.001 -16.043 -23.539  0.00  0.00           C
ATOM   1223  O   GLY B 161       0.973 -16.732 -24.577  0.00  0.00           O
ATOM   1224  N   ASN B 162       2.125 -15.874 -22.868  0.00  0.00           N
ATOM   1225  CA  ASN B 162       3.443 -16.406 -23.255  0.00  0.00           C
ATOM   1226  C   ASN B 162       3.527 -17.743 -22.491  0.00  0.00           C
ATOM   1227  O   ASN B 162       4.613 -18.324 -22.380  0.00  0.00           O
ATOM   1228  CB  ASN B 162       4.521 -15.396 -22.980  0.00  0.00           C
ATOM   1229  CG  ASN B 162       5.410 -14.752 -24.012  0.00  0.00           C
ATOM   1230  OD1 ASN B 162       6.478 -15.330 -24.311  0.00  0.00           O
ATOM   1231  ND2 ASN B 162       5.090 -13.567 -24.554  0.00  0.00           N
ATOM   1232  N   GLY B 163       2.421 -18.222 -21.955  0.00  0.00           N
ATOM   1233  CA  GLY B 163       2.200 -19.450 -21.229  0.00  0.00           C
ATOM   1234  C   GLY B 163       1.469 -19.136 -19.929  0.00  0.00           C
```

FIG. 1 (cont'd)

```
ATOM   1235  O    GLY B 163       0.716 -19.905 -19.331  0.00  0.00           O
ATOM   1236  N    TYR B 164       1.734 -17.913 -19.518  0.00  0.00           N
ATOM   1237  CA   TYR B 164       1.315 -17.205 -18.311  0.00  0.00           C
ATOM   1238  C    TYR B 164       0.233 -16.136 -18.532  0.00  0.00           C
ATOM   1239  O    TYR B 164       0.244 -15.266 -19.421  0.00  0.00           O
ATOM   1240  CB   TYR B 164       2.560 -16.605 -17.578  0.00  0.00           C
ATOM   1241  CG   TYR B 164       3.881 -16.376 -18.263  0.00  0.00           C
ATOM   1242  CD1  TYR B 164       4.528 -17.410 -18.966  0.00  0.00           C
ATOM   1243  CD2  TYR B 164       4.574 -15.160 -18.227  0.00  0.00           C
ATOM   1244  CE1  TYR B 164       5.749 -17.272 -19.623  0.00  0.00           C
ATOM   1245  CE2  TYR B 164       5.805 -14.978 -18.867  0.00  0.00           C
ATOM   1246  CZ   TYR B 164       6.400 -16.030 -19.574  0.00  0.00           C
ATOM   1247  OH   TYR B 164       7.615 -15.858 -20.209  0.00  0.00           O
ATOM   1248  N    ASP B 165      -0.734 -16.264 -17.635  0.00  0.00           N
ATOM   1249  CA   ASP B 165      -1.924 -15.444 -17.458  0.00  0.00           C
ATOM   1250  C    ASP B 165      -1.593 -14.237 -16.549  0.00  0.00           C
ATOM   1251  O    ASP B 165      -1.359 -14.398 -15.331  0.00  0.00           O
ATOM   1252  CB   ASP B 165      -3.044 -16.196 -16.795  0.00  0.00           C
ATOM   1253  CG   ASP B 165      -4.301 -16.609 -17.490  0.00  0.00           C
ATOM   1254  OD1  ASP B 165      -5.360 -16.119 -17.034  0.00  0.00           O
ATOM   1255  OD2  ASP B 165      -4.193 -17.425 -18.441  0.00  0.00           O
ATOM   1256  N    ILE B 166      -1.634 -13.057 -17.172  0.00  0.00           N
ATOM   1257  CA   ILE B 166      -1.340 -11.824 -16.439  0.00  0.00           C
ATOM   1258  C    ILE B 166      -2.519 -10.863 -16.301  0.00  0.00           C
ATOM   1259  O    ILE B 166      -3.024 -10.105 -17.117  0.00  0.00           O
ATOM   1260  CB   ILE B 166      -0.082 -11.066 -17.018  0.00  0.00           C
ATOM   1261  CG1  ILE B 166       1.094 -12.035 -17.262  0.00  0.00           C
ATOM   1262  CG2  ILE B 166       0.314  -9.885 -16.094  0.00  0.00           C
ATOM   1263  CD1  ILE B 166       2.226 -11.529 -18.195  0.00  0.00           C
ATOM   1264  N    ASP B 167      -2.885 -10.791 -15.055  0.00  0.00           N
ATOM   1265  CA   ASP B 167      -3.895 -10.013 -14.373  0.00  0.00           C
ATOM   1266  C    ASP B 167      -3.036  -8.783 -13.990  0.00  0.00           C
ATOM   1267  O    ASP B 167      -1.915  -8.936 -13.451  0.00  0.00           O
ATOM   1268  CB   ASP B 167      -4.457 -10.782 -13.187  0.00  0.00           C
ATOM   1269  CG   ASP B 167      -5.771 -11.480 -13.467  0.00  0.00           C
ATOM   1270  OD1  ASP B 167      -6.571 -11.624 -12.533  0.00  0.00           O
ATOM   1271  OD2  ASP B 167      -5.952 -11.827 -14.655  0.00  0.00           O
ATOM   1272  N    VAL B 168      -3.520  -7.623 -14.392  0.00  0.00           N
ATOM   1273  CA   VAL B 168      -2.856  -6.333 -14.146  0.00  0.00           C
ATOM   1274  C    VAL B 168      -3.765  -5.360 -13.417  0.00  0.00           C
ATOM   1275  O    VAL B 168      -4.945  -5.329 -13.818  0.00  0.00           O
ATOM   1276  CB   VAL B 168      -2.366  -5.716 -15.470  0.00  0.00           C
ATOM   1277  CG1  VAL B 168      -1.296  -6.466 -16.243  0.00  0.00           C
ATOM   1278  CG2  VAL B 168      -3.539  -5.494 -16.424  0.00  0.00           C
ATOM   1279  N    PHE B 169      -3.391  -4.638 -12.392  0.00  0.00           N
ATOM   1280  CA   PHE B 169      -4.217  -3.659 -11.669  0.00  0.00           C
ATOM   1281  C    PHE B 169      -3.606  -2.253 -11.762  0.00  0.00           C
ATOM   1282  O    PHE B 169      -2.526  -2.094 -11.146  0.00  0.00           O
ATOM   1283  CB   PHE B 169      -4.361  -3.942 -10.187  0.00  0.00           C
ATOM   1284  CG   PHE B 169      -5.213  -5.117  -9.853  0.00  0.00           C
ATOM   1285  CD1  PHE B 169      -6.391  -4.896  -9.126  0.00  0.00           C
ATOM   1286  CD2  PHE B 169      -4.823  -6.404 -10.246  0.00  0.00           C
ATOM   1287  CE1  PHE B 169      -7.209  -5.963  -8.795  0.00  0.00           C
ATOM   1288  CE2  PHE B 169      -5.630  -7.497  -9.930  0.00  0.00           C
ATOM   1289  CZ   PHE B 169      -6.817  -7.242  -9.203  0.00  0.00           C
ATOM   1290  N    SER B 170      -4.276  -1.328 -12.433  0.00  0.00           N
ATOM   1291  CA   SER B 170      -3.649   0.004 -12.533  0.00  0.00           C
ATOM   1292  C    SER B 170      -4.511   1.075 -11.891  0.00  0.00           C
ATOM   1293  O    SER B 170      -5.733   1.049 -11.974  0.00  0.00           O
```

FIG. 1 (cont'd)

```
ATOM   1294  CB  SER B 170      -3.246   0.400 -13.929  0.00  0.00           C
ATOM   1295  OG  SER B 170      -4.315   0.458 -14.813  0.00  0.00           O
ATOM   1296  N   TYR B 171      -3.747   1.919 -11.205  0.00  0.00           N
ATOM   1297  CA  TYR B 171      -4.224   3.063 -10.443  0.00  0.00           C
ATOM   1298  C   TYR B 171      -3.779   4.433 -10.954  0.00  0.00           C
ATOM   1299  O   TYR B 171      -2.567   4.714 -11.032  0.00  0.00           O
ATOM   1300  CB  TYR B 171      -3.716   2.928  -8.980  0.00  0.00           C
ATOM   1301  CG  TYR B 171      -4.193   1.650  -8.341  0.00  0.00           C
ATOM   1302  CD1 TYR B 171      -3.508   0.459  -8.603  0.00  0.00           C
ATOM   1303  CD2 TYR B 171      -5.315   1.646  -7.516  0.00  0.00           C
ATOM   1304  CE1 TYR B 171      -3.954  -0.732  -8.038  0.00  0.00           C
ATOM   1305  CE2 TYR B 171      -5.772   0.471  -6.935  0.00  0.00           C
ATOM   1306  CZ  TYR B 171      -5.080  -0.708  -7.194  0.00  0.00           C
ATOM   1307  OH  TYR B 171      -5.495  -1.887  -6.637  0.00  0.00           O
ATOM   1308  N   GLY B 172      -4.765   5.246 -11.290  0.00  0.00           N
ATOM   1309  CA  GLY B 172      -4.675   6.596 -11.795  0.00  0.00           C
ATOM   1310  C   GLY B 172      -3.733   6.774 -12.965  0.00  0.00           C
ATOM   1311  O   GLY B 172      -3.042   7.810 -12.974  0.00  0.00           O
ATOM   1312  N   ALA B 173      -3.713   5.848 -13.901  0.00  0.00           N
ATOM   1313  CA  ALA B 173      -2.796   5.945 -15.047  0.00  0.00           C
ATOM   1314  C   ALA B 173      -3.311   6.647 -16.300  0.00  0.00           C
ATOM   1315  O   ALA B 173      -4.497   6.633 -16.622  0.00  0.00           O
ATOM   1316  CB  ALA B 173      -2.368   4.526 -15.474  0.00  0.00           C
ATOM   1317  N   PRO B 174      -2.362   7.224 -17.028  0.00  0.00           N
ATOM   1318  CA  PRO B 174      -2.672   7.938 -18.261  0.00  0.00           C
ATOM   1319  C   PRO B 174      -3.003   6.976 -19.396  0.00  0.00           C
ATOM   1320  O   PRO B 174      -3.107   5.731 -19.275  0.00  0.00           O
ATOM   1321  CB  PRO B 174      -1.422   8.757 -18.554  0.00  0.00           C
ATOM   1322  CG  PRO B 174      -0.299   7.966 -17.959  0.00  0.00           C
ATOM   1323  CD  PRO B 174      -0.917   7.291 -16.733  0.00  0.00           C
ATOM   1324  N   ARG B 175      -3.188   7.639 -20.530  0.00  0.00           N
ATOM   1325  CA  ARG B 175      -3.443   6.917 -21.786  0.00  0.00           C
ATOM   1326  C   ARG B 175      -1.976   6.646 -22.164  0.00  0.00           C
ATOM   1327  O   ARG B 175      -1.125   7.513 -21.843  0.00  0.00           O
ATOM   1328  CB  ARG B 175      -4.230   7.680 -22.826  0.00  0.00           C
ATOM   1329  CG  ARG B 175      -5.443   8.451 -22.337  0.00  0.00           C
ATOM   1330  CD  ARG B 175      -5.995   9.425 -23.330  0.00  0.00           C
ATOM   1331  NE  ARG B 175      -7.383   9.704 -23.024  0.00  0.00           N
ATOM   1332  CZ  ARG B 175      -7.983  10.770 -22.542  0.00  0.00           C
ATOM   1333  NH1 ARG B 175      -7.377  11.878 -22.235  0.00  0.00           N
ATOM   1334  NH2 ARG B 175      -9.281  10.602 -22.377  0.00  0.00           N
ATOM   1335  N   VAL B 176      -1.739   5.480 -22.737  0.00  0.00           N
ATOM   1336  CA  VAL B 176      -0.329   5.196 -23.091  0.00  0.00           C
ATOM   1337  C   VAL B 176      -0.307   5.055 -24.613  0.00  0.00           C
ATOM   1338  O   VAL B 176       0.798   4.955 -25.198  0.00  0.00           O
ATOM   1339  CB  VAL B 176       0.291   4.021 -22.321  0.00  0.00           C
ATOM   1340  CG1 VAL B 176      -0.232   3.742 -20.909  0.00  0.00           C
ATOM   1341  CG2 VAL B 176       0.204   2.700 -23.071  0.00  0.00           C
ATOM   1342  N   GLY B 177      -1.503   5.065 -25.214  0.00  0.00           N
ATOM   1343  CA  GLY B 177      -1.533   4.904 -26.684  0.00  0.00           C
ATOM   1344  C   GLY B 177      -2.873   5.178 -27.329  0.00  0.00           C
ATOM   1345  O   GLY B 177      -3.773   5.768 -26.726  0.00  0.00           O
ATOM   1346  N   ASN B 178      -2.937   4.707 -28.565  0.00  0.00           N
ATOM   1347  CA  ASN B 178      -4.117   4.903 -29.423  0.00  0.00           C
ATOM   1348  C   ASN B 178      -5.233   3.884 -29.177  0.00  0.00           C
ATOM   1349  O   ASN B 178      -5.167   2.987 -28.338  0.00  0.00           O
ATOM   1350  CB  ASN B 178      -3.676   5.000 -30.871  0.00  0.00           C
ATOM   1351  CG  ASN B 178      -3.257   3.726 -31.552  0.00  0.00           C
ATOM   1352  OD1 ASN B 178      -2.442   3.865 -32.485  0.00  0.00           O
```

FIG. 1 (cont'd)

```
ATOM   1353  ND2 ASN B 178      -3.752   2.546 -31.193  0.00  0.00           N
ATOM   1354  N   ARG B 179      -6.276   4.113 -29.958  0.00  0.00           N
ATOM   1355  CA  ARG B 179      -7.562   3.420 -30.004  0.00  0.00           C
ATOM   1356  C   ARG B 179      -7.478   1.942 -30.370  0.00  0.00           C
ATOM   1357  O   ARG B 179      -8.273   1.172 -29.770  0.00  0.00           O
ATOM   1358  CB  ARG B 179      -8.553   4.180 -30.913  0.00  0.00           C
ATOM   1359  CG  ARG B 179      -9.507   3.339 -31.746  0.00  0.00           C
ATOM   1360  CD  ARG B 179     -10.696   4.124 -32.164  0.00  0.00           C
ATOM   1361  NE  ARG B 179     -11.788   4.080 -31.194  0.00  0.00           N
ATOM   1362  CZ  ARG B 179     -12.716   3.110 -31.120  0.00  0.00           C
ATOM   1363  NH1 ARG B 179     -12.683   2.068 -31.974  0.00  0.00           N
ATOM   1364  NH2 ARG B 179     -13.676   3.194 -30.181  0.00  0.00           N
ATOM   1365  N   ALA B 180      -6.602   1.552 -31.279  0.00  0.00           N
ATOM   1366  CA  ALA B 180      -6.466   0.118 -31.651  0.00  0.00           C
ATOM   1367  C   ALA B 180      -5.840  -0.591 -30.443  0.00  0.00           C
ATOM   1368  O   ALA B 180      -6.238  -1.671 -29.950  0.00  0.00           O
ATOM   1369  CB  ALA B 180      -5.674  -0.111 -32.919  0.00  0.00           C
ATOM   1370  N   PHE B 181      -4.834   0.155 -29.954  0.00  0.00           N
ATOM   1371  CA  PHE B 181      -4.155  -0.334 -28.731  0.00  0.00           C
ATOM   1372  C   PHE B 181      -5.250  -0.329 -27.653  0.00  0.00           C
ATOM   1373  O   PHE B 181      -5.439  -1.350 -26.968  0.00  0.00           O
ATOM   1374  CB  PHE B 181      -2.907   0.442 -28.397  0.00  0.00           C
ATOM   1375  CG  PHE B 181      -1.981  -0.265 -27.451  0.00  0.00           C
ATOM   1376  CD1 PHE B 181      -1.895  -1.663 -27.467  0.00  0.00           C
ATOM   1377  CD2 PHE B 181      -1.196   0.454 -26.560  0.00  0.00           C
ATOM   1378  CE1 PHE B 181      -1.045  -2.345 -26.622  0.00  0.00           C
ATOM   1379  CE2 PHE B 181      -0.326  -0.241 -25.700  0.00  0.00           C
ATOM   1380  CZ  PHE B 181      -0.258  -1.633 -25.728  0.00  0.00           C
ATOM   1381  N   ALA B 182      -6.038   0.728 -27.555  0.00  0.00           N
ATOM   1382  CA  ALA B 182      -7.138   0.778 -26.579  0.00  0.00           C
ATOM   1383  C   ALA B 182      -8.081  -0.399 -26.821  0.00  0.00           C
ATOM   1384  O   ALA B 182      -8.532  -1.121 -25.918  0.00  0.00           O
ATOM   1385  CB  ALA B 182      -7.826   2.147 -26.617  0.00  0.00           C
ATOM   1386  N   GLU B 183      -8.405  -0.728 -28.053  0.00  0.00           N
ATOM   1387  CA  GLU B 183      -9.337  -1.824 -28.335  0.00  0.00           C
ATOM   1388  C   GLU B 183      -8.795  -3.167 -27.913  0.00  0.00           C
ATOM   1389  O   GLU B 183      -9.595  -4.053 -27.565  0.00  0.00           O
ATOM   1390  CB  GLU B 183      -9.762  -1.901 -29.812  0.00  0.00           C
ATOM   1391  CG  GLU B 183     -10.636  -0.682 -30.141  0.00  0.00           C
ATOM   1392  CD  GLU B 183     -11.136  -0.652 -31.561  0.00  0.00           C
ATOM   1393  OE1 GLU B 183     -10.402  -0.352 -32.501  0.00  0.00           O
ATOM   1394  OE2 GLU B 183     -12.357  -0.964 -31.590  0.00  0.00           O
ATOM   1395  N   PHE B 184      -7.483  -3.282 -28.013  0.00  0.00           N
ATOM   1396  CA  PHE B 184      -6.881  -4.594 -27.668  0.00  0.00           C
ATOM   1397  C   PHE B 184      -7.022  -4.923 -26.201  0.00  0.00           C
ATOM   1398  O   PHE B 184      -7.859  -5.819 -25.999  0.00  0.00           O
ATOM   1399  CB  PHE B 184      -5.431  -4.649 -28.057  0.00  0.00           C
ATOM   1400  CG  PHE B 184      -4.446  -5.717 -27.804  0.00  0.00           C
ATOM   1401  CD1 PHE B 184      -3.207  -5.367 -27.232  0.00  0.00           C
ATOM   1402  CD2 PHE B 184      -4.647  -7.047 -28.157  0.00  0.00           C
ATOM   1403  CE1 PHE B 184      -2.193  -6.283 -26.996  0.00  0.00           C
ATOM   1404  CE2 PHE B 184      -3.647  -8.011 -27.937  0.00  0.00           C
ATOM   1405  CZ  PHE B 184      -2.419  -7.613 -27.361  0.00  0.00           C
ATOM   1406  N   LEU B 185      -6.433  -4.149 -25.321  0.00  0.00           N
ATOM   1407  CA  LEU B 185      -6.389  -4.318 -23.870  0.00  0.00           C
ATOM   1408  C   LEU B 185      -7.739  -4.574 -23.204  0.00  0.00           C
ATOM   1409  O   LEU B 185      -7.885  -4.779 -21.991  0.00  0.00           O
ATOM   1410  CB  LEU B 185      -5.624  -3.133 -23.246  0.00  0.00           C
ATOM   1411  CG  LEU B 185      -4.156  -2.955 -23.589  0.00  0.00           C
```

FIG. 1 (cont'd)

```
ATOM   1412  CD1 LEU B 185      -3.714  -1.490 -23.510  0.00  0.00           C
ATOM   1413  CD2 LEU B 185      -3.267  -3.760 -22.635  0.00  0.00           C
ATOM   1414  N   THR B 186      -8.795  -4.379 -23.904  0.00  0.00           N
ATOM   1415  CA  THR B 186     -10.198  -4.541 -23.796  0.00  0.00           C
ATOM   1416  C   THR B 186     -10.495  -6.026 -23.991  0.00  0.00           C
ATOM   1417  O   THR B 186     -11.118  -6.751 -23.224  0.00  0.00           O
ATOM   1418  CB  THR B 186     -10.922  -3.708 -24.941  0.00  0.00           C
ATOM   1419  OG1 THR B 186     -10.217  -2.434 -25.056  0.00  0.00           O
ATOM   1420  CG2 THR B 186     -12.416  -3.496 -24.739  0.00  0.00           C
ATOM   1421  N   VAL B 187     -10.009  -6.450 -25.145  0.00  0.00           N
ATOM   1422  CA  VAL B 187     -10.152  -7.806 -25.680  0.00  0.00           C
ATOM   1423  C   VAL B 187      -9.128  -8.855 -25.291  0.00  0.00           C
ATOM   1424  O   VAL B 187      -9.416 -10.067 -25.496  0.00  0.00           O
ATOM   1425  CB  VAL B 187     -10.325  -7.644 -27.216  0.00  0.00           C
ATOM   1426  CG1 VAL B 187     -10.166  -8.964 -27.967  0.00  0.00           C
ATOM   1427  CG2 VAL B 187     -11.666  -6.954 -27.467  0.00  0.00           C
ATOM   1428  N   GLN B 188      -7.943  -8.434 -24.883  0.00  0.00           N
ATOM   1429  CA  GLN B 188      -6.874  -9.404 -24.571  0.00  0.00           C
ATOM   1430  C   GLN B 188      -7.293 -10.399 -23.473  0.00  0.00           C
ATOM   1431  O   GLN B 188      -8.019 -10.292 -22.501  0.00  0.00           O
ATOM   1432  CB  GLN B 188      -5.495  -8.825 -24.246  0.00  0.00           C
ATOM   1433  CG  GLN B 188      -4.300  -9.751 -24.334  0.00  0.00           C
ATOM   1434  CD  GLN B 188      -2.951  -9.086 -24.431  0.00  0.00           C
ATOM   1435  OE1 GLN B 188      -1.937  -9.595 -24.927  0.00  0.00           O
ATOM   1436  NE2 GLN B 188      -2.859  -7.841 -23.961  0.00  0.00           N
ATOM   1437  N   THR B 189      -6.660 -11.497 -23.800  0.00  0.00           N
ATOM   1438  CA  THR B 189      -6.598 -12.812 -23.238  0.00  0.00           C
ATOM   1439  C   THR B 189      -5.226 -13.161 -22.654  0.00  0.00           C
ATOM   1440  O   THR B 189      -4.134 -12.884 -23.171  0.00  0.00           O
ATOM   1441  CB  THR B 189      -7.024 -13.863 -24.373  0.00  0.00           C
ATOM   1442  OG1 THR B 189      -8.413 -14.212 -24.058  0.00  0.00           O
ATOM   1443  CG2 THR B 189      -6.143 -15.108 -24.530  0.00  0.00           C
ATOM   1444  N   GLY B 190      -5.432 -13.859 -21.549  0.00  0.00           N
ATOM   1445  CA  GLY B 190      -4.365 -14.428 -20.719  0.00  0.00           C
ATOM   1446  C   GLY B 190      -4.337 -13.581 -19.448  0.00  0.00           C
ATOM   1447  O   GLY B 190      -3.231 -13.171 -19.080  0.00  0.00           O
ATOM   1448  N   GLY B 191      -5.513 -13.394 -18.892  0.00  0.00           N
ATOM   1449  CA  GLY B 191      -5.672 -12.581 -17.666  0.00  0.00           C
ATOM   1450  C   GLY B 191      -6.550 -11.363 -18.023  0.00  0.00           C
ATOM   1451  O   GLY B 191      -7.056 -11.138 -19.154  0.00  0.00           O
ATOM   1452  N   THR B 192      -6.698 -10.509 -17.003  0.00  0.00           N
ATOM   1453  CA  THR B 192      -7.512  -9.294 -17.110  0.00  0.00           C
ATOM   1454  C   THR B 192      -6.820  -8.034 -16.621  0.00  0.00           C
ATOM   1455  O   THR B 192      -5.795  -8.041 -15.916  0.00  0.00           O
ATOM   1456  CB  THR B 192      -8.864  -9.536 -16.326  0.00  0.00           C
ATOM   1457  OG1 THR B 192      -9.236  -8.239 -15.765  0.00  0.00           O
ATOM   1458  CG2 THR B 192      -8.785 -10.592 -15.222  0.00  0.00           C
ATOM   1459  N   LEU B 193      -7.418  -6.931 -17.020  0.00  0.00           N
ATOM   1460  CA  LEU B 193      -7.025  -5.554 -16.734  0.00  0.00           C
ATOM   1461  C   LEU B 193      -8.128  -4.854 -15.935  0.00  0.00           C
ATOM   1462  O   LEU B 193      -9.299  -4.769 -16.333  0.00  0.00           O
ATOM   1463  CB  LEU B 193      -6.719  -4.938 -18.092  0.00  0.00           C
ATOM   1464  CG  LEU B 193      -5.822  -3.765 -18.392  0.00  0.00           C
ATOM   1465  CD1 LEU B 193      -6.191  -3.116 -19.746  0.00  0.00           C
ATOM   1466  CD2 LEU B 193      -5.911  -2.681 -17.327  0.00  0.00           C
ATOM   1467  N   TYR B 194      -7.720  -4.359 -14.793  0.00  0.00           N
ATOM   1468  CA  TYR B 194      -8.439  -3.591 -13.792  0.00  0.00           C
ATOM   1469  C   TYR B 194      -7.917  -2.150 -13.755  0.00  0.00           C
ATOM   1470  O   TYR B 194      -6.967  -1.849 -13.002  0.00  0.00           O
```

FIG. 1 (cont'd)

```
ATOM   1471  CB  TYR B 194      -8.212  -4.191 -12.376  0.00  0.00           C
ATOM   1472  CG  TYR B 194      -8.843  -5.565 -12.442  0.00  0.00           C
ATOM   1473  CD1 TYR B 194     -10.235  -5.628 -12.434  0.00  0.00           C
ATOM   1474  CD2 TYR B 194      -8.099  -6.715 -12.599  0.00  0.00           C
ATOM   1475  CE1 TYR B 194     -10.870  -6.855 -12.508  0.00  0.00           C
ATOM   1476  CE2 TYR B 194      -8.736  -7.944 -12.699  0.00  0.00           C
ATOM   1477  CZ  TYR B 194     -10.110  -8.001 -12.644  0.00  0.00           C
ATOM   1478  OH  TYR B 194     -10.749  -9.198 -12.749  0.00  0.00           O
ATOM   1479  N   ARG B 195      -8.623  -1.282 -14.456  0.00  0.00           N
ATOM   1480  CA  ARG B 195      -8.232   0.133 -14.592  0.00  0.00           C
ATOM   1481  C   ARG B 195      -9.063   0.975 -13.643  0.00  0.00           C
ATOM   1482  O   ARG B 195     -10.257   1.212 -13.848  0.00  0.00           O
ATOM   1483  CB  ARG B 195      -8.389   0.529 -16.043  0.00  0.00           C
ATOM   1484  CG  ARG B 195      -7.731   1.696 -16.716  0.00  0.00           C
ATOM   1485  CD  ARG B 195      -8.141   1.924 -18.132  0.00  0.00           C
ATOM   1486  NE  ARG B 195      -9.312   2.701 -18.414  0.00  0.00           N
ATOM   1487  CZ  ARG B 195      -9.894   3.862 -18.218  0.00  0.00           C
ATOM   1488  NH1 ARG B 195      -9.376   4.849 -17.492  0.00  0.00           N
ATOM   1489  NH2 ARG B 195     -11.098   4.120 -18.767  0.00  0.00           N
ATOM   1490  N   ILE B 196      -8.330   1.409 -12.613  0.00  0.00           N
ATOM   1491  CA  ILE B 196      -8.897   2.240 -11.560  0.00  0.00           C
ATOM   1492  C   ILE B 196      -8.289   3.651 -11.660  0.00  0.00           C
ATOM   1493  O   ILE B 196      -7.107   3.910 -11.704  0.00  0.00           O
ATOM   1494  CB  ILE B 196      -8.741   1.832 -10.081  0.00  0.00           C
ATOM   1495  CG1 ILE B 196      -9.371   0.440  -9.904  0.00  0.00           C
ATOM   1496  CG2 ILE B 196      -9.326   2.866  -9.098  0.00  0.00           C
ATOM   1497  CD1 ILE B 196      -8.367  -0.708 -10.220  0.00  0.00           C
ATOM   1498  N   THR B 197      -9.291   4.471 -11.742  0.00  0.00           N
ATOM   1499  CA  THR B 197      -9.428   5.904 -11.842  0.00  0.00           C
ATOM   1500  C   THR B 197     -10.252   6.367 -10.633  0.00  0.00           C
ATOM   1501  O   THR B 197     -11.151   5.620 -10.182  0.00  0.00           O
ATOM   1502  CB  THR B 197     -10.086   6.372 -13.178  0.00  0.00           C
ATOM   1503  OG1 THR B 197     -11.525   6.170 -13.038  0.00  0.00           O
ATOM   1504  CG2 THR B 197      -9.523   5.611 -14.386  0.00  0.00           C
ATOM   1505  N   HIS B 198      -9.853   7.492 -10.099  0.00  0.00           N
ATOM   1506  CA  HIS B 198     -10.461   8.119  -8.930  0.00  0.00           C
ATOM   1507  C   HIS B 198     -11.025   9.489  -9.312  0.00  0.00           C
ATOM   1508  O   HIS B 198     -10.417  10.260 -10.063  0.00  0.00           O
ATOM   1509  CB  HIS B 198      -9.540   8.373  -7.737  0.00  0.00           C
ATOM   1510  CG  HIS B 198     -10.043   9.025  -6.496  0.00  0.00           C
ATOM   1511  ND1 HIS B 198     -11.264   8.955  -5.893  0.00  0.00           N
ATOM   1512  CD2 HIS B 198      -9.284   9.784  -5.653  0.00  0.00           C
ATOM   1513  CE1 HIS B 198     -11.204   9.661  -4.785  0.00  0.00           C
ATOM   1514  NE2 HIS B 198     -10.026  10.194  -4.589  0.00  0.00           N
ATOM   1515  N   THR B 199     -12.213   9.661  -8.780  0.00  0.00           N
ATOM   1516  CA  THR B 199     -13.051  10.869  -8.915  0.00  0.00           C
ATOM   1517  C   THR B 199     -12.635  11.718 -10.097  0.00  0.00           C
ATOM   1518  O   THR B 199     -12.923  11.418 -11.272  0.00  0.00           O
ATOM   1519  CB  THR B 199     -13.046  11.511  -7.465  0.00  0.00           C
ATOM   1520  OG1 THR B 199     -14.180  12.434  -7.419  0.00  0.00           O
ATOM   1521  CG2 THR B 199     -11.732  12.177  -7.064  0.00  0.00           C
ATOM   1522  N   ASN B 200     -11.937  12.777  -9.915  0.00  0.00           N
ATOM   1523  CA  ASN B 200     -11.319  13.843 -10.639  0.00  0.00           C
ATOM   1524  C   ASN B 200      -9.847  13.778 -11.028  0.00  0.00           C
ATOM   1525  O   ASN B 200      -9.305  14.790 -11.513  0.00  0.00           O
ATOM   1526  CB  ASN B 200     -11.240  14.928  -9.519  0.00  0.00           C
ATOM   1527  CG  ASN B 200     -11.958  16.225  -9.660  0.00  0.00           C
ATOM   1528  OD1 ASN B 200     -11.869  17.044  -8.723  0.00  0.00           O
ATOM   1529  ND2 ASN B 200     -12.644  16.364 -10.788  0.00  0.00           N
```

FIG. 1 (cont'd)

```
ATOM   1530  N   ASP B 201      -9.098  12.760 -10.720  0.00  0.00           N
ATOM   1531  CA  ASP B 201      -7.639  12.678 -10.969  0.00  0.00           C
ATOM   1532  C   ASP B 201      -7.309  13.261 -12.318  0.00  0.00           C
ATOM   1533  O   ASP B 201      -7.962  12.820 -13.286  0.00  0.00           O
ATOM   1534  CB  ASP B 201      -7.373  11.213 -10.681  0.00  0.00           C
ATOM   1535  CG  ASP B 201      -5.917  10.867 -10.728  0.00  0.00           C
ATOM   1536  OD1 ASP B 201      -5.582   9.687 -10.611  0.00  0.00           O
ATOM   1537  OD2 ASP B 201      -5.137  11.816 -10.919  0.00  0.00           O
ATOM   1538  N   ILE B 202      -6.385  14.199 -12.460  0.00  0.00           N
ATOM   1539  CA  ILE B 202      -6.142  14.764 -13.802  0.00  0.00           C
ATOM   1540  C   ILE B 202      -5.419  13.802 -14.729  0.00  0.00           C
ATOM   1541  O   ILE B 202      -5.599  13.795 -15.957  0.00  0.00           O
ATOM   1542  CB  ILE B 202      -5.396  16.152 -13.765  0.00  0.00           C
ATOM   1543  CG1 ILE B 202      -5.216  16.807 -15.161  0.00  0.00           C
ATOM   1544  CG2 ILE B 202      -4.002  16.050 -13.079  0.00  0.00           C
ATOM   1545  CD1 ILE B 202      -6.393  17.010 -16.154  0.00  0.00           C
ATOM   1546  N   VAL B 203      -4.601  12.986 -14.118  0.00  0.00           N
ATOM   1547  CA  VAL B 203      -3.733  12.027 -14.853  0.00  0.00           C
ATOM   1548  C   VAL B 203      -4.451  11.107 -15.812  0.00  0.00           C
ATOM   1549  O   VAL B 203      -3.993  11.118 -17.001  0.00  0.00           O
ATOM   1550  CB  VAL B 203      -2.762  11.461 -13.799  0.00  0.00           C
ATOM   1551  CG1 VAL B 203      -1.631  10.768 -14.542  0.00  0.00           C
ATOM   1552  CG2 VAL B 203      -2.318  12.560 -12.830  0.00  0.00           C
ATOM   1553  N   PRO B 204      -5.531  10.406 -15.498  0.00  0.00           N
ATOM   1554  CA  PRO B 204      -6.254   9.543 -16.451  0.00  0.00           C
ATOM   1555  C   PRO B 204      -6.877  10.173 -17.696  0.00  0.00           C
ATOM   1556  O   PRO B 204      -7.437   9.598 -18.659  0.00  0.00           O
ATOM   1557  CB  PRO B 204      -7.330   8.902 -15.562  0.00  0.00           C
ATOM   1558  CG  PRO B 204      -6.889   9.077 -14.126  0.00  0.00           C
ATOM   1559  CD  PRO B 204      -6.064  10.352 -14.127  0.00  0.00           C
ATOM   1560  N   ARG B 205      -6.832  11.486 -17.767  0.00  0.00           N
ATOM   1561  CA  ARG B 205      -7.295  12.478 -18.703  0.00  0.00           C
ATOM   1562  C   ARG B 205      -6.170  12.966 -19.604  0.00  0.00           C
ATOM   1563  O   ARG B 205      -6.429  13.672 -20.601  0.00  0.00           O
ATOM   1564  CB  ARG B 205      -7.938  13.673 -17.984  0.00  0.00           C
ATOM   1565  CG  ARG B 205      -9.319  13.491 -17.375  0.00  0.00           C
ATOM   1566  CD  ARG B 205      -9.754  14.662 -16.568  0.00  0.00           C
ATOM   1567  NE  ARG B 205     -11.060  14.485 -15.964  0.00  0.00           N
ATOM   1568  CZ  ARG B 205     -11.798  15.406 -15.346  0.00  0.00           C
ATOM   1569  NH1 ARG B 205     -11.439  16.679 -15.187  0.00  0.00           N
ATOM   1570  NH2 ARG B 205     -12.967  14.966 -14.857  0.00  0.00           N
ATOM   1571  N   LEU B 206      -4.966  12.564 -19.296  0.00  0.00           N
ATOM   1572  CA  LEU B 206      -3.730  12.871 -20.047  0.00  0.00           C
ATOM   1573  C   LEU B 206      -3.183  11.597 -20.651  0.00  0.00           C
ATOM   1574  O   LEU B 206      -3.350  10.551 -19.988  0.00  0.00           O
ATOM   1575  CB  LEU B 206      -2.812  13.591 -19.029  0.00  0.00           C
ATOM   1576  CG  LEU B 206      -3.219  15.078 -18.999  0.00  0.00           C
ATOM   1577  CD1 LEU B 206      -2.927  15.703 -17.657  0.00  0.00           C
ATOM   1578  CD2 LEU B 206      -2.470  15.769 -20.132  0.00  0.00           C
ATOM   1579  N   PRO B 207      -2.558  11.575 -21.809  0.00  0.00           N
ATOM   1580  CA  PRO B 207      -2.290  12.694 -22.713  0.00  0.00           C
ATOM   1581  C   PRO B 207      -3.569  12.941 -23.511  0.00  0.00           C
ATOM   1582  O   PRO B 207      -4.276  11.979 -23.835  0.00  0.00           O
ATOM   1583  CB  PRO B 207      -1.095  12.172 -23.478  0.00  0.00           C
ATOM   1584  CG  PRO B 207      -0.748  10.774 -23.114  0.00  0.00           C
ATOM   1585  CD  PRO B 207      -2.014  10.323 -22.389  0.00  0.00           C
ATOM   1586  N   PRO B 208      -3.850  14.208 -23.778  0.00  0.00           N
ATOM   1587  CA  PRO B 208      -5.044  14.660 -24.489  0.00  0.00           C
ATOM   1588  C   PRO B 208      -5.531  13.679 -25.533  0.00  0.00           C
```

FIG. 1 (cont'd)

```
ATOM   1589  O   PRO B 208      -4.670  13.023 -26.153  0.00  0.00           O
ATOM   1590  CB  PRO B 208      -4.573  15.995 -25.058  0.00  0.00           C
ATOM   1591  CG  PRO B 208      -3.670  16.588 -24.012  0.00  0.00           C
ATOM   1592  CD  PRO B 208      -3.014  15.375 -23.382  0.00  0.00           C
ATOM   1593  N   ARG B 209      -6.856  13.597 -25.712  0.00  0.00           N
ATOM   1594  CA  ARG B 209      -7.490  12.712 -26.715  0.00  0.00           C
ATOM   1595  C   ARG B 209      -7.250  13.324 -28.112  0.00  0.00           C
ATOM   1596  O   ARG B 209      -6.894  12.633 -29.091  0.00  0.00           O
ATOM   1597  CB  ARG B 209      -8.978  12.402 -26.651  0.00  0.00           C
ATOM   1598  CG  ARG B 209      -9.739  12.422 -25.365  0.00  0.00           C
ATOM   1599  CD  ARG B 209      -9.917  13.753 -24.757  0.00  0.00           C
ATOM   1600  NE  ARG B 209      -8.983  14.421 -23.866  0.00  0.00           N
ATOM   1601  CZ  ARG B 209      -9.319  14.984 -22.696  0.00  0.00           C
ATOM   1602  NH1 ARG B 209      -8.411  15.600 -21.929  0.00  0.00           N
ATOM   1603  NH2 ARG B 209     -10.556  14.956 -22.196  0.00  0.00           N
ATOM   1604  N   GLU B 210      -7.425  14.630 -28.219  0.00  0.00           N
ATOM   1605  CA  GLU B 210      -7.157  15.397 -29.430  0.00  0.00           C
ATOM   1606  C   GLU B 210      -5.925  14.914 -30.197  0.00  0.00           C
ATOM   1607  O   GLU B 210      -5.957  14.776 -31.426  0.00  0.00           O
ATOM   1608  CB  GLU B 210      -6.883  16.864 -29.062  0.00  0.00           C
ATOM   1609  CG  GLU B 210      -6.420  17.266 -27.667  0.00  0.00           C
ATOM   1610  CD  GLU B 210      -7.466  17.629 -26.653  0.00  0.00           C
ATOM   1611  OE1 GLU B 210      -7.523  17.373 -25.460  0.00  0.00           O
ATOM   1612  OE2 GLU B 210      -8.386  18.321 -27.156  0.00  0.00           O
ATOM   1613  N   PHE B 211      -4.805  14.670 -29.548  0.00  0.00           N
ATOM   1614  CA  PHE B 211      -3.530  14.207 -30.044  0.00  0.00           C
ATOM   1615  C   PHE B 211      -3.371  12.731 -30.422  0.00  0.00           C
ATOM   1616  O   PHE B 211      -2.280  12.359 -30.938  0.00  0.00           O
ATOM   1617  CB  PHE B 211      -2.470  14.463 -28.949  0.00  0.00           C
ATOM   1618  CG  PHE B 211      -2.144  15.920 -28.878  0.00  0.00           C
ATOM   1619  CD1 PHE B 211      -1.472  16.526 -29.949  0.00  0.00           C
ATOM   1620  CD2 PHE B 211      -2.518  16.664 -27.763  0.00  0.00           C
ATOM   1621  CE1 PHE B 211      -1.147  17.878 -29.925  0.00  0.00           C
ATOM   1622  CE2 PHE B 211      -2.202  18.020 -27.720  0.00  0.00           C
ATOM   1623  CZ  PHE B 211      -1.516  18.613 -28.801  0.00  0.00           C
ATOM   1624  N   GLY B 212      -4.358  11.896 -30.155  0.00  0.00           N
ATOM   1625  CA  GLY B 212      -4.275  10.491 -30.515  0.00  0.00           C
ATOM   1626  C   GLY B 212      -4.578   9.455 -29.470  0.00  0.00           C
ATOM   1627  O   GLY B 212      -4.924   8.315 -29.855  0.00  0.00           O
ATOM   1628  N   TYR B 213      -4.469   9.803 -28.206  0.00  0.00           N
ATOM   1629  CA  TYR B 213      -4.706   8.794 -27.151  0.00  0.00           C
ATOM   1630  C   TYR B 213      -6.179   8.460 -26.955  0.00  0.00           C
ATOM   1631  O   TYR B 213      -7.089   9.159 -27.413  0.00  0.00           O
ATOM   1632  CB  TYR B 213      -3.935   9.296 -25.920  0.00  0.00           C
ATOM   1633  CG  TYR B 213      -2.446   9.368 -26.174  0.00  0.00           C
ATOM   1634  CD1 TYR B 213      -1.598   8.415 -25.589  0.00  0.00           C
ATOM   1635  CD2 TYR B 213      -1.858  10.353 -26.967  0.00  0.00           C
ATOM   1636  CE1 TYR B 213      -0.214   8.443 -25.771  0.00  0.00           C
ATOM   1637  CE2 TYR B 213      -0.479  10.386 -27.180  0.00  0.00           C
ATOM   1638  CZ  TYR B 213       0.341   9.432 -26.579  0.00  0.00           C
ATOM   1639  OH  TYR B 213       1.689   9.483 -26.778  0.00  0.00           O
ATOM   1640  N   SER B 214      -6.388   7.336 -26.294  0.00  0.00           N
ATOM   1641  CA  SER B 214      -7.666   6.721 -25.951  0.00  0.00           C
ATOM   1642  C   SER B 214      -7.464   5.780 -24.763  0.00  0.00           C
ATOM   1643  O   SER B 214      -6.297   5.447 -24.523  0.00  0.00           O
ATOM   1644  CB  SER B 214      -8.295   5.989 -27.139  0.00  0.00           C
ATOM   1645  OG  SER B 214      -9.264   6.883 -27.700  0.00  0.00           O
ATOM   1646  N   HIS B 215      -8.509   5.385 -24.076  0.00  0.00           N
ATOM   1647  CA  HIS B 215      -8.560   4.499 -22.909  0.00  0.00           C
```

FIG. 1 (cont'd)

```
ATOM   1648  C    HIS B 215      -9.364   3.232 -23.193  0.00  0.00           C
ATOM   1649  O    HIS B 215     -10.255   3.324 -24.046  0.00  0.00           O
ATOM   1650  CB   HIS B 215      -9.186   5.227 -21.719  0.00  0.00           C
ATOM   1651  CG   HIS B 215      -8.319   5.873 -20.697  0.00  0.00           C
ATOM   1652  ND1  HIS B 215      -7.129   5.411 -20.228  0.00  0.00           N
ATOM   1653  CD2  HIS B 215      -8.554   7.008 -19.974  0.00  0.00           C
ATOM   1654  CE1  HIS B 215      -6.655   6.226 -19.299  0.00  0.00           C
ATOM   1655  NE2  HIS B 215      -7.501   7.203 -19.117  0.00  0.00           N
ATOM   1656  N    SER B 216      -9.194   2.106 -22.588  0.00  0.00           N
ATOM   1657  CA   SER B 216      -9.777   0.773 -22.694  0.00  0.00           C
ATOM   1658  C    SER B 216     -11.167   0.466 -22.142  0.00  0.00           C
ATOM   1659  O    SER B 216     -11.753   1.481 -21.645  0.00  0.00           O
ATOM   1660  CB   SER B 216      -8.706  -0.116 -22.020  0.00  0.00           C
ATOM   1661  OG   SER B 216      -7.800   0.692 -21.276  0.00  0.00           O
ATOM   1662  N    SER B 217     -11.746  -0.770 -22.155  0.00  0.00           N
ATOM   1663  CA   SER B 217     -13.143  -0.896 -21.623  0.00  0.00           C
ATOM   1664  C    SER B 217     -13.437  -1.283 -20.244  0.00  0.00           C
ATOM   1665  O    SER B 217     -12.531  -0.371 -19.968  0.00  0.00           O
ATOM   1666  CB   SER B 217     -14.085  -1.773 -22.492  0.00  0.00           C
ATOM   1667  OG   SER B 217     -15.201  -2.464 -21.915  0.00  0.00           O
ATOM   1668  N    PRO B 218     -13.801  -1.534 -19.061  0.00  0.00           N
ATOM   1669  CA   PRO B 218     -13.858  -1.249 -17.719  0.00  0.00           C
ATOM   1670  C    PRO B 218     -12.879  -0.171 -17.310  0.00  0.00           C
ATOM   1671  O    PRO B 218     -11.702  -0.129 -17.638  0.00  0.00           O
ATOM   1672  CB   PRO B 218     -13.595  -2.547 -16.931  0.00  0.00           C
ATOM   1673  CG   PRO B 218     -14.294  -3.501 -17.835  0.00  0.00           C
ATOM   1674  CD   PRO B 218     -14.881  -2.553 -18.921  0.00  0.00           C
ATOM   1675  N    GLU B 219     -13.516   0.618 -16.503  0.00  0.00           N
ATOM   1676  CA   GLU B 219     -12.777   1.661 -15.776  0.00  0.00           C
ATOM   1677  C    GLU B 219     -13.537   1.424 -14.459  0.00  0.00           C
ATOM   1678  O    GLU B 219     -14.785   1.347 -14.491  0.00  0.00           O
ATOM   1679  CB   GLU B 219     -12.822   3.004 -16.400  0.00  0.00           C
ATOM   1680  CG   GLU B 219     -13.884   4.020 -16.028  0.00  0.00           C
ATOM   1681  CD   GLU B 219     -13.375   5.430 -16.124  0.00  0.00           C
ATOM   1682  OE1  GLU B 219     -13.063   5.953 -17.176  0.00  0.00           O
ATOM   1683  OE2  GLU B 219     -13.309   5.924 -14.989  0.00  0.00           O
ATOM   1684  N    TYR B 220     -12.758   1.271 -13.413  0.00  0.00           N
ATOM   1685  CA   TYR B 220     -13.460   1.064 -12.116  0.00  0.00           C
ATOM   1686  C    TYR B 220     -13.080   2.470 -11.593  0.00  0.00           C
ATOM   1687  O    TYR B 220     -11.903   2.847 -11.544  0.00  0.00           O
ATOM   1688  CB   TYR B 220     -13.115  -0.143 -11.269  0.00  0.00           C
ATOM   1689  CG   TYR B 220     -13.155  -1.473 -12.006  0.00  0.00           C
ATOM   1690  CD1  TYR B 220     -12.275  -1.680 -13.079  0.00  0.00           C
ATOM   1691  CD2  TYR B 220     -14.015  -2.486 -11.656  0.00  0.00           C
ATOM   1692  CE1  TYR B 220     -12.238  -2.856 -13.789  0.00  0.00           C
ATOM   1693  CE2  TYR B 220     -14.012  -3.685 -12.348  0.00  0.00           C
ATOM   1694  CZ   TYR B 220     -13.130  -3.858 -13.406  0.00  0.00           C
ATOM   1695  OH   TYR B 220     -13.159  -5.043 -14.124  0.00  0.00           O
ATOM   1696  N    TRP B 221     -14.186   3.126 -11.283  0.00  0.00           N
ATOM   1697  CA   TRP B 221     -14.173   4.503 -10.815  0.00  0.00           C
ATOM   1698  C    TRP B 221     -14.573   4.535  -9.343  0.00  0.00           C
ATOM   1699  O    TRP B 221     -15.668   4.174  -8.892  0.00  0.00           O
ATOM   1700  CB   TRP B 221     -15.168   5.339 -11.625  0.00  0.00           C
ATOM   1701  CG   TRP B 221     -15.076   6.815 -11.430  0.00  0.00           C
ATOM   1702  CD1  TRP B 221     -13.921   7.541 -11.419  0.00  0.00           C
ATOM   1703  CD2  TRP B 221     -16.138   7.769 -11.300  0.00  0.00           C
ATOM   1704  NE1  TRP B 221     -14.198   8.872 -11.262  0.00  0.00           N
ATOM   1705  CE2  TRP B 221     -15.546   9.036 -11.163  0.00  0.00           C
ATOM   1706  CE3  TRP B 221     -17.518   7.673 -11.272  0.00  0.00           C
```

FIG. 1 (cont'd)

```
ATOM   1707  CZ2 TRP B 221     -16.275  10.206 -11.006  0.00  0.00           C
ATOM   1708  CZ3 TRP B 221     -18.248   8.831 -11.104  0.00  0.00           C
ATOM   1709  CH2 TRP B 221     -17.658  10.085 -10.971  0.00  0.00           C
ATOM   1710  N   ILE B 222     -13.615   5.119  -8.640  0.00  0.00           N
ATOM   1711  CA  ILE B 222     -13.813   5.256  -7.172  0.00  0.00           C
ATOM   1712  C   ILE B 222     -14.501   6.622  -7.290  0.00  0.00           C
ATOM   1713  O   ILE B 222     -14.019   7.411  -8.133  0.00  0.00           O
ATOM   1714  CB  ILE B 222     -12.500   5.158  -6.372  0.00  0.00           C
ATOM   1715  CG1 ILE B 222     -11.619   3.947  -6.791  0.00  0.00           C
ATOM   1716  CG2 ILE B 222     -12.762   5.120  -4.834  0.00  0.00           C
ATOM   1717  CD1 ILE B 222     -10.234   3.921  -6.055  0.00  0.00           C
ATOM   1718  N   LYS B 223     -15.620   6.780  -6.613  0.00  0.00           N
ATOM   1719  CA  LYS B 223     -16.437   7.993  -6.634  0.00  0.00           C
ATOM   1720  C   LYS B 223     -16.324   8.779  -5.321  0.00  0.00           C
ATOM   1721  O   LYS B 223     -16.679   9.975  -5.316  0.00  0.00           O
ATOM   1722  CB  LYS B 223     -17.924   7.692  -6.780  0.00  0.00           C
ATOM   1723  CG  LYS B 223     -18.288   6.919  -8.030  0.00  0.00           C
ATOM   1724  CD  LYS B 223     -19.795   6.761  -8.180  0.00  0.00           C
ATOM   1725  CE  LYS B 223     -20.478   8.119  -8.108  0.00  0.00           C
ATOM   1726  NZ  LYS B 223     -21.949   8.003  -8.173  0.00  0.00           N
ATOM   1727  N   SER B 224     -15.890   8.053  -4.299  0.00  0.00           N
ATOM   1728  CA  SER B 224     -15.700   8.525  -2.925  0.00  0.00           C
ATOM   1729  C   SER B 224     -14.593   9.569  -2.942  0.00  0.00           C
ATOM   1730  O   SER B 224     -13.688   9.389  -3.753  0.00  0.00           O
ATOM   1731  CB  SER B 224     -15.391   7.373  -1.998  0.00  0.00           C
ATOM   1732  OG  SER B 224     -14.005   7.068  -1.863  0.00  0.00           O
ATOM   1733  N   GLY B 225     -14.656  10.577  -2.122  0.00  0.00           N
ATOM   1734  CA  GLY B 225     -13.711  11.681  -2.085  0.00  0.00           C
ATOM   1735  C   GLY B 225     -12.286  11.415  -1.681  0.00  0.00           C
ATOM   1736  O   GLY B 225     -11.888  10.239  -1.641  0.00  0.00           O
ATOM   1737  N   THR B 226     -11.576  12.497  -1.392  0.00  0.00           N
ATOM   1738  CA  THR B 226     -10.187  12.416  -0.919  0.00  0.00           C
ATOM   1739  C   THR B 226     -10.278  12.270   0.598  0.00  0.00           C
ATOM   1740  O   THR B 226     -11.231  12.614   1.328  0.00  0.00           O
ATOM   1741  CB  THR B 226      -9.277  13.568  -1.442  0.00  0.00           C
ATOM   1742  OG1 THR B 226      -9.062  13.167  -2.833  0.00  0.00           O
ATOM   1743  CG2 THR B 226      -7.922  13.760  -0.766  0.00  0.00           C
ATOM   1744  N   LEU B 227      -9.291  11.582   1.152  0.00  0.00           N
ATOM   1745  CA  LEU B 227      -9.030  11.213   2.534  0.00  0.00           C
ATOM   1746  C   LEU B 227     -10.237  10.510   3.167  0.00  0.00           C
ATOM   1747  O   LEU B 227     -10.335  10.351   4.402  0.00  0.00           O
ATOM   1748  CB  LEU B 227      -8.491  12.411   3.304  0.00  0.00           C
ATOM   1749  CG  LEU B 227      -7.190  13.117   2.978  0.00  0.00           C
ATOM   1750  CD1 LEU B 227      -6.844  14.102   4.109  0.00  0.00           C
ATOM   1751  CD2 LEU B 227      -6.003  12.184   2.815  0.00  0.00           C
ATOM   1752  N   VAL B 228     -11.090   9.971   2.320  0.00  0.00           N
ATOM   1753  CA  VAL B 228     -12.243   9.224   2.759  0.00  0.00           C
ATOM   1754  C   VAL B 228     -12.164   7.824   2.125  0.00  0.00           C
ATOM   1755  O   VAL B 228     -12.038   7.663   0.921  0.00  0.00           O
ATOM   1756  CB  VAL B 228     -13.605   9.867   2.518  0.00  0.00           C
ATOM   1757  CG1 VAL B 228     -13.639  11.098   1.614  0.00  0.00           C
ATOM   1758  CG2 VAL B 228     -14.636   8.857   1.976  0.00  0.00           C
ATOM   1759  N   PRO B 229     -12.347   6.885   3.045  0.00  0.00           N
ATOM   1760  CA  PRO B 229     -12.395   5.442   2.806  0.00  0.00           C
ATOM   1761  C   PRO B 229     -13.186   4.879   1.642  0.00  0.00           C
ATOM   1762  O   PRO B 229     -14.435   5.041   1.653  0.00  0.00           O
ATOM   1763  CB  PRO B 229     -13.122   4.937   4.084  0.00  0.00           C
ATOM   1764  CG  PRO B 229     -13.714   6.165   4.734  0.00  0.00           C
ATOM   1765  CD  PRO B 229     -12.535   7.130   4.513  0.00  0.00           C
```

FIG. 1 (cont'd)

```
ATOM   1766  N   VAL B 230     -12.567   4.185   0.689  0.00  0.00           N
ATOM   1767  CA  VAL B 230     -13.497   3.695  -0.376  0.00  0.00           C
ATOM   1768  C   VAL B 230     -14.297   2.615   0.366  0.00  0.00           C
ATOM   1769  O   VAL B 230     -14.069   2.312   1.542  0.00  0.00           O
ATOM   1770  CB  VAL B 230     -12.944   3.279  -1.746  0.00  0.00           C
ATOM   1771  CG1 VAL B 230     -11.510   3.769  -2.009  0.00  0.00           C
ATOM   1772  CG2 VAL B 230     -13.076   1.799  -2.053  0.00  0.00           C
ATOM   1773  N   THR B 231     -15.280   2.131  -0.353  0.00  0.00           N
ATOM   1774  CA  THR B 231     -16.134   1.051   0.105  0.00  0.00           C
ATOM   1775  C   THR B 231     -16.753   0.613  -1.248  0.00  0.00           C
ATOM   1776  O   THR B 231     -16.835   1.256  -2.288  0.00  0.00           O
ATOM   1777  CB  THR B 231     -17.228   1.182   1.199  0.00  0.00           C
ATOM   1778  OG1 THR B 231     -18.465   1.266   0.377  0.00  0.00           O
ATOM   1779  CG2 THR B 231     -17.219   2.315   2.225  0.00  0.00           C
ATOM   1780  N   ARG B 232     -17.172  -0.604  -1.116  0.00  0.00           N
ATOM   1781  CA  ARG B 232     -17.738  -1.457  -2.148  0.00  0.00           C
ATOM   1782  C   ARG B 232     -18.680  -0.762  -3.090  0.00  0.00           C
ATOM   1783  O   ARG B 232     -18.561  -0.974  -4.314  0.00  0.00           O
ATOM   1784  CB  ARG B 232     -18.365  -2.669  -1.447  0.00  0.00           C
ATOM   1785  CG  ARG B 232     -17.296  -3.459  -0.676  0.00  0.00           C
ATOM   1786  CD  ARG B 232     -17.233  -4.870  -1.122  0.00  0.00           C
ATOM   1787  NE  ARG B 232     -18.450  -5.373  -1.745  0.00  0.00           N
ATOM   1788  CZ  ARG B 232     -19.637  -5.540  -1.139  0.00  0.00           C
ATOM   1789  NH1 ARG B 232     -19.880  -5.235   0.140  0.00  0.00           N
ATOM   1790  NH2 ARG B 232     -20.563  -6.030  -1.958  0.00  0.00           N
ATOM   1791  N   ASN B 233     -19.552   0.027  -2.540  0.00  0.00           N
ATOM   1792  CA  ASN B 233     -20.533   0.761  -3.366  0.00  0.00           C
ATOM   1793  C   ASN B 233     -19.970   2.087  -3.848  0.00  0.00           C
ATOM   1794  O   ASN B 233     -20.832   2.879  -4.267  0.00  0.00           O
ATOM   1795  CB  ASN B 233     -21.820   0.872  -2.552  0.00  0.00           C
ATOM   1796  CG  ASN B 233     -22.245  -0.402  -1.839  0.00  0.00           C
ATOM   1797  OD1 ASN B 233     -21.974  -0.688  -0.652  0.00  0.00           O
ATOM   1798  ND2 ASN B 233     -22.987  -1.182  -2.620  0.00  0.00           N
ATOM   1799  N   ASP B 234     -18.690   2.377  -3.843  0.00  0.00           N
ATOM   1800  CA  ASP B 234     -18.168   3.652  -4.352  0.00  0.00           C
ATOM   1801  C   ASP B 234     -17.366   3.445  -5.643  0.00  0.00           C
ATOM   1802  O   ASP B 234     -16.771   4.372  -6.199  0.00  0.00           O
ATOM   1803  CB  ASP B 234     -17.305   4.298  -3.305  0.00  0.00           C
ATOM   1804  CG  ASP B 234     -17.981   4.513  -1.977  0.00  0.00           C
ATOM   1805  OD1 ASP B 234     -18.174   3.585  -1.193  0.00  0.00           O
ATOM   1806  OD2 ASP B 234     -18.325   5.672  -1.654  0.00  0.00           O
ATOM   1807  N   ILE B 235     -17.369   2.232  -6.144  0.00  0.00           N
ATOM   1808  CA  ILE B 235     -16.638   1.842  -7.338  0.00  0.00           C
ATOM   1809  C   ILE B 235     -17.693   1.394  -8.338  0.00  0.00           C
ATOM   1810  O   ILE B 235     -18.360   0.382  -8.053  0.00  0.00           O
ATOM   1811  CB  ILE B 235     -15.629   0.683  -7.017  0.00  0.00           C
ATOM   1812  CG1 ILE B 235     -14.430   1.118  -6.140  0.00  0.00           C
ATOM   1813  CG2 ILE B 235     -15.100  -0.022  -8.307  0.00  0.00           C
ATOM   1814  CD1 ILE B 235     -14.603   0.801  -4.649  0.00  0.00           C
ATOM   1815  N   VAL B 236     -17.743   2.031  -9.492  0.00  0.00           N
ATOM   1816  CA  VAL B 236     -18.702   1.761 -10.574  0.00  0.00           C
ATOM   1817  C   VAL B 236     -17.859   1.308 -11.783  0.00  0.00           C
ATOM   1818  O   VAL B 236     -16.698   1.706 -11.889  0.00  0.00           O
ATOM   1819  CB  VAL B 236     -19.681   2.881 -11.007  0.00  0.00           C
ATOM   1820  CG1 VAL B 236     -20.546   3.446  -9.887  0.00  0.00           C
ATOM   1821  CG2 VAL B 236     -19.031   4.055 -11.717  0.00  0.00           C
ATOM   1822  N   LYS B 237     -18.511   0.501 -12.600  0.00  0.00           N
ATOM   1823  CA  LYS B 237     -17.805   0.001 -13.792  0.00  0.00           C
ATOM   1824  C   LYS B 237     -18.517   0.677 -14.971  0.00  0.00           C
```

FIG. 1 (cont'd)

```
ATOM   1825  O    LYS B 237     -19.730   0.677 -15.220  0.00  0.00           O
ATOM   1826  CB   LYS B 237     -17.792  -1.492 -13.931  0.00  0.00           C
ATOM   1827  CG   LYS B 237     -17.134  -2.025 -15.214  0.00  0.00           C
ATOM   1828  CD   LYS B 237     -16.938  -3.532 -15.070  0.00  0.00           C
ATOM   1829  CE   LYS B 237     -18.082  -4.341 -15.640  0.00  0.00           C
ATOM   1830  NZ   LYS B 237     -19.396  -3.641 -15.491  0.00  0.00           N
ATOM   1831  N    ILE B 238     -17.597   1.302 -15.722  0.00  0.00           N
ATOM   1832  CA   ILE B 238     -17.959   2.076 -16.896  0.00  0.00           C
ATOM   1833  C    ILE B 238     -17.331   1.515 -18.162  0.00  0.00           C
ATOM   1834  O    ILE B 238     -16.158   1.770 -18.470  0.00  0.00           O
ATOM   1835  CB   ILE B 238     -17.446   3.569 -16.709  0.00  0.00           C
ATOM   1836  CG1  ILE B 238     -17.808   4.067 -15.290  0.00  0.00           C
ATOM   1837  CG2  ILE B 238     -17.922   4.496 -17.868  0.00  0.00           C
ATOM   1838  CD1  ILE B 238     -18.041   5.589 -15.169  0.00  0.00           C
ATOM   1839  N    GLU B 239     -18.245   0.869 -18.877  0.00  0.00           N
ATOM   1840  CA   GLU B 239     -17.868   0.264 -20.167  0.00  0.00           C
ATOM   1841  C    GLU B 239     -17.818   1.283 -21.308  0.00  0.00           C
ATOM   1842  O    GLU B 239     -18.341   2.404 -21.269  0.00  0.00           O
ATOM   1843  CB   GLU B 239     -18.776  -0.891 -20.569  0.00  0.00           C
ATOM   1844  CG   GLU B 239     -18.526  -2.189 -19.805  0.00  0.00           C
ATOM   1845  CD   GLU B 239     -19.672  -2.829 -19.087  0.00  0.00           C
ATOM   1846  OE1  GLU B 239     -20.866  -2.638 -19.268  0.00  0.00           O
ATOM   1847  OE2  GLU B 239     -19.282  -3.648 -18.222  0.00  0.00           O
ATOM   1848  N    GLY B 240     -17.102   0.785 -22.315  0.00  0.00           N
ATOM   1849  CA   GLY B 240     -16.884   1.534 -23.553  0.00  0.00           C
ATOM   1850  C    GLY B 240     -15.559   2.273 -23.662  0.00  0.00           C
ATOM   1851  O    GLY B 240     -15.087   2.914 -22.691  0.00  0.00           O
ATOM   1852  N    ILE B 241     -15.019   2.145 -24.892  0.00  0.00           N
ATOM   1853  CA   ILE B 241     -13.728   2.859 -25.123  0.00  0.00           C
ATOM   1854  C    ILE B 241     -14.168   4.308 -24.879  0.00  0.00           C
ATOM   1855  O    ILE B 241     -15.332   4.746 -24.949  0.00  0.00           O
ATOM   1856  CB   ILE B 241     -12.959   2.525 -26.432  0.00  0.00           C
ATOM   1857  CG1  ILE B 241     -12.125   1.221 -26.228  0.00  0.00           C
ATOM   1858  CG2  ILE B 241     -12.002   3.632 -26.961  0.00  0.00           C
ATOM   1859  CD1  ILE B 241     -12.538   0.007 -27.090  0.00  0.00           C
ATOM   1860  N    ASP B 242     -13.205   5.051 -24.404  0.00  0.00           N
ATOM   1861  CA   ASP B 242     -13.375   6.456 -24.062  0.00  0.00           C
ATOM   1862  C    ASP B 242     -14.727   6.799 -23.462  0.00  0.00           C
ATOM   1863  O    ASP B 242     -15.131   7.948 -23.760  0.00  0.00           O
ATOM   1864  CB   ASP B 242     -13.072   7.261 -25.347  0.00  0.00           C
ATOM   1865  CG   ASP B 242     -11.589   7.027 -25.659  0.00  0.00           C
ATOM   1866  OD1  ASP B 242     -11.233   6.448 -26.685  0.00  0.00           O
ATOM   1867  OD2  ASP B 242     -10.883   7.472 -24.731  0.00  0.00           O
ATOM   1868  N    ALA B 243     -15.372   5.978 -22.661  0.00  0.00           N
ATOM   1869  CA   ALA B 243     -16.643   6.398 -22.070  0.00  0.00           C
ATOM   1870  C    ALA B 243     -16.324   7.639 -21.221  0.00  0.00           C
ATOM   1871  O    ALA B 243     -15.232   7.952 -20.740  0.00  0.00           O
ATOM   1872  CB   ALA B 243     -17.309   5.317 -21.262  0.00  0.00           C
ATOM   1873  N    THR B 244     -17.394   8.374 -21.111  0.00  0.00           N
ATOM   1874  CA   THR B 244     -17.538   9.624 -20.355  0.00  0.00           C
ATOM   1875  C    THR B 244     -18.206   9.150 -19.063  0.00  0.00           C
ATOM   1876  O    THR B 244     -18.411   7.919 -19.048  0.00  0.00           O
ATOM   1877  CB   THR B 244     -18.359  10.747 -21.110  0.00  0.00           C
ATOM   1878  OG1  THR B 244     -19.725  10.259 -21.374  0.00  0.00           O
ATOM   1879  CG2  THR B 244     -17.702  11.247 -22.415  0.00  0.00           C
ATOM   1880  N    GLY B 245     -18.523   9.971 -18.089  0.00  0.00           N
ATOM   1881  CA   GLY B 245     -19.242   9.454 -16.937  0.00  0.00           C
ATOM   1882  C    GLY B 245     -18.637   9.048 -15.629  0.00  0.00           C
ATOM   1883  O    GLY B 245     -19.348   9.051 -14.590  0.00  0.00           O
```

FIG. 1 (cont'd)

```
ATOM   1884  N    GLY B 246     -17.379   8.668 -15.713  0.00  0.00           N
ATOM   1885  CA   GLY B 246     -16.573   8.286 -14.533  0.00  0.00           C
ATOM   1886  C    GLY B 246     -15.567   9.452 -14.511  0.00  0.00           C
ATOM   1887  O    GLY B 246     -16.005  10.593 -14.440  0.00  0.00           O
ATOM   1888  N    ASN B 247     -14.323   9.081 -14.545  0.00  0.00           N
ATOM   1889  CA   ASN B 247     -13.194  10.018 -14.544  0.00  0.00           C
ATOM   1890  C    ASN B 247     -13.422  11.012 -15.687  0.00  0.00           C
ATOM   1891  O    ASN B 247     -13.588  12.222 -15.428  0.00  0.00           O
ATOM   1892  CB   ASN B 247     -11.865   9.255 -14.606  0.00  0.00           C
ATOM   1893  CG   ASN B 247     -10.672  10.189 -14.436  0.00  0.00           C
ATOM   1894  OD1  ASN B 247     -10.469  10.604 -13.276  0.00  0.00           O
ATOM   1895  ND2  ASN B 247     -10.008  10.462 -15.558  0.00  0.00           N
ATOM   1896  N    ASN B 248     -13.437  10.499 -16.898  0.00  0.00           N
ATOM   1897  CA   ASN B 248     -13.649  11.246 -18.139  0.00  0.00           C
ATOM   1898  C    ASN B 248     -14.999  11.981 -18.169  0.00  0.00           C
ATOM   1899  O    ASN B 248     -16.145  11.612 -18.462  0.00  0.00           O
ATOM   1900  CB   ASN B 248     -13.480  10.318 -19.338  0.00  0.00           C
ATOM   1901  CG   ASN B 248     -13.055  11.031 -20.591  0.00  0.00           C
ATOM   1902  OD1  ASN B 248     -13.460  10.690 -21.701  0.00  0.00           O
ATOM   1903  ND2  ASN B 248     -12.188  12.030 -20.468  0.00  0.00           N
ATOM   1904  N    GLN B 249     -14.835  13.242 -17.790  0.00  0.00           N
ATOM   1905  CA   GLN B 249     -15.862  14.278 -17.703  0.00  0.00           C
ATOM   1906  C    GLN B 249     -15.148  15.627 -17.902  0.00  0.00           C
ATOM   1907  O    GLN B 249     -13.994  15.922 -17.505  0.00  0.00           O
ATOM   1908  CB   GLN B 249     -16.626  14.166 -16.406  0.00  0.00           C
ATOM   1909  CG   GLN B 249     -17.626  13.071 -16.091  0.00  0.00           C
ATOM   1910  CD   GLN B 249     -18.358  13.411 -14.792  0.00  0.00           C
ATOM   1911  OE1  GLN B 249     -18.267  14.560 -14.329  0.00  0.00           O
ATOM   1912  NE2  GLN B 249     -19.084  12.494 -14.155  0.00  0.00           N
ATOM   1913  N    PRO B 250     -15.883  16.541 -18.529  0.00  0.00           N
ATOM   1914  CA   PRO B 250     -15.469  17.938 -18.774  0.00  0.00           C
ATOM   1915  C    PRO B 250     -15.913  18.653 -17.501  0.00  0.00           C
ATOM   1916  O    PRO B 250     -16.894  19.398 -17.396  0.00  0.00           O
ATOM   1917  CB   PRO B 250     -16.229  18.295 -20.025  0.00  0.00           C
ATOM   1918  CG   PRO B 250     -17.582  17.680 -19.722  0.00  0.00           C
ATOM   1919  CD   PRO B 250     -17.270  16.361 -19.023  0.00  0.00           C
ATOM   1920  N    ASN B 251     -15.175  18.305 -16.484  0.00  0.00           N
ATOM   1921  CA   ASN B 251     -15.266  18.634 -15.066  0.00  0.00           C
ATOM   1922  C    ASN B 251     -14.023  19.428 -14.706  0.00  0.00           C
ATOM   1923  O    ASN B 251     -13.163  19.660 -15.607  0.00  0.00           O
ATOM   1924  CB   ASN B 251     -15.437  17.225 -14.465  0.00  0.00           C
ATOM   1925  CG   ASN B 251     -15.390  17.037 -12.978  0.00  0.00           C
ATOM   1926  OD1  ASN B 251     -16.319  16.482 -12.351  0.00  0.00           O
ATOM   1927  ND2  ASN B 251     -14.317  17.486 -12.317  0.00  0.00           N
ATOM   1928  N    ILE B 252     -13.903  19.852 -13.457  0.00  0.00           N
ATOM   1929  CA   ILE B 252     -12.646  20.574 -13.117  0.00  0.00           C
ATOM   1930  C    ILE B 252     -11.784  19.535 -12.417  0.00  0.00           C
ATOM   1931  O    ILE B 252     -12.276  18.984 -11.427  0.00  0.00           O
ATOM   1932  CB   ILE B 252     -12.929  21.912 -12.403  0.00  0.00           C
ATOM   1933  CG1  ILE B 252     -12.667  23.017 -13.459  0.00  0.00           C
ATOM   1934  CG2  ILE B 252     -12.114  22.025 -11.084  0.00  0.00           C
ATOM   1935  CD1  ILE B 252     -12.703  22.656 -14.974  0.00  0.00           C
ATOM   1936  N    PRO B 253     -10.631  19.306 -13.026  0.00  0.00           N
ATOM   1937  CA   PRO B 253      -9.672  18.304 -12.547  0.00  0.00           C
ATOM   1938  C    PRO B 253      -8.955  18.677 -11.255  0.00  0.00           C
ATOM   1939  O    PRO B 253      -8.794  19.854 -10.885  0.00  0.00           O
ATOM   1940  CB   PRO B 253      -8.709  18.107 -13.715  0.00  0.00           C
ATOM   1941  CG   PRO B 253      -9.205  18.959 -14.848  0.00  0.00           C
ATOM   1942  CD   PRO B 253     -10.136  19.992 -14.233  0.00  0.00           C
```

FIG. 1 (cont'd)

```
ATOM   1943  N    ASP B 254      -8.513   17.615  -10.600  0.00  0.00           N
ATOM   1944  CA   ASP B 254      -7.816   17.590   -9.322  0.00  0.00           C
ATOM   1945  C    ASP B 254      -6.533   16.741   -9.319  0.00  0.00           C
ATOM   1946  O    ASP B 254      -6.392   15.628   -9.854  0.00  0.00           O
ATOM   1947  CB   ASP B 254      -8.786   17.071   -8.250  0.00  0.00           C
ATOM   1948  CG   ASP B 254      -8.742   17.668   -6.866  0.00  0.00           C
ATOM   1949  OD1  ASP B 254      -9.267   17.071   -5.896  0.00  0.00           O
ATOM   1950  OD2  ASP B 254      -8.209   18.793   -6.688  0.00  0.00           O
ATOM   1951  N    ILE B 255      -5.616   17.370   -8.579  0.00  0.00           N
ATOM   1952  CA   ILE B 255      -4.288   16.732   -8.377  0.00  0.00           C
ATOM   1953  C    ILE B 255      -4.169   15.903   -7.109  0.00  0.00           C
ATOM   1954  O    ILE B 255      -3.779   14.719   -7.245  0.00  0.00           O
ATOM   1955  CB   ILE B 255      -3.231   17.860   -8.653  0.00  0.00           C
ATOM   1956  CG1  ILE B 255      -3.116   17.984  -10.194  0.00  0.00           C
ATOM   1957  CG2  ILE B 255      -1.905   17.573   -7.923  0.00  0.00           C
ATOM   1958  CD1  ILE B 255      -2.386   19.268  -10.675  0.00  0.00           C
ATOM   1959  N    PRO B 256      -4.543   16.297   -5.908  0.00  0.00           N
ATOM   1960  CA   PRO B 256      -4.481   15.474   -4.703  0.00  0.00           C
ATOM   1961  C    PRO B 256      -5.470   14.320   -4.692  0.00  0.00           C
ATOM   1962  O    PRO B 256      -5.573   13.510   -3.758  0.00  0.00           O
ATOM   1963  CB   PRO B 256      -4.760   16.435   -3.545  0.00  0.00           C
ATOM   1964  CG   PRO B 256      -5.650   17.460   -4.202  0.00  0.00           C
ATOM   1965  CD   PRO B 256      -5.067   17.639   -5.606  0.00  0.00           C
ATOM   1966  N    ALA B 257      -6.265   14.178   -5.720  0.00  0.00           N
ATOM   1967  CA   ALA B 257      -7.225   13.109   -5.899  0.00  0.00           C
ATOM   1968  C    ALA B 257      -6.401   11.992   -6.539  0.00  0.00           C
ATOM   1969  O    ALA B 257      -6.770   10.820   -6.586  0.00  0.00           O
ATOM   1970  CB   ALA B 257      -8.351   13.362   -6.880  0.00  0.00           C
ATOM   1971  N    HIS B 258      -5.287   12.420   -7.099  0.00  0.00           N
ATOM   1972  CA   HIS B 258      -4.394   11.499   -7.806  0.00  0.00           C
ATOM   1973  C    HIS B 258      -3.783   10.570   -6.764  0.00  0.00           C
ATOM   1974  O    HIS B 258      -3.692    9.370   -7.081  0.00  0.00           O
ATOM   1975  CB   HIS B 258      -3.314   12.205   -8.635  0.00  0.00           C
ATOM   1976  CG   HIS B 258      -2.504   11.294   -9.495  0.00  0.00           C
ATOM   1977  ND1  HIS B 258      -3.017   10.502  -10.487  0.00  0.00           N
ATOM   1978  CD2  HIS B 258      -1.165   11.099   -9.507  0.00  0.00           C
ATOM   1979  CE1  HIS B 258      -2.050    9.834  -11.072  0.00  0.00           C
ATOM   1980  NE2  HIS B 258      -0.922   10.191  -10.505  0.00  0.00           N
ATOM   1981  N    LEU B 259      -3.424   11.129   -5.621  0.00  0.00           N
ATOM   1982  CA   LEU B 259      -2.774   10.396   -4.542  0.00  0.00           C
ATOM   1983  C    LEU B 259      -3.693    9.688   -3.538  0.00  0.00           C
ATOM   1984  O    LEU B 259      -3.175    9.257   -2.476  0.00  0.00           O
ATOM   1985  CB   LEU B 259      -1.852   11.365   -3.789  0.00  0.00           C
ATOM   1986  CG   LEU B 259      -0.731   12.171   -4.375  0.00  0.00           C
ATOM   1987  CD1  LEU B 259      -0.678   12.273   -5.885  0.00  0.00           C
ATOM   1988  CD2  LEU B 259      -0.985   13.545   -3.754  0.00  0.00           C
ATOM   1989  N    TRP B 260      -4.967    9.587   -3.868  0.00  0.00           N
ATOM   1990  CA   TRP B 260      -5.837    8.922   -2.890  0.00  0.00           C
ATOM   1991  C    TRP B 260      -6.526    7.732   -3.538  0.00  0.00           C
ATOM   1992  O    TRP B 260      -7.688    7.874   -3.914  0.00  0.00           O
ATOM   1993  CB   TRP B 260      -6.856    9.840   -2.221  0.00  0.00           C
ATOM   1994  CG   TRP B 260      -7.600    9.165   -1.110  0.00  0.00           C
ATOM   1995  CD1  TRP B 260      -8.842    8.602   -1.170  0.00  0.00           C
ATOM   1996  CD2  TRP B 260      -7.124    8.946    0.233  0.00  0.00           C
ATOM   1997  NE1  TRP B 260      -9.184    8.088    0.052  0.00  0.00           N
ATOM   1998  CE2  TRP B 260      -8.150    8.270    0.931  0.00  0.00           C
ATOM   1999  CE3  TRP B 260      -5.954    9.251    0.904  0.00  0.00           C
ATOM   2000  CZ2  TRP B 260      -8.034    7.897    2.262  0.00  0.00           C
ATOM   2001  CZ3  TRP B 260      -5.852    8.904    2.228  0.00  0.00           C
```

FIG. 1 (cont'd)

```
ATOM   2002  CH2 TRP B 260      -6.860   8.235   2.914  0.00  0.00           C
ATOM   2003  N   TYR B 261      -5.784   6.642  -3.650  0.00  0.00           N
ATOM   2004  CA  TYR B 261      -6.387   5.423  -4.240  0.00  0.00           C
ATOM   2005  C   TYR B 261      -6.520   4.430  -3.115  0.00  0.00           C
ATOM   2006  O   TYR B 261      -5.650   3.570  -2.974  0.00  0.00           O
ATOM   2007  CB  TYR B 261      -5.570   4.925  -5.423  0.00  0.00           C
ATOM   2008  CG  TYR B 261      -5.944   5.723  -6.660  0.00  0.00           C
ATOM   2009  CD1 TYR B 261      -5.738   7.088  -6.803  0.00  0.00           C
ATOM   2010  CD2 TYR B 261      -6.508   5.039  -7.727  0.00  0.00           C
ATOM   2011  CE1 TYR B 261      -6.096   7.760  -7.952  0.00  0.00           C
ATOM   2012  CE2 TYR B 261      -6.848   5.678  -8.916  0.00  0.00           C
ATOM   2013  CZ  TYR B 261      -6.641   7.042  -9.018  0.00  0.00           C
ATOM   2014  OH  TYR B 261      -7.012   7.624 -10.197  0.00  0.00           O
ATOM   2015  N   PHE B 262      -7.584   4.513  -2.329  0.00  0.00           N
ATOM   2016  CA  PHE B 262      -7.902   3.661  -1.186  0.00  0.00           C
ATOM   2017  C   PHE B 262      -7.035   3.954   0.044  0.00  0.00           C
ATOM   2018  O   PHE B 262      -7.107   3.226   1.039  0.00  0.00           O
ATOM   2019  CB  PHE B 262      -7.683   2.169  -1.425  0.00  0.00           C
ATOM   2020  CG  PHE B 262      -8.443   1.546  -2.528  0.00  0.00           C
ATOM   2021  CD1 PHE B 262      -9.691   1.004  -2.278  0.00  0.00           C
ATOM   2022  CD2 PHE B 262      -7.909   1.539  -3.816  0.00  0.00           C
ATOM   2023  CE1 PHE B 262     -10.392   0.417  -3.319  0.00  0.00           C
ATOM   2024  CE2 PHE B 262      -8.602   0.973  -4.887  0.00  0.00           C
ATOM   2025  CZ  PHE B 262      -9.866   0.402  -4.620  0.00  0.00           C
ATOM   2026  N   GLY B 263      -6.185   4.928  -0.053  0.00  0.00           N
ATOM   2027  CA  GLY B 263      -5.229   5.338   0.958  0.00  0.00           C
ATOM   2028  C   GLY B 263      -4.110   6.058   0.187  0.00  0.00           C
ATOM   2029  O   GLY B 263      -4.221   6.225  -1.039  0.00  0.00           O
ATOM   2030  N   LEU B 264      -3.092   6.451   0.939  0.00  0.00           N
ATOM   2031  CA  LEU B 264      -1.985   7.204   0.352  0.00  0.00           C
ATOM   2032  C   LEU B 264      -1.342   6.460  -0.792  0.00  0.00           C
ATOM   2033  O   LEU B 264      -1.273   5.247  -0.630  0.00  0.00           O
ATOM   2034  CB  LEU B 264      -0.934   7.477   1.411  0.00  0.00           C
ATOM   2035  CG  LEU B 264      -0.966   8.775   2.206  0.00  0.00           C
ATOM   2036  CD1 LEU B 264      -1.261   9.979   1.319  0.00  0.00           C
ATOM   2037  CD2 LEU B 264      -2.023   8.602   3.281  0.00  0.00           C
ATOM   2038  N   ILE B 265      -0.936   7.170  -1.803  0.00  0.00           N
ATOM   2039  CA  ILE B 265      -0.202   6.480  -2.895  0.00  0.00           C
ATOM   2040  C   ILE B 265       0.579   7.595  -3.587  0.00  0.00           C
ATOM   2041  O   ILE B 265       0.105   8.722  -3.736  0.00  0.00           O
ATOM   2042  CB  ILE B 265      -1.062   5.487  -3.700  0.00  0.00           C
ATOM   2043  CG1 ILE B 265      -0.088   4.986  -4.811  0.00  0.00           C
ATOM   2044  CG2 ILE B 265      -2.420   5.985  -4.260  0.00  0.00           C
ATOM   2045  CD1 ILE B 265      -0.434   3.570  -5.345  0.00  0.00           C
ATOM   2046  N   GLY B 266       1.836   7.293  -3.832  0.00  0.00           N
ATOM   2047  CA  GLY B 266       2.826   8.160  -4.451  0.00  0.00           C
ATOM   2048  C   GLY B 266       3.602   9.005  -3.468  0.00  0.00           C
ATOM   2049  O   GLY B 266       4.648   9.622  -3.715  0.00  0.00           O
ATOM   2050  N   THR B 267       3.113   9.067  -2.266  0.00  0.00           N
ATOM   2051  CA  THR B 267       3.565   9.781  -1.059  0.00  0.00           C
ATOM   2052  C   THR B 267       3.996   8.770  -0.004  0.00  0.00           C
ATOM   2053  O   THR B 267       3.253   8.529   0.963  0.00  0.00           O
ATOM   2054  CB  THR B 267       2.382  10.764  -0.687  0.00  0.00           C
ATOM   2055  OG1 THR B 267       2.224  10.884   0.747  0.00  0.00           O
ATOM   2056  CG2 THR B 267       0.998  10.348  -1.229  0.00  0.00           C
ATOM   2057  N   CYS B 268       5.109   8.084  -0.185  0.00  0.00           N
ATOM   2058  CA  CYS B 268       5.790   7.089   0.637  0.00  0.00           C
ATOM   2059  C   CYS B 268       7.300   7.370   0.255  0.00  0.00           C
ATOM   2060  O   CYS B 268       7.950   6.987  -0.703  0.00  0.00           O
```

FIG. 1 (cont'd)

```
ATOM   2061  CB   CYS B 268       5.730    5.554    0.663  0.00  0.00           C
ATOM   2062  SG   CYS B 268       7.097    4.714    1.604  0.00  0.00           S
ATOM   2063  N    LEU B 269       7.772    8.096    1.199  0.00  0.00           N
ATOM   2064  CA   LEU B 269       8.856    8.817    1.767  0.00  0.00           C
ATOM   2065  CB   LEU B 269       8.717    8.576    3.317  0.00  0.00           C
ATOM   2066  CG   LEU B 269       7.378    8.954    3.971  0.00  0.00           C
ATOM   2067  CD1  LEU B 269       6.584    7.774    4.558  0.00  0.00           C
ATOM   2068  CD2  LEU B 269       7.608    9.965    5.108  0.00  0.00           C
ATOM   2069  C    LEU B 269      10.275    8.611    1.206  0.00  0.00           C
ATOM   2070  OT   LEU B 269      10.582    7.650    0.464  0.00  0.00           O
ATOM   2071  OE   LEU B 269      11.013    9.581    1.572  0.00  0.00           O
ATOM   2072  N    LIP1    1       4.155   13.598   -1.915  0.00  0.00           N
ATOM   2073  C    LIP1    1       2.861   13.926   -1.250  0.00  0.00           C
ATOM   2074  C1   LIP1    1       4.774   14.860   -2.425  0.00  0.00           C
ATOM   2075  C2   LIP1    1       5.074   13.010   -0.886  0.00  0.00           C
ATOM   2076  C3   LIP1    1       3.966   12.591   -3.013  0.00  0.00           C
ATOM   2077  C4   LIP1    1       5.223   12.036   -3.755  0.00  0.00           C
ATOM   2078  P7   LIP1    1       6.100   11.437   -6.259  0.00  0.00           P
ATOM   2079  O    LIP1    1       7.395   12.033   -5.825  0.00  0.00           O
ATOM   2080  O1   LIP1    1       6.313    9.888   -6.596  0.00  0.00           O
ATOM   2081  O2   LIP1    1       5.692   12.177   -7.616  0.00  0.00           O
ATOM   2082  O3   LIP1    1       4.994   11.629   -5.114  0.00  0.00           O
ATOM   2083  C5   LIP1    1       4.465   12.841   -7.934  0.00  0.00           C
ATOM   2084  C6   LIP1    1       3.338   11.836   -8.307  0.00  0.00           C
ATOM   2085  O4   LIP1    1       3.696   11.455   -9.654  0.00  0.00           O
ATOM   2086  C7   LIP1    1       2.798   10.866  -10.467  0.00  0.00           C
ATOM   2087  O5   LIP1    1       1.642   10.851  -10.076  0.00  0.00           O
ATOM   2088  C8   LIP1    1       3.101   10.251  -11.822  0.00  0.00           C
ATOM   2089  C9   LIP1    1       1.969   12.593   -8.232  0.00  0.00           C
ATOM   2090  O6   LIP1    1       1.547   13.297   -9.413  0.00  0.00           O
ATOM   2091  C10  LIP1    1       1.299   14.602   -9.217  0.00  0.00           C
ATOM   2092  O7   LIP1    1       1.189   15.109   -8.113  0.00  0.00           O
ATOM   2093  C11  LIP1    1       1.206   15.420  -10.481  0.00  0.00           C
ATOM   2094  C12  LIP1    1       2.109   10.843  -12.863  0.00  0.00           C
ATOM   2095  C13  LIP1    1       2.280   10.311  -14.315  0.00  0.00           C
ATOM   2096  C14  LIP1    1       1.529   11.164  -15.379  0.00  0.00           C
ATOM   2097  C15  LIP1    1       2.514   11.916  -16.318  0.00  0.00           C
ATOM   2098  C16  LIP1    1       1.777   12.992  -17.163  0.00  0.00           C
ATOM   2099  C17  LIP1    1       2.720   13.701  -18.176  0.00  0.00           C
ATOM   2100  C18  LIP1    1       2.305   13.410  -19.601  0.00  0.00           C
ATOM   2101  C19  LIP1    1       1.392   14.120  -20.281  0.00  0.00           C
ATOM   2102  C20  LIP1    1       0.630   15.294  -19.709  0.00  0.00           C
ATOM   2103  C21  LIP1    1       1.504   16.579  -19.612  0.00  0.00           C
ATOM   2104  C22  LIP1    1       1.441   17.308  -18.237  0.00  0.00           C
ATOM   2105  C23  LIP1    1       1.037   18.806  -18.359  0.00  0.00           C
ATOM   2106  C24  LIP1    1       1.603   19.657  -17.187  0.00  0.00           C
ATOM   2107  C25  LIP1    1       1.152   21.141  -17.303  0.00  0.00           C
ATOM   2108  C26  LIP1    1       1.923   22.058  -16.317  0.00  0.00           C
ATOM   2109  C27  LIP1    1       3.297   22.481  -16.901  0.00  0.00           C
ATOM   2110  C28  LIP1    1       0.835   16.897  -10.170  0.00  0.00           C
ATOM   2111  C29  LIP1    1       0.840   17.805  -11.434  0.00  0.00           C
ATOM   2112  C30  LIP1    1       0.897   19.305  -11.025  0.00  0.00           C
ATOM   2113  C31  LIP1    1       1.852   20.136  -11.930  0.00  0.00           C
ATOM   2114  C32  LIP1    1       3.337   20.097  -11.447  0.00  0.00           C
ATOM   2115  C33  LIP1    1       4.124   21.381  -11.831  0.00  0.00           C
ATOM   2116  C34  LIP1    1       4.955   21.156  -13.125  0.00  0.00           C
ATOM   2117  C35  LIP1    1       6.169   22.116  -13.260  0.00  0.00           C
ATOM   2118  C36  LIP1    1       7.174   21.736  -14.384  0.00  0.00           C
ATOM   2119  C37  LIP1    1       8.525   21.285  -13.760  0.00  0.00           C
```

FIG. 1 (cont'd)

```
ATOM   2120  C38 LIP1    1       8.403  20.156 -12.696  0.00  0.00           C
ATOM   2121  C39 LIP1    1       9.744  19.418 -12.424  0.00  0.00           C
ATOM   2122  C40 LIP1    1       9.996  18.294 -13.469  0.00  0.00           C
ATOM   2123  C41 LIP1    1      11.337  17.561 -13.189  0.00  0.00           C
END
```

Alignment of fungal lipolytic enzyme sequences

```
           1                                                     50
seq1    SSSSTQDYRI ASEAEIKAHT FYTALSANA. .......YCR TVIPG.....
seq2    .SSSTQDYRI ASEAEIKAHT FYTALSANA. .......YCR TVIPG.....
seq3    ..SIDGGIRA ATSQEINELT YYTTLSANS. .......YCR TVIPG.....
seq4    .SASDGGKVV AATTAQIQEF TKYAGIAATA .......YCR SVVPG.....
seq5    ....TAGHAL AASTQ.GISE DLYSRL.VEM ATISQAAYAD LCNIPST...
seq6    ....TAGHAL AASTQ.GISE DLYSRL.VEM ATISQAAYAD LCNIPST...
seq7    ........AV GVTTTDFSNF KFYIQHGAAA .......YC. .NSEAAAGSK
seq8    .......... TVTTQDLSNF RFYLQHADAA .......YC. .NFNTAVGKP
seq9    .......... DIPTTQLEDF KFWVQYAAAT .......YCP NNYVAKDGEK
seq10   .......... DVSTSELDQF EFWVQYAAAS .......YYE ADYTAQVGDK
seq11   .......... SVSTSTLDEL QLFAQWSAAA .......YCS NNID.SKDSN
seq12   .......... SVSTSTLDEL QLFSQWSAAA .......YCS NNID.SDDSN
seq13   .......... DVSSSLLNNL DLFAQYSAAA .......YCD ENLN.STGTK
seq14   .......... EVSQDLFNQF NLFAQYSAAA .......YCG KNNDAPAGTN 51                                                    100
seq1    GRWSCPHCGV AS..NLQITK TFST..LITD TNVLVAVGEK EKTIYVVFRG
seq2    GQWSCPHCDV AP..NLNITK TFTT..LITD TNVLVAVGEN EKTIYVVFRG
seq3    ATWDCIHCDA TE..DLKIIK TWST..LIYD TNAMVARGDS EKTIYIVFRG
seq4    NKWDCVQCQK WVP.DGKIIT TFTS..LLSD TNGYVLRDKQ KTIYLVFRGT
seq5    .......... .......IIK GEKIYNSQTD INGWILRDDS SKEIITVFRG
seq6    .......... .......IIK GEKIYNSQTD INGWILRYC. .NSEAAAGSK
seq7    ITCSNNGCPT VQGNGATIVT SF..VGSKTG IGGYVATDSA RKEIVVSFRG
seq8    VHCSAGNCPD IEKDAAIVVG SV..VGTKTG IGAYVATDNA RKEIVVSVRG
seq9    LNCSVGNCPD VEAAGSTVKL SFS.DDTITD TAGFVAVDNT NKAIVVAFRG
seq10   LSCSKGNCPE VEATGATVSY DFS.DSTITD TAGYIAVDHT NSAVVLAFRG
seq11   LTCTANACPS VEEASTTMLL EFDLTNDFGG TAGFLAADNT NKRLVVAFRG
seq12   VTCTADACPS VEEASTKMLL EFDLTNNFGG TAGFLAADNT NKRLVVAFRG
seq13   LTCSVGNCPL VEAASTQSLD EFNESSSYGN PAGYLAADET NKLLVLSFRG
seq14   ITCTGNACPE VEKADATFLY SFE.DSGVGD VTGFLALDNT NKLIVLSFRG 101                                                   150
seq1    TSSIRNAIAD IVFVPVNYPP V...NGAKVH KGFLDSYNEV QDKLVAEVKA
seq2    TSSIRNAIAD IVFVPVNYPP V...NGAKVH KGFLDSYNEV QDKLVAEVKA
seq3    SSSIRNWIAD LTFVPVSYPP V...SGTKVH KGFLDSYGEV QNELVATVLD
seq4    NSFRSAITDI VFNFSDYKPV ...KGAKVHA GFLSSYEQVV NDYFPVVQEQ
seq5    TGSDTNLQLD TNYTLTPFDT LPQCNGCEVH GGYYIGWVSV QDQVESLVKQ
seq6    ITCSNNGCPT VQGNGATIVT SF..VGSKTG IGGYVATDDS SKEIITVFRG
seq7    SININRNWLTN LDFG.QEDCS L..VSGCGVH SGFQRAWNEI SSQATAAVAS
seq8    SINVRNWITN FNFG.QKTCD L..VAGCGVH TGFLDAWEEV AANVKAAVSA
seq9    SYSIRNWVTD ATFP.QTDPG L..CDGCKAE LGFWTAWKVV RDRIIKTLDE
seq10   SYSVRNWVAD ATFV.HTNPG L..CDGCLAE LGFWSSWKLV RDDIIKELKE
seq11   SSTIENWIAN LDFILEDNDD L..CTGCKVH TGFWKAWESA ADELTSKIKS
seq12   SSTIKNWIAD LDFILQDNDD L..CTGCKVH TGFWKAWEAA ADNLTSKIKS
seq13   SADLANWVAN LNFGLEDASD L..CSGCEVH SGFWKAWSEI ADTITSKVES
seq14   SRSIENWIGN LNFDLKEIND I..CSGCRGH DGFTSSWRSV ADTLRQKVED
```

```
         151                                                        200
seq1     QLDRHPGYKI VVTGHSLGGA TAVLSALDLY HHGHA....N IEIYTQGQPR
seq2     QLDRHPGYKI VVTGHSLGGA TAVLSALDLY HHGHD....N IEIYTQGQPR
seq3     QFKQYPSYKV AVTGHSLGGA TALLCALDLY QREEGLSSSN LFLYTQGQPR
seq4     LTAHPTYKVI VTGHSLGGAQ ALLAGMDLYQ REPRLSPKNL SIFTVGGPRV
seq5     QVSQYPDYAL TVTGHSLGAS LAALTAAQL. SATYD....N IRLYTFGEPR
seq6     TGSDTNLQLD TNYTLTPFDT LPQCNSCEVH GGYYIGWISV QDQVESLVQQ
seq7     ARKANPSFNV ISTGHSLGGA VAVLAAANLR VGGT......P VDIYTYGSPR
seq8     AKTANPTFKF VVTGHSLGGA VATIAAAYLR KDGF......P FDLYTYGSPR
seq9     LKPEHSDYKI VVVGHSLGAA IASLAAADLR TKNY......D AILYAYAAPR
seq10    VVAQNPNYEL VVVGHSLGAA VATLAATDLR GKGYP....S AKLYAYASPR
seq11    AMSTYSGYTL YFTGHSLGGA LATLGATVLR NDGY.....S VELYTYGCPR
seq12    AMSTYSGYTL YFTGHSLGGA LATLGATVLR NDGY.....S VELYTYGCPR
seq13    ALSDHSDYSL VLTGHSYGAA LAALAATALR NSGH.....S VELYNYGQPR
seq14    AVREHPDYRV VFTGHSLGGA LATVAGADLR GNGY.....D IDVFSYGAPR 201                                                        250
seq1     IGTPAFANYV IGT....... KIPYQRLVHE RDIVPHLPPG AFGFLHAGEE
seq2     IGTPEFANYV IGT....... KIPYQRLVNE RDIVPHLPPG AFGFLHAGEE
seq3     VGDPAFANYV VST....... GIPYRRTVNE RDIVPHLPPA AFGFLHAGEE
seq4     GNPTFAYYVE ST.......G IPFQRTVHKR DIVPHVPPQS FGFLHPGVES
seq5     SGNQAFASYM NDAFQASSPD TTQYFRVTHA NDGIPNLPPV EQGYAHGGVE
seq6     QVSQFPDYAL TVTGHSLGAS LAALTAAQL. SATYD....N IRLYTFGEPR
seq7     VGNAQLSAFV SNQ....... AGGEYRVTHA DDPVPRLPPL IFGYRHTTPE
seq8     VGNDFFANFV TQQ....... TGAEYRVTHG DDPVPRLPPI VFGYRHTSPE
seq9     VANKPLAEFI TNQ....... .GNNYRFTHN DDPVPKLPLL TMGYVHISPE
seq10    VGNAALAKYI TAQ....... .GNNFRFTHT NDPVPKLPLL SMGYVHVSPE
seq11    IGNYALAEHI TSQ......G SGANFRVTHL NDIVPRVPPM DFGFSQPSPE
seq12    VGNYALAEHI TSQ......G SGANFPVTHL NDIVPRVPPM DFGFSQPSPE
seq13    LGNEALATYI TDQ......N KGGNYRVTHT NDIVPKLPPT LLGYHHFSPE
seq14    VGNRAFAEFL TVQ......T GGTLYRITHT NDIVPRLPPR EFGYSHSSPE 251                                                        300
seq1     FWIMK..... ....DSSLRV CPNGIETDNC SNSIVPFT.. SVIDHLSYLD
seq2     FWIMK..... ....DSSLRV CPNGIETDNC SNSIVPFT.. SVIDHLSYLD
seq3     YWITD..... ..NSPETVQV CTSDLETSDC SNSIVPFT.. SVLDHLSYFG
seq4     WIKS...... ..GTSNVQIC TSEIETKDCS NSIVPFT..S ILDHLSYFDI
seq5     YWSV....DP YSAQNTFVCT GDEVQCCE.A QGGQGVN... ..NAHTTYF.
seq6     S.NQAFASYM NDAFQASSPD TTQYFRVTHA NDGIPNLPPA DEGYAHGVVE
seq7     FWLSGGGGDK VDYTISDVKV CEGAANLG.C NGGTLGL... DIAAHLHYF.
seq8     YWLNG.GPLD KDYTVTEIKV CEGIANVM.C NGGTIGL... DILAHITYF.
seq9     YYITA..PDN TTVTDNQVTV LDGYVNFK.G NTGTSGGLPD LLAFHSHVWY
seq10    YWITS..PNN ATVSTSDIKV IDGDVSFD.G NTGTGLPLLT DFEAHIWYF.
seq11    YWITS..GNG ASVTASDIEV IEGINSTA.G NAGEATV... SVLAHLWYF.
seq12    YWITS..GTG ASVTASDIEL IEGINSTA.G NAGEATV... DVLAHLWYF.
seq13    YYISS..ADE ATVTTTDVTE VTGIDATG.G NDGTDGT... SIDAHRWYF.
seq14    YWIKS..GTL VPVTRNDIVK IEGIDATG.G NNQPNIP... DIPAHLWYF.
```

FIG. 2 (cont'd)

```
        301                                                      350
seq1   MNTGL.CL..  ..........  ..........  ..........  ..........
seq2   MNTGL.CL..  ..........  ..........  ..........  ..........
seq3   INTGL.CT..  ..........  ..........  ..........  ..........
seq4   NEGS..CL..  ..........  ..........  ..........  ..........
seq5   GMTSGACTW.  ..........  ..........  ..........  ..........
seq6   YWSV....DP  YSAQNTFVCT  GDEVQCCE.A  QGGQGVN...  ...NAHTTYF.
seq7   QATDA.CNAG  GFSWRR....  ..........  ..........  ..........
seq8   QSMAT.CAPI  AIPWKR....  ..........  ..........  ..........
seq9   FIHADACKGP  GLPLR.....  ..........  ..........  ..........
seq10  VQVDAGKGPG  LPFKR.....  ..........  ..........  ..........
seq11  FAISE.CLL.  ..........  ..........  ..........  ..........
seq12  FAISE.CLL.  ..........  ..........  ..........  ..........
seq13  IYISE.CS..  ..........  ..........  ..........  ..........
seq14  GLIGT.CL..  ..........  ..........  ..........  ..........

351         366
seq1   ..........  ......
seq2   ..........  ......
seq3   ..........  ......
seq4   ..........  ......
seq5   ..........  ......
seq6   GMTSGHCTW.  ......
seq7   ..........  ......
seq8   ..........  ......
seq9   ..........  ......
seq10  ..........  ......
seq11  ..........  ......
seq12  ..........  ......
seq13  ..........  ......
seq14  ..........  ......
```

FIG. 2 (cont'd)

SEQUENCE LISTING

```
<160> NUMBER OF SEQ ID NOS: 17

<210> SEQ ID NO 1
<211> LENGTH: 265
<212> TYPE: PRT
<213> ORGANISM: Absidia reflexa

<400> SEQUENCE: 1

Ser Ser Ser Ser Thr Gln Asp Tyr Arg Ile Ala Ser Glu Ala Glu Ile
1               5                   10                  15

Lys Ala His Thr Phe Tyr Thr Ala Leu Ser Ala Asn Ala Tyr Cys Arg
                20                  25                  30

Thr Val Ile Pro Gly Gly Arg Trp Ser Cys Pro His Cys Gly Val Ala
            35                  40                  45

Ser Asn Leu Gln Ile Thr Lys Thr Phe Ser Thr Leu Ile Thr Asp Thr
        50                  55                  60

Asn Val Leu Val Ala Val Gly Glu Lys Glu Lys Thr Ile Tyr Val Val
65                  70                  75                  80

Phe Arg Gly Thr Ser Ser Ile Arg Asn Ala Ile Ala Asp Ile Val Phe
                85                  90                  95

Val Pro Val Asn Tyr Pro Pro Val Asn Gly Ala Lys Val His Lys Gly
            100                 105                 110

Phe Leu Asp Ser Tyr Asn Glu Val Gln Asp Lys Leu Val Ala Glu Val
        115                 120                 125

Lys Ala Gln Leu Asp Arg His Pro Gly Tyr Lys Ile Val Val Thr Gly
    130                 135                 140

His Ser Leu Gly Gly Ala Thr Ala Val Leu Ser Ala Leu Asp Leu Tyr
145                 150                 155                 160

His His Gly His Ala Asn Ile Glu Ile Tyr Thr Gln Gly Gln Pro Arg
                165                 170                 175

Ile Gly Thr Pro Ala Phe Ala Asn Tyr Val Ile Gly Thr Lys Ile Pro
            180                 185                 190

Tyr Gln Arg Leu Val His Glu Arg Asp Ile Val Pro His Leu Pro Pro
        195                 200                 205

Gly Ala Phe Gly Phe Leu His Ala Gly Glu Glu Phe Trp Ile Met Lys
    210                 215                 220

Asp Ser Ser Leu Arg Val Cys Pro Asn Gly Ile Glu Thr Asp Asn Cys
225                 230                 235                 240

Ser Asn Ser Ile Val Pro Phe Thr Ser Val Ile Asp His Leu Ser Tyr
                245                 250                 255
```

```
Leu Asp Met Asn Thr Gly Leu Cys Leu
            260                 265

<210> SEQ ID NO 2
<211> LENGTH: 264
<212> TYPE: PRT
<213> ORGANISM: Absidia corymbifera

<400> SEQUENCE: 2

Ser Ser Ser Thr Gln Asp Tyr Arg Ile Ala Ser Glu Ala Glu Ile Lys
1               5                   10                  15

Ala His Thr Phe Tyr Thr Ala Leu Ser Ala Asn Ala Tyr Cys Arg Thr
            20                  25                  30

Val Ile Pro Gly Gly Gln Trp Ser Cys Pro His Cys Asp Val Ala Pro
        35                  40                  45

Asn Leu Asn Ile Thr Lys Thr Phe Thr Thr Leu Ile Thr Asp Thr Asn
    50                  55                  60

Val Leu Val Ala Val Gly Glu Asn Glu Lys Thr Ile Tyr Val Val Phe
65                  70                  75                  80

Arg Gly Thr Ser Ser Ile Arg Asn Ala Ile Ala Asp Ile Val Phe Val
                85                  90                  95

Pro Val Asn Tyr Pro Pro Val Asn Gly Ala Lys Val His Lys Gly Phe
            100                 105                 110

Leu Asp Ser Tyr Asn Glu Val Gln Asp Lys Leu Val Ala Glu Val Lys
        115                 120                 125

Ala Gln Leu Asp Arg His Pro Gly Tyr Lys Ile Val Val Thr Gly His
    130                 135                 140

Ser Leu Gly Gly Ala Thr Ala Val Leu Ser Ala Leu Asp Leu Tyr His
145                 150                 155                 160

His Gly His Asp Asn Ile Glu Ile Tyr Thr Gln Gly Gln Pro Arg Ile
                165                 170                 175

Gly Thr Pro Glu Phe Ala Asn Tyr Val Ile Gly Thr Lys Ile Pro Tyr
            180                 185                 190

Gln Arg Leu Val Asn Glu Arg Asp Ile Val Pro His Leu Pro Pro Gly
        195                 200                 205

Ala Phe Gly Phe Leu His Ala Gly Glu Glu Phe Trp Ile Met Lys Asp
    210                 215                 220

Ser Ser Leu Arg Val Cys Pro Asn Gly Ile Glu Thr Asn Cys Ser
225                 230                 235                 240

Asn Ser Ile Val Pro Phe Thr Ser Val Ile Asp His Leu Ser Tyr Leu
                245                 250                 255

Asp Met Asn Thr Gly Leu Cys Leu
            260

<210> SEQ ID NO 3
<211> LENGTH: 269
<212> TYPE: PRT
<213> ORGANISM: Rhizomucor miehei

<400> SEQUENCE: 3

Ser Ile Asp Gly Gly Ile Arg Ala Ala Thr Ser Gln Glu Ile Asn Glu
1               5                   10                  15

Leu Thr Tyr Tyr Thr Thr Leu Ser Ala Asn Ser Tyr Cys Arg Thr Val
            20                  25                  30

Ile Pro Gly Ala Thr Trp Asp Cys Ile His Cys Asp Ala Thr Glu Asp
        35                  40                  45
```

```
Leu Lys Ile Ile Lys Thr Trp Ser Thr Leu Ile Tyr Asp Thr Asn Ala
 50                  55                  60

Met Val Ala Arg Gly Asp Ser Glu Lys Thr Ile Tyr Ile Val Phe Arg
 65                  70                  75                  80

Gly Ser Ser Ser Ile Arg Asn Trp Ile Ala Asp Leu Thr Phe Val Pro
                 85                  90                  95

Val Ser Tyr Pro Pro Val Ser Gly Thr Lys Val His Lys Gly Phe Leu
            100                 105                 110

Asp Ser Tyr Gly Glu Val Gln Asn Glu Leu Val Ala Thr Val Leu Asp
        115                 120                 125

Gln Phe Lys Gln Tyr Pro Ser Tyr Lys Val Ala Val Thr Gly His Ser
130                 135                 140

Leu Gly Gly Ala Thr Ala Leu Leu Cys Ala Leu Asp Leu Tyr Gln Arg
145                 150                 155                 160

Glu Glu Gly Leu Ser Ser Ser Asn Leu Phe Leu Tyr Thr Gln Gly Gln
                165                 170                 175

Pro Arg Val Gly Asp Pro Ala Phe Ala Asn Tyr Val Val Ser Thr Gly
            180                 185                 190

Ile Pro Tyr Arg Arg Thr Val Asn Glu Arg Asp Ile Val Pro His Leu
        195                 200                 205

Pro Pro Ala Ala Phe Gly Phe Leu His Ala Gly Glu Glu Tyr Trp Ile
210                 215                 220

Thr Asp Asn Ser Pro Glu Thr Val Gln Val Cys Thr Ser Asp Leu Glu
225                 230                 235                 240

Thr Ser Asp Cys Ser Asn Ser Ile Val Pro Phe Thr Ser Val Leu Asp
                245                 250                 255

His Leu Ser Tyr Phe Gly Ile Asn Thr Gly Leu Cys Thr
            260                 265

<210> SEQ ID NO 4
<211> LENGTH: 270
<212> TYPE: PRT
<213> ORGANISM: Rhizopus oryzae

<400> SEQUENCE: 4

Ser Ala Ser Asp Gly Gly Lys Val Val Ala Ala Thr Thr Ala Gln Ile
 1               5                  10                  15

Gln Glu Phe Thr Lys Tyr Ala Gly Ile Ala Ala Thr Ala Tyr Cys Arg
                 20                  25                  30

Ser Val Val Pro Gly Asn Lys Trp Asp Cys Val Gln Cys Gln Lys Trp
             35                  40                  45

Val Pro Asp Gly Lys Ile Ile Thr Thr Phe Thr Ser Leu Leu Ser Asp
 50                  55                  60

Thr Asn Gly Tyr Val Leu Arg Asp Lys Gln Lys Thr Ile Tyr Leu Val
 65                  70                  75                  80

Phe Arg Gly Thr Asn Ser Phe Arg Ser Ala Ile Thr Asp Ile Val Phe
                 85                  90                  95

Asn Phe Ser Asp Tyr Lys Pro Val Lys Gly Ala Lys Val His Ala Gly
            100                 105                 110

Phe Leu Ser Ser Tyr Glu Gln Val Val Asn Asp Tyr Phe Pro Val Val
        115                 120                 125

Gln Glu Gln Leu Thr Ala His Pro Thr Tyr Lys Val Ile Val Thr Gly
130                 135                 140

His Ser Leu Gly Gly Ala Gln Ala Leu Leu Ala Gly Met Asp Leu Tyr
145                 150                 155                 160
```

```
Gln Arg Glu Pro Arg Leu Ser Pro Lys Asn Leu Ser Ile Phe Thr Val
            165                 170                 175

Gly Gly Pro Arg Val Gly Asn Pro Thr Phe Ala Tyr Tyr Val Glu Ser
            180                 185                 190

Thr Gly Ile Pro Phe Gln Arg Thr Val His Lys Arg Asp Ile Val Pro
            195                 200                 205

His Val Pro Pro Gln Ser Phe Gly Phe Leu His Pro Gly Val Glu Ser
        210                 215                 220

Trp Ile Lys Ser Gly Thr Ser Asn Val Gln Ile Cys Thr Ser Glu Ile
225                 230                 235                 240

Glu Thr Lys Asp Cys Ser Asn Ser Ile Val Pro Phe Thr Ser Ile Leu
                245                 250                 255

Asp His Leu Ser Tyr Phe Asp Ile Asn Glu Gly Ser Cys Leu
            260                 265
```

<210> SEQ ID NO 5
<211> LENGTH: 267
<212> TYPE: PRT
<213> ORGANISM: Aspergillus niger

<400> SEQUENCE: 5

```
Thr Ala Gly His Ala Leu Ala Ala Ser Thr Gln Gly Ile Ser Glu Asp
1               5                   10                  15

Leu Tyr Ser Arg Leu Val Glu Met Ala Thr Ile Ser Gln Ala Ala Tyr
            20                  25                  30

Ala Asp Leu Cys Asn Ile Pro Ser Thr Ile Ile Lys Gly Glu Lys Ile
            35                  40                  45

Tyr Asn Ser Gln Thr Asp Ile Asn Gly Trp Ile Leu Arg Asp Asp Ser
        50                  55                  60

Ser Lys Glu Ile Ile Thr Val Phe Arg Gly Thr Gly Ser Asp Thr Asn
65                  70                  75                  80

Leu Gln Leu Asp Thr Asn Tyr Thr Leu Thr Pro Phe Asp Thr Leu Pro
                85                  90                  95

Gln Cys Asn Gly Cys Glu Val His Gly Gly Tyr Tyr Ile Gly Trp Val
            100                 105                 110

Ser Val Gln Asp Gln Val Glu Ser Leu Val Lys Gln Gln Val Ser Gln
            115                 120                 125

Tyr Pro Asp Tyr Ala Leu Thr Val Thr Gly His Ser Leu Gly Ala Ser
        130                 135                 140

Leu Ala Ala Leu Thr Ala Ala Gln Leu Ser Ala Thr Tyr Asp Asn Ile
145                 150                 155                 160

Arg Leu Tyr Thr Phe Gly Glu Pro Arg Ser Gly Asn Gln Ala Phe Ala
                165                 170                 175

Ser Tyr Met Asn Asp Ala Phe Gln Ala Ser Ser Pro Asp Thr Thr Gln
            180                 185                 190

Tyr Phe Arg Val Thr His Ala Asn Asp Gly Ile Pro Asn Leu Pro Pro
            195                 200                 205

Val Glu Gln Gly Tyr Ala His Gly Gly Val Glu Tyr Trp Ser Val Asp
        210                 215                 220

Pro Tyr Ser Ala Gln Asn Thr Phe Val Cys Thr Gly Asp Glu Val Gln
225                 230                 235                 240

Cys Cys Glu Ala Gln Gly Gly Gln Gly Val Asn Asn Ala His Thr Thr
                245                 250                 255

Tyr Phe Gly Met Thr Ser Gly Ala Cys Thr Trp
            260                 265
```

260             265

<210> SEQ ID NO 6
<211> LENGTH: 312
<212> TYPE: PRT
<213> ORGANISM: Aspergillus tubingensis

<400> SEQUENCE: 6

Thr Ala Gly His Ala Leu Ala Ala Ser Thr Gln Gly Ile Ser Glu Asp
1               5                   10                  15

Leu Tyr Ser Arg Leu Val Glu Met Ala Thr Ile Ser Gln Ala Ala Tyr
            20                  25                  30

Ala Asp Leu Cys Asn Ile Pro Ser Thr Ile Ile Lys Gly Glu Lys Ile
        35                  40                  45

Tyr Asn Ser Gln Thr Asp Ile Asn Gly Trp Ile Leu Arg Tyr Cys Asn
    50                  55                  60

Ser Glu Ala Ala Ala Gly Ser Lys Ile Thr Cys Ser Asn Asn Gly Cys
65                  70                  75                  80

Pro Thr Val Gln Gly Asn Gly Ala Thr Ile Val Thr Ser Phe Val Gly
                85                  90                  95

Ser Lys Thr Gly Ile Gly Gly Tyr Val Ala Thr Asp Asp Ser Ser Lys
            100                 105                 110

Glu Ile Ile Thr Val Phe Arg Gly Thr Gly Ser Asp Thr Asn Leu Gln
        115                 120                 125

Leu Asp Thr Asn Tyr Thr Leu Thr Pro Phe Asp Thr Leu Pro Gln Cys
    130                 135                 140

Asn Ser Cys Glu Val His Gly Gly Tyr Tyr Ile Gly Trp Ile Ser Val
145                 150                 155                 160

Gln Asp Gln Val Glu Ser Leu Val Gln Gln Val Ser Gln Phe Pro
                165                 170                 175

Asp Tyr Ala Leu Thr Val Thr Gly His Ser Leu Gly Ala Ser Leu Ala
            180                 185                 190

Ala Leu Thr Ala Ala Gln Leu Ser Ala Thr Tyr Asp Asn Ile Arg Leu
        195                 200                 205

Tyr Thr Phe Gly Glu Pro Arg Ser Asn Gln Ala Phe Ala Ser Tyr Met
    210                 215                 220

Asn Asp Ala Phe Gln Ala Ser Ser Pro Asp Thr Thr Gln Tyr Phe Arg
225                 230                 235                 240

Val Thr His Ala Asn Asp Gly Ile Pro Asn Leu Pro Pro Ala Asp Glu
                245                 250                 255

Gly Tyr Ala His Gly Val Val Glu Tyr Trp Ser Val Asp Pro Tyr Ser
            260                 265                 270

Ala Gln Asn Thr Phe Val Cys Thr Gly Asp Glu Val Gln Cys Cys Glu
        275                 280                 285

Ala Gln Gly Gly Gln Gly Val Asn Asn Ala His Thr Thr Tyr Phe Gly
    290                 295                 300

Met Thr Ser Gly His Cys Thr Trp
305                 310

<210> SEQ ID NO 7
<211> LENGTH: 274
<212> TYPE: PRT
<213> ORGANISM: Fusarium oxysporum

<400> SEQUENCE: 7

Gly Val Thr Thr Thr Asp Phe Ser Asn Phe Lys Phe Tyr Ile Gln His

```
            1               5                  10                 15
        Gly Ala Ala Ala Tyr Cys Asn Ser Glu Ala Ala Gly Ser Lys Ile
                        20                 25                 30

Thr Cys Ser Asn Asn Gly Cys Pro Thr Val Gln Gly Asn Gly Ala Thr
                        35                 40                 45

Ile Val Thr Ser Phe Val Gly Ser Lys Thr Gly Ile Gly Gly Tyr Val
                    50                 55                 60

Ala Thr Asp Ser Ala Arg Lys Glu Ile Val Ser Phe Arg Gly Ser
        65                  70                 75                 80

Ile Asn Ile Arg Asn Trp Leu Thr Asn Leu Asp Phe Gly Gln Glu Asp
                        85                 90                 95

Cys Ser Leu Val Ser Gly Cys Val His Ser Gly Phe Gln Arg Ala
                    100                105                110

Trp Asn Glu Ile Ser Ser Gln Ala Thr Ala Val Ala Ser Ala Arg
                    115                120                125

Lys Ala Asn Pro Ser Phe Asn Val Ile Ser Thr Gly His Ser Leu Gly
                    130                135                140

Gly Ala Val Ala Val Leu Ala Ala Asn Leu Arg Val Gly Gly Thr
        145                 150                155                160

Pro Val Asp Ile Tyr Thr Tyr Gly Ser Pro Arg Val Gly Asn Ala Gln
                        165                170                175

Leu Ser Ala Phe Val Ser Asn Gln Ala Gly Gly Glu Tyr Arg Val Thr
                    180                185                190

His Ala Asp Asp Pro Val Pro Arg Leu Pro Pro Leu Ile Phe Gly Tyr
                    195                200                205

Arg His Thr Thr Pro Glu Phe Trp Leu Ser Gly Gly Gly Asp Lys
                    210                215                220

Val Asp Tyr Thr Ile Ser Asp Val Lys Val Cys Glu Gly Ala Ala Asn
        225                 230                235                240

Leu Gly Cys Asn Gly Gly Thr Leu Gly Leu Asp Ile Ala Ala His Leu
                        245                250                255

His Tyr Phe Gln Ala Thr Asp Ala Cys Asn Ala Gly Gly Phe Ser Trp
                        260                265                270

Arg Arg

<210> SEQ ID NO 8
<211> LENGTH: 273
<212> TYPE: PRT
<213> ORGANISM: Fusarium heterosporum

<400> SEQUENCE: 8

Thr Val Thr Thr Gln Asp Leu Ser Asn Phe Arg Phe Tyr Leu Gln His
        1                   5                  10                 15

Ala Asp Ala Ala Tyr Cys Asn Phe Asn Thr Ala Val Gly Lys Pro Val
                        20                 25                 30

His Cys Ser Ala Gly Asn Cys Pro Asp Ile Glu Lys Asp Ala Ala Ile
                        35                 40                 45

Val Val Gly Ser Val Val Gly Thr Lys Thr Gly Ile Gly Ala Tyr Val
                    50                 55                 60

Ala Thr Asp Asn Ala Arg Lys Glu Ile Val Val Ser Val Arg Gly Ser
        65                  70                 75                 80

Ile Asn Val Arg Asn Trp Ile Thr Asn Phe Asn Phe Gly Gln Lys Thr
                        85                 90                 95

Cys Asp Leu Val Ala Gly Cys Gly Val His Thr Gly Phe Leu Asp Ala
```

```
                  100                 105                 110
Trp Glu Glu Val Ala Ala Asn Val Lys Ala Val Ser Ala Ala Lys
            115                 120                 125
Thr Ala Asn Pro Thr Phe Lys Phe Val Val Thr Gly His Ser Leu Gly
        130                 135                 140
Gly Ala Val Ala Thr Ile Ala Ala Ala Tyr Leu Arg Lys Asp Gly Phe
145                 150                 155                 160
Pro Phe Asp Leu Tyr Thr Tyr Gly Ser Pro Arg Val Gly Asn Asp Phe
                165                 170                 175
Phe Ala Asn Phe Val Thr Gln Gln Thr Gly Ala Glu Tyr Arg Val Thr
            180                 185                 190
His Gly Asp Asp Pro Val Pro Arg Leu Pro Pro Ile Val Phe Gly Tyr
        195                 200                 205
Arg His Thr Ser Pro Glu Tyr Trp Leu Asn Gly Gly Pro Leu Asp Lys
        210                 215                 220
Asp Tyr Thr Val Thr Glu Ile Lys Val Cys Glu Gly Ile Ala Asn Val
225                 230                 235                 240
Met Cys Asn Gly Gly Thr Ile Gly Leu Asp Ile Leu Ala His Ile Thr
                245                 250                 255
Tyr Phe Gln Ser Met Ala Thr Cys Ala Pro Ile Ala Ile Pro Trp Lys
            260                 265                 270
Arg

<210> SEQ ID NO 9
<211> LENGTH: 278
<212> TYPE: PRT
<213> ORGANISM: Aspergillus oryzae

<400> SEQUENCE: 9

Asp Ile Pro Thr Thr Gln Leu Glu Asp Phe Lys Phe Trp Val Gln Tyr
1               5                   10                  15
Ala Ala Ala Thr Tyr Cys Pro Asn Asn Tyr Val Ala Lys Asp Gly Glu
            20                  25                  30
Lys Leu Asn Cys Ser Val Gly Asn Cys Pro Asp Val Glu Ala Ala Gly
        35                  40                  45
Ser Thr Val Lys Leu Ser Phe Ser Asp Asp Thr Ile Thr Asp Thr Ala
    50                  55                  60
Gly Phe Val Ala Val Asp Asn Thr Asn Lys Ala Ile Val Val Ala Phe
65                  70                  75                  80
Arg Gly Ser Tyr Ser Ile Arg Asn Trp Val Thr Asp Ala Thr Phe Pro
                85                  90                  95
Gln Thr Asp Pro Gly Leu Cys Asp Gly Cys Lys Ala Glu Leu Gly Phe
            100                 105                 110
Trp Thr Ala Trp Lys Val Val Arg Asp Arg Ile Ile Lys Thr Leu Asp
        115                 120                 125
Glu Leu Lys Pro Glu His Ser Asp Tyr Lys Ile Val Val Val Gly His
    130                 135                 140
Ser Leu Gly Ala Ala Ile Ala Ser Leu Ala Ala Ala Asp Leu Arg Thr
145                 150                 155                 160
Lys Asn Tyr Asp Ala Ile Leu Tyr Ala Tyr Ala Ala Pro Arg Val Ala
                165                 170                 175
Asn Lys Pro Leu Ala Glu Phe Ile Thr Asn Gln Gly Asn Asn Tyr Arg
            180                 185                 190
Phe Thr His Asn Asp Asp Pro Val Pro Lys Leu Pro Leu Leu Thr Met
```

```
                    195                 200                 205
Gly Tyr Val His Ile Ser Pro Glu Tyr Tyr Ile Thr Ala Pro Asp Asn
    210                 215                 220

Thr Thr Val Thr Asp Asn Gln Val Thr Val Leu Asp Gly Tyr Val Asn
225                 230                 235                 240

Phe Lys Gly Asn Thr Gly Thr Ser Gly Gly Leu Pro Asp Leu Leu Ala
                245                 250                 255

Phe His Ser His Val Trp Tyr Phe Ile His Ala Asp Ala Cys Lys Gly
                260                 265                 270

Pro Gly Leu Pro Leu Arg
            275

<210> SEQ ID NO 10
<211> LENGTH: 278
<212> TYPE: PRT
<213> ORGANISM: Penicillium camemberti

<400> SEQUENCE: 10

Asp Val Ser Thr Ser Glu Leu Asp Gln Phe Glu Phe Trp Val Gln Tyr
1               5                   10                  15

Ala Ala Ala Ser Tyr Glu Ala Asp Tyr Thr Ala Gln Val Gly Asp
                20                  25                  30

Lys Leu Ser Cys Ser Lys Gly Asn Cys Pro Glu Val Glu Ala Thr Gly
            35                  40                  45

Ala Thr Val Ser Tyr Asp Phe Ser Asp Ser Thr Ile Thr Asp Thr Ala
        50                  55                  60

Gly Tyr Ile Ala Val Asp His Thr Asn Ser Ala Val Val Leu Ala Phe
65                  70                  75                  80

Arg Gly Ser Tyr Ser Val Arg Asn Trp Val Ala Asp Ala Thr Phe Val
                85                  90                  95

His Thr Asn Pro Gly Leu Cys Asp Gly Cys Leu Ala Glu Leu Gly Phe
            100                 105                 110

Trp Ser Ser Trp Lys Leu Val Arg Asp Asp Ile Ile Lys Glu Leu Lys
        115                 120                 125

Glu Val Val Ala Gln Asn Pro Asn Tyr Glu Leu Val Val Gly His
    130                 135                 140

Ser Leu Gly Ala Ala Val Ala Thr Leu Ala Ala Thr Asp Leu Arg Gly
145                 150                 155                 160

Lys Gly Tyr Pro Ser Ala Lys Leu Tyr Ala Tyr Ala Ser Pro Arg Val
                165                 170                 175

Gly Asn Ala Ala Leu Ala Lys Tyr Ile Thr Ala Gln Gly Asn Asn Phe
            180                 185                 190

Arg Phe Thr His Thr Asn Asp Pro Val Pro Lys Leu Pro Leu Leu Ser
        195                 200                 205

Met Gly Tyr Val His Val Ser Pro Glu Tyr Trp Ile Thr Ser Pro Asn
    210                 215                 220

Asn Ala Thr Val Ser Thr Ser Asp Ile Lys Val Ile Asp Gly Asp Val
225                 230                 235                 240

Ser Phe Asp Gly Asn Thr Gly Thr Gly Leu Pro Leu Leu Thr Asp Phe
                245                 250                 255

Glu Ala His Ile Trp Tyr Phe Val Gln Val Asp Ala Gly Lys Gly Pro
            260                 265                 270

Gly Leu Pro Phe Lys Arg
        275
```

<210> SEQ ID NO 11
<211> LENGTH: 270
<212> TYPE: PRT
<213> ORGANISM: Aspergillus foetidus

<400> SEQUENCE: 11

Ser Val Ser Thr Ser Thr Leu Asp Glu Leu Gln Leu Phe Ala Gln Trp
1               5                   10                  15

Ser Ala Ala Tyr Cys Ser Asn Asn Ile Asp Ser Lys Asp Ser Asn
            20                  25                  30

Leu Thr Cys Thr Ala Asn Ala Cys Pro Ser Val Glu Glu Ala Ser Thr
        35                  40                  45

Thr Met Leu Leu Glu Phe Asp Leu Thr Asn Asp Phe Gly Gly Thr Ala
    50                  55                  60

Gly Phe Leu Ala Ala Asp Asn Thr Asn Lys Arg Leu Val Val Ala Phe
65                  70                  75                  80

Arg Gly Ser Ser Thr Ile Glu Asn Trp Ile Ala Asn Leu Asp Phe Ile
                85                  90                  95

Leu Glu Asp Asn Asp Asp Leu Cys Thr Gly Cys Lys Val His Thr Gly
            100                 105                 110

Phe Trp Lys Ala Trp Glu Ser Ala Ala Asp Glu Leu Thr Ser Lys Ile
        115                 120                 125

Lys Ser Ala Met Ser Thr Tyr Ser Gly Tyr Thr Leu Tyr Phe Thr Gly
    130                 135                 140

His Ser Leu Gly Gly Ala Leu Ala Thr Leu Gly Ala Thr Val Leu Arg
145                 150                 155                 160

Asn Asp Gly Tyr Ser Val Glu Leu Tyr Thr Tyr Gly Cys Pro Arg Ile
                165                 170                 175

Gly Asn Tyr Ala Leu Ala Glu His Ile Thr Ser Gln Gly Ser Gly Ala
            180                 185                 190

Asn Phe Arg Val Thr His Leu Asn Asp Ile Val Pro Arg Val Pro Pro
        195                 200                 205

Met Asp Phe Gly Phe Ser Gln Pro Ser Pro Glu Tyr Trp Ile Thr Ser
    210                 215                 220

Gly Asn Gly Ala Ser Val Thr Ala Ser Asp Ile Glu Val Ile Glu Gly
225                 230                 235                 240

Ile Asn Ser Thr Ala Gly Asn Ala Gly Glu Ala Thr Val Ser Val Leu
                245                 250                 255

Ala His Leu Trp Tyr Phe Phe Ala Ile Ser Glu Cys Leu Leu
            260                 265                 270

<210> SEQ ID NO 12
<211> LENGTH: 270
<212> TYPE: PRT
<213> ORGANISM: Aspergillus niger

<400> SEQUENCE: 12

Ser Val Ser Thr Ser Thr Leu Asp Glu Leu Gln Leu Phe Ser Gln Trp
1               5                   10                  15

Ser Ala Ala Tyr Cys Ser Asn Asn Ile Asp Ser Asp Asp Ser Asn
            20                  25                  30

Val Thr Cys Thr Ala Asp Ala Cys Pro Ser Val Glu Glu Ala Ser Thr
        35                  40                  45

Lys Met Leu Leu Glu Phe Asp Leu Thr Asn Asn Phe Gly Gly Thr Ala
    50                  55                  60

```
Gly Phe Leu Ala Ala Asp Asn Thr Asn Lys Arg Leu Val Val Ala Phe
 65                  70                  75                  80

Arg Gly Ser Ser Thr Ile Lys Asn Trp Ile Ala Asp Leu Asp Phe Ile
                 85                  90                  95

Leu Gln Asp Asn Asp Asp Leu Cys Thr Gly Cys Lys Val His Thr Gly
            100                 105                 110

Phe Trp Lys Ala Trp Glu Ala Ala Asp Asn Leu Thr Ser Lys Ile
        115                 120                 125

Lys Ser Ala Met Ser Thr Tyr Ser Gly Tyr Thr Leu Tyr Phe Thr Gly
    130                 135                 140

His Ser Leu Gly Gly Ala Leu Ala Thr Leu Gly Ala Thr Val Leu Arg
145                 150                 155                 160

Asn Asp Gly Tyr Ser Val Glu Leu Tyr Thr Tyr Gly Cys Pro Arg Val
                165                 170                 175

Gly Asn Tyr Ala Leu Ala Glu His Ile Thr Ser Gln Gly Ser Gly Ala
            180                 185                 190

Asn Phe Pro Val Thr His Leu Asn Asp Ile Val Pro Arg Val Pro Pro
        195                 200                 205

Met Asp Phe Gly Phe Ser Gln Pro Ser Pro Glu Tyr Trp Ile Thr Ser
    210                 215                 220

Gly Thr Gly Ala Ser Val Thr Ala Ser Asp Ile Glu Leu Ile Glu Gly
225                 230                 235                 240

Ile Asn Ser Thr Ala Gly Asn Ala Gly Glu Ala Thr Val Asp Val Leu
                245                 250                 255

Ala His Leu Trp Tyr Phe Phe Ala Ile Ser Glu Cys Leu Leu
            260                 265                 270

<210> SEQ ID NO 13
<211> LENGTH: 269
<212> TYPE: PRT
<213> ORGANISM: Aspergillus oryzae

<400> SEQUENCE: 13

Asp Val Ser Ser Leu Leu Asn Asn Leu Asp Leu Phe Ala Gln Tyr
 1               5                  10                  15

Ser Ala Ala Ala Tyr Cys Asp Glu Asn Leu Asn Ser Thr Gly Thr Lys
                 20                  25                  30

Leu Thr Cys Ser Val Gly Asn Cys Pro Leu Val Glu Ala Ala Ser Thr
            35                  40                  45

Gln Ser Leu Asp Glu Phe Asn Glu Ser Ser Tyr Gly Asn Pro Ala
        50                  55                  60

Gly Tyr Leu Ala Ala Asp Glu Thr Asn Lys Leu Leu Val Leu Ser Phe
 65                  70                  75                  80

Arg Gly Ser Ala Asp Leu Ala Asn Trp Val Ala Asn Leu Asn Phe Gly
                 85                  90                  95

Leu Glu Asp Ala Ser Asp Leu Cys Ser Gly Cys Glu Val His Ser Gly
            100                 105                 110

Phe Trp Lys Ala Trp Ser Glu Ile Ala Asp Thr Ile Thr Ser Lys Val
        115                 120                 125

Glu Ser Ala Leu Ser Asp His Ser Asp Tyr Ser Leu Val Leu Thr Gly
    130                 135                 140

His Ser Tyr Gly Ala Ala Leu Ala Ala Leu Ala Ala Thr Ala Leu Arg
145                 150                 155                 160

Asn Ser Gly His Ser Val Glu Leu Tyr Asn Tyr Gly Gln Pro Arg Leu
                165                 170                 175
```

```
Gly Asn Glu Ala Leu Ala Thr Tyr Ile Thr Asp Gln Asn Lys Gly Gly
                180                 185                 190

Asn Tyr Arg Val Thr His Thr Asn Asp Ile Val Pro Lys Leu Pro Pro
            195                 200                 205

Thr Leu Leu Gly Tyr His His Phe Ser Pro Glu Tyr Tyr Ile Ser Ser
    210                 215                 220

Ala Asp Glu Ala Thr Val Thr Thr Asp Val Thr Glu Val Thr Gly
225                 230                 235                 240

Ile Asp Ala Thr Gly Gly Asn Asp Gly Thr Asp Gly Thr Ser Ile Asp
                245                 250                 255

Ala His Arg Trp Tyr Phe Ile Tyr Ile Ser Glu Cys Ser
                260                 265

<210> SEQ ID NO 14
<211> LENGTH: 269
<212> TYPE: PRT
<213> ORGANISM: Thermomyces lanuginosus

<400> SEQUENCE: 14

Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Asp Ala Pro Ala Gly Thr
                20                  25                  30

Asn Ile Thr Cys Thr Gly Asn Ala Cys Pro Glu Val Glu Lys Ala Asp
            35                  40                  45

Ala Thr Phe Leu Tyr Ser Phe Glu Asp Ser Gly Val Gly Asp Val Thr
50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Asp
                85                  90                  95

Leu Lys Glu Ile Asn Asp Ile Cys Ser Gly Cys Arg Gly His Asp Gly
                100                 105                 110

Phe Thr Ser Ser Trp Arg Ser Val Ala Asp Thr Leu Arg Gln Lys Val
            115                 120                 125

Glu Asp Ala Val Arg Glu His Pro Asp Tyr Arg Val Val Phe Thr Gly
130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
    195                 200                 205

Arg Glu Phe Gly Tyr Ser His Ser Ser Pro Glu Tyr Trp Ile Lys Ser
    210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
                260                 265
```

```
<210> SEQ ID NO 15
<211> LENGTH: 10
<212> TYPE: PRT
<213> ORGANISM: Artificial sequence
<220> FEATURE:
<223> OTHER INFORMATION: Synthetic construct

<400> SEQUENCE: 15

Tyr Arg Ser Ala Glu Ser Val Asp Lys Arg
1               5                   10

<210> SEQ ID NO 16
<211> LENGTH: 40
<212> TYPE: PRT
<213> ORGANISM: Artificial sequence
<220> FEATURE:
<223> OTHER INFORMATION: Variant

<400> SEQUENCE: 16

Tyr Arg Ser Ala Glu Ser Val Asp Lys Ala Ala Thr Met Thr Asp Ala
1               5                   10                  15

Glu Leu Glu Lys Lys Leu Asn Ser Tyr Val Gln Met Asp Lys Glu Tyr
            20                  25                  30

Val Lys Asn Asn Gln Ala Arg Ser
        35                  40

<210> SEQ ID NO 17
<211> LENGTH: 8
<212> TYPE: PRT
<213> ORGANISM: Artificial sequence
<220> FEATURE:
<223> OTHER INFORMATION: Variant

<400> SEQUENCE: 17

Ser Pro Pro Cys Gly Arg Arg Pro
1               5
```

LIPOLYTIC ENZYMES

CROSS-REFERENCE TO RELATED APPLICATIONS

This application is a continuation of U.S. application Ser. No. 10/495,597 filed on May 14, 2004 (now abandoned), which claims priority of 35 U.S.C. 371 national application of PCT/DK03/00028 filed Jan. 16, 2003, which claims priority or the benefit under 35 U.S.C. 119 of Danish application no. PA 2002 00074 filed Jan. 16, 2002 and U.S. provisional application No. 60/353,557 filed Feb. 4, 2002, the contents of which are fully incorporated herein by reference.

FIELD OF THE INVENTION

The present invention relates to a lipolytic enzyme variant and a method of producing such a variant. More particularly, the variant has a relatively high activity for one ester bond in an amphiphilic substrate with two lipophilic groups and a relatively low activity for the ester bond in an amphiphilic substrate with one lipophilic group, e.g. a relatively high phospholipase activity and a relatively low lysophospholipase activity.

BACKGROUND OF THE INVENTION

EP 870840, JP-A 10-42884, JP-A 4-135456 or JP-A 2-49593 describe the use of a phospholipase to hydrolyze a phospholipid to produce lysophospholipid.

U.S. Pat. No. 4,567,046, WO 94/04035, EP 109244, EP 585988, WO 98/26057, WO 98/45453, WO 99/53769, WO 00/32758, WO 0139602 and EP 575133 describe the addition of various lipolytic enzymes to dough in the preparation of baked products and the preparation of lipolytic enzyme variants.

WO 00/32758 discloses that the substrate specificity of a lipolytic enzyme can be modified by making alterations to the amino acid sequence.

SUMMARY OF THE INVENTION

The inventors have developed a method using protein engineering to produce lipolytic enzymes having a relatively high activity for one ester bond in an amphiphilic substrate with two lipophilic groups and a relatively low activity for the ester bond in an amphiphilic substrate with one lipophilic group, e.g. a relatively high phospholipase activity and a relatively low lysophospholipase activity.

Accordingly, the invention provides a method of producing a lipolytic enzyme variant comprising:
a) selecting a parent fungal lipolytic enzyme,
b) in the parent lipolytic enzyme altering at least one specified amino acid residue,
c) optionally, altering one or more amino acid residues other than b),
d) preparing the variant resulting from steps a)-c),
e) testing hydrolytic activities of the variant towards a first substrate and a second substrate,
f) selecting a variant having a ratio of hydrolytic activities towards the first substrate and the second substrate which is lower than the parent lipolytic enzyme, and
g) producing the selected variant.

The first substrate is a molecule comprising one fatty acyl group linked through an ester or thioester bond to a hydrophilic group. The second substrate is a molecule comprising a first lipophilic group which is a fatty acyl group linked through an ester or thioester bond to a hydrophilic group, and a second lipophilic group linked to the hydrophilic group, where the second lipolhilic group may be a second fatty acyl group linked through an ester, thioester or amide bond, or it may be a fatty alcohol linked through an ether or thioether bond.

Each amino acid alteration may be an amino acid substitution, deletion or insertion. The amino acid residue to be altered may be determined from a three-dimensional model of a phospholipid docked with the parent lipolytic enzyme as a residue which comprises an atom (excluding H atoms) which lies within 10 Å (particularly 7 Å or 5 Å) of an atom (excluding H atoms) of the lyso-phospholipid, or it may be the C-terminal amino acid.

Alternatively, the amino acid residue to be altered may be determined by aligning the amino acid sequence of the parent lipolytic enzyme with the T. lanuginosus lipase and selecting a residue corresponding to any of residues 17-18, 20-23, 26, 37, 39, 62, 64, 80-96, 110-113, 144-151, 171-177, 200-211, 213, 215, 227, 253-261 or 263-269.

The invention also provides a 1. lipolytic enzyme having an amino acid sequence derived from the T. lanuginosus lipase (SEQ ID NO: 14) comprising the following amino acid alterations:
a) R84W+G91A+D96F+E99K+G263Q+L264A+I265T+G266D+T267A+L269N,
b) G91A+D96W+E99K+L227G+G263Q+L264A+I265T+G266D+T267A+L269N,
c) R84W+G91A:D96F+E99K+G263Q+L264A+I265T+G266S+T267A+L269N+270A+271G+272G+273F+274S,
d) SPPCGRRP(-E) (SEQ ID NO: 17)+Y21K+E99N+N101S+E239C+Q249R,
e) G91A+D96K+E99K+G263Q+L264A+I265T+G266D+T267A+L269N,
f) Y21V+R84G+G91A:D96F+E99K+G263Q+L264A+I265T+G266D+T267A+L269N+270A+271G+272G+273F+274S,
g) V60G+D62W+R84W+G91A+D96F+E99K+G263Q+L264A+I265T+G266D+T267A+L269N,
h) V60A+D62S+G91A+D96W+E99K+W221R+G263Q+L264A+I265T+G266D+T267A+L269N+270A+271G+272G+273F+274S,
i) R84A+S85D+E87A+G91A+D96G+K98E+E99D,
j) G91A+D96W+E99K+P250N+G263Q+L264A+I265T+G266D+T267A+L269N+270A+271G+272G+273F+274S,
k) G91A+D96W+E99K+P256N+G263Q+L264A+I265T+G266D+T267A+L269N+270A+271G+272G+273F+274S,
l) R84W+G91A+D96W+E99K+Y261Q+G263Q+L264A+I265T+G266D+T267A+L269N+270A+271G+272G+273F+274S,
m) G91A+D96W+E99K+P250L+P253Q+D254DEL+P257S+G263Q+L264A+I265T+G266D+T267A+L269N+270A+271G+272G+273F+274S,
n) R84Y+G91A+D96F+E99K+G263Q+L264A+I265T+G266D+T267A+L269N, or
o) R84S+G91A+D96F+E99K+E129A+V203i+L206F+G263Q+L264A+I265T+G266D+T267A+L269N.

The invention also provides a lipolytic enzyme having an amino acid sequence derived from a Fusarium lipase comprising at least one amino acid alteration corresponding to the following in the Fusarium oxysporum lipase (phospholipase (SEQ ID NO: 7):
a) H257W,
b) S142A, c) V157D,
d) S271P,
e) S80T,
f) A127T,
g) D263G,
h) Y21W,
i) S80T,
j) R274A,
k) 275YRSAESVDKR (SEQ ID NO:15) or
l) 275YRSAESVDKAATMTDAELEKKLNSYVQM-DKEYVKNNQARS (SEQ ID NO:16).

Further, the invention provides a lipolytic enzyme which:
a) has an amino acid sequence having at least 90% identity to that of the *Thermomyces lanuginosus* lipase or the *Fusarium oxysporum* lipase/phospholipase,
b) has phospholipase activity, and
c) has a lysophospholipase to phospholipase ratio below the limit indicated below.

BRIEF DESCRIPTION OF THE DRAWINGS

FIG. 1 gives the coordinates of a three-dimensional model of the *T. lanuginosus* lipase (SEQ ID NO: 14) docked with a phospholipid as substrate: 1-palmetoyl-2-oleylglycero-sn-3-phosphocholine (POPC).

FIG. 2 shows an alignment of the amino acid sequences of the above fungal lipolytic enzymes, based on a comparison of the available 3-dimensional structures, wherein the following amino acid sequences are aligned:
SEQ ID NO: 1: *Absidia reflexa*
SEQ ID NO: 2: *Absidia corymbefera*
SEQ ID NO: 3: *Rhizmucor miehei*
SEQ ID NO: 4: *Rhizopus delemar* (*oryzae*)
SEQ ID NO: 5: *Aspergillus niger*
SEQ ID NO: 6: *Aspergillus tubingensis*
SEQ ID NO: 7: *Fusarium oxysporum*
SEQ ID NO: 8: *Fusarium heterosporum*
SEQ ID NO: 9: *Aspergillus oryzae*
SEQ ID NO: 10: *Penicilium camembertii*
SEQ ID NO: 11: *Aspergillus foetidus*
SEQ ID NO: 12: *Aspergillus niger*
SEQ ID NO: 13: *Aspergillus oryzae*
SEQ ID NO: 14: *Thermomyces lanuginosus* (*Humicola lanuginosa*).

DETAILED DESCRIPTION OF THE INVENTION

Test Substrates

The invention uses two different polar lipids as test substrates. Both are amphiphilic (amphipolaric), having a hydrophilic part and one or two lipophilic groups, respectively.

First Substrate

The first substrate has the general formula A-B—C where:
A is an acyl group, particularly straight-chain and unsubstituted. It may be saturated or may have one or more double bonds. It may have an even number of carbon atoms, e.g. from 12 to 24
B is O (oxygen) or S (sulfur) forming an ester or thioester bond between A and C.
C is a polyol having B attached to an OH group, optionally having other functional groups and/or a hydrophilic group attached to an OH group. The polyol may be a sugar alcohol such as glycerol, e.g. having B attached in the sn1 or sn2 position of glycerol. The other functional groups may be one or more aldehyde, keto or carboxyl groups; thus, the polyol may be a monosaccharide or a corresponding uronic acid. The hydrophilic group linked to an OH group, e.g. in the sn3 position of glycerol, may be:
A phosphate group, optionally linked to an alcohol such as choline, ethanolamine, serine or inositol.
Mono- or digalactosyl link to C through a glycosidic bond.

The first substrate may be a lysophospholipid such as lysolecithin or a lysogalactolipid such as digalactosyl monoglyceride (DGMG) or monogalactosyl monoglyceride (MGMG). The lyso-phospholipid may be a 1-lyso-phospholipid with an acyl group at the sn1-position or a 2-lyso-phospholipid with an acyl group at the sn2-position.

The activity of interest is a hydrolytic activity towards the bond B—C.

Second Substrate

The second substrate has the general formula A'-B'-(A"-B"—)C where:
A' is an acyl group defined as for A above.
B' is O (oxygen) or S (sulfur) forming an ester or thioester bond between A' and C.
A" is an acyl or alkyl group particularly straight-chain and unsubstituted. It may be saturated or may have one or more double bonds. It may have an even number of carbon atoms, e.g. from 12 to 24
B" is O (oxygen), S (sulfur) or NH forming an ester, thioester, amide, ether or thioether bond between A" and C.
C is the same as for the first substrate.

A" and B" of the second substrate may be chosen identical to A and B of the second substrate and attached in the same position of C, or they may be chosen independently.

The second substrate may be a phospholipid such as lecithin or a galactolipid such as digalactosyl diglyceride (DGDG) or monogalactosyl diglyceride (MGDG), or it may be prepared synthetically by attaching a fatty alcohol through an ether bond or thioether bond to a lysophospholipid or a lyso-galactolipid.

The activity of interest is a hydrolytic activity towards the B'—C bond.

Lipolytic Enzyme Activities

The lipolytic enzyme of the invention has a low ratio of activity for the first substrate compared to activity for the second substrate. Thus, it has a relatively low hydrolytic activity towards the B—C (thio)ester bond of the first substrate and a relatively high hydrolytic activity towards the B'—C (thio)ester bond of the second substrate. The activity towards the second substrate may be phospholipase A1 (EC 3.1.1.32) or A2 (EC 3.1.1.4), or it may be a galactolipase activity.

The activity ratio may be found by contacting the lipolytic enzyme with each substrate separately or by contacting it with a mixture including both substrates. The activity ratio may be measured by the PLARN assay, the RLPLA assay or a plate assay described below. The lipolytic enzyme may have a ratio of lysophospholipase activity to phospholipase activity corresponding to PLARN below 1000 (particularly 500, below 200 or below 50) or RLPLA (0.1/2.5) below 2 (particularly below 1 or below 0.5).

The lipolytic enzyme of the invention may have phospholipase (PL) activity with a relatively low lysophospholipase (LPL) activity. The lyso-phospholipid may be a 1-lyso-phospholipid with an acyl group at the sn1-position or a 2-lyso-phospholipid with an acyl group at the sn2-position. The lipolytic enzyme may in particular have phospholipase A1 activity with low 1-lysophospholipase activity.

The lipolytic enzyme of the invention may have hydrolytic activity towards a carboxylic ester bond in DGDG (digalactosyl diglyceride) with a relatively low hydrolytic activity towards the ester bond in DGMG (digalactosyl monoglyceride).

Optionally, the lipolytic enzyme may also have triacylglycerol lipase activity (EC 3.1.1.3), i.e. hydrolytic activity for carboxylic ester bonds in triglycerides, e.g. 1,3-specific activity, particularly on long-chain triglycerides such as olive oil. The enzyme may have a substrate specificity for hydrolyzing long-chain fatty acyl groups rather than short-chain groups, e.g. expressed as a high ratio of activities on olive oil and tributyrin, e.g. a ratio SLU/LU>3 as described in WO 0032758.

LPL/PL Ratio (PLARN)

Phospholipase activity is determined at 30° C. using 4% (w/v) lecithin (phosphatidyl choline) in 50 mM sodium acetate, 5 mM CaCl2, pH 5.0. One unit of phospholipase activity is defined as 1 mmol free fatty acids released per minute per mg enzyme using the above conditions.

Lysophospholipase activity is determined at 30° C. using 1% (w/v) lysolechitin in 50 mM sodium acetate, 5 mM CaCl2, pH 5.0. One unit of lysophospholipase activity is defined as 1 mmol free fatty acids released per minute per mg enzyme using the above conditions. The lysolechitin may be an equilibrium mixture or pure 1-lysolechitin in the case of a phospholipase A1 and pure 2-lysolechitin in the case of a phospholipase A2.

The PLARN ratio is defined as the lysophospholipase activity divided by the phospholipase activity, both determined by the above methods.

Relative Activity on Lyspholipids and Phospholipids (RLPLA)

This activity measurement expresses the relative activity on lysophosphatidyl choline and phosphatidyl choline in an equimolar mixture.

More specifically the assay is carried out as follows: The activity at different concentrations of phospholipase is determined at 30° C. blending 1:1 solutions of phosphatidyl choline (25 mM) and lysophosphatidyl choline (25 mM) in 50 mM NaOAc buffer (pH 5). 50 µl enzyme solution (e.g. having 0.1 or 2.5 mg enzyme protein per ml) is added to the substrate solution and allowed to react for 30 minutes. 100 µl of the sample is inactivated at 95° C. for 5 minutes and dissolved in 900 µl CHCl3/MeOH 50%/50%. The sample is centrifuged at 14000 rpm for 2 minutes. The supernatant is analyzed by HPLC after filtering through a 0.45 µm filter. Column: Microsorb-MV 100Si 250 mm column (analytical instruments). Mobile phases: A: 80% CHCl3, 19.5% MeOH, 0.5% NH4OH; B: 60% CHCl3, 34% MeOH, 0.5% NH4OH, 5.5% H2O. Gradient: 0-3 minutes 100% A, 3-23 minutes 100% B, 23-45 minutes 100% A. Injection volume 20 µl Detector: Sedere, Sedex 75 light scattering, Temp 40° C., pressure 3.5 Bar. The RLPLA is then measured as the depletion of phosphatidyl choline relative to lysophosphatidyl choline. A variant with a lower RLPLA value indicates a higher accumulation of lysophospholipid under the conditions of analysis.

The relative activity can be expressed as "RLPLA ratio" by measuring lysolecithin hydrolysis at an enzyme dosage of 0.1 mg/ml and lecithin hydrolysis at a dosage of 2.5 mg/ml, and taking the ratio of the two.

Plate Assay

Plates including each of the substrates may be prepared in analogy with WO 0032758 using suitable pH and substrate concentration. Optionally, other ingredients such as flour may be included. A suitably diluted enzyme solution is applied to holes in the plates, and clearing zones are read after incubation for a suitable time at a suitable temperature.

Preparation of Lipolytic Enzyme

The lipolytic enzyme may be obtained by preparing variants of a parent lipolytic enzyme by altering its amino acid sequence and screening for a variant with an improved activity ratio. The parent lipolytic enzyme may have phospholipase activity, DGDG hydrolytic activity and/or triacylglycerol lipase activity. Variants may be prepared from the parent lipolytic enzyme by known methods, e.g. by subjecting a DNA sequence encoding the parent lipolytic enzyme to site-directed mutagenesis, localized random mutagenesis or site-saturation mutagenesis, e.g. using methods described in WO 0032758. Resulting DNA sequences may be further modified by gene shuffling and directed evolution.

Parent Lipolytic Enzyme

The lipolytic enzyme to be used in the present invention is one that can hydrolyze ester bonds. Such enzymes include, for example, lipases, such as triacylglycerol lipase (EC 3.1.1.3), lipoprotein lipase (EC 3.1.1.34), monoglyceride lipase (EC 3.1.1.23), phospholipase A1 or A2 (EC 3.1.1.26, 3.1.1.4), lysophospholipase (EC 3.1.1.5), galactolipase (EC 3.1.1.26), ferulic acid esterase and esterase (EC 3.1.1.1, EC 3.1.1.2).

The parent lipolytic enzyme may be the *Thermomyces lanuginosus* lipase (*Humicola lanuginosa* lipase) (EP 305216) or it may have an amino acid sequence with at least 50% identity (e.g. at least 90% identity). The amino acid sequence of the *T. lanuginosus* lipase is shown in U.S. Pat. No. 5,869,438 and as seq14 in FIG. 2 of this application.

Thus, the parent lipolytic enzyme may be a naturally occurring enzyme as described at pages 5-6 of WO 0032758. Examples are the lipolytic enzymes from the following organisms. They are known in the prior art; and their amino acid sequences are given in the attached sequence listing.

1. *Absidia reflexa*
2. *Absidia corymbefera*
3. *Rhizmucor miehei*
4. *Rhizopus delemar* (*oryzae*)
5. *Aspergillus niger*
6. *Aspergillus tubingensis*
7. *Fusarium oxysporum*
8. *Fusarium heterosporum*
9. *Aspergillus oryzae*
10. *Penicilium camembertii*
11. *Aspergillus foetidus*
12. *Aspergillus niger*
13. *Aspergillus oryzae*
14. *Thermomyces lanuginosus* (*Humicola lanuginosa*)

As indicated above, the amino acid to be altered may be determined on the basis of an alignment of the parent lipolytic enzyme with the *T. lanuginosus* lipase. FIG. 2 shows an alignment of the amino acid sequences of the above fungal lipolytic enzymes, based on a comparison of the available 3-dimensional structures:

Other amino acid sequences may be aligned with those shown in FIG. 2 by using the GAP alignment to the most homologous sequence found by the GAP program. GAP is provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443-45). The following settings are used for polypeptide sequence comparison: GAP creation penalty of 3.0 and GAP extension penalty of 0.1.

Alternatively, the parent lipolytic used in the present invention may be a variant of the above, e.g. a variant of the *T.*

*lanuginosus* lipase (SEQ ID NO: 14) or the *F. oxysporum* lipase/phospholipase (SEQ ID NO: 7). A variant with phospholipase activity or galactolipase activity may be used, e.g. as described in Example 5, 6 or 13 of WO 0032758. Particular examples are variants of SEQ ID NO: 14 with the following amino acid alterations:

---

L259S
G266D
G91A + D96W + E99K + G263Q + L264A + I265T + G266D + T267A + L269N + 270A + 271G + 272G + 273F + 274S
G266E
G263A + G266A
E1SPCRPRP + E239C + Q249R + G266A
E1SPCRPRP + E239C + Q249R + G266S
D96S + G266A
D96S + G266S
D96S + G266W
E1SPPCGRRP (SEQ ID NO: 17) + D96S + E239C + Q249R + G263D + L264I + I265N + G266E + T267GS

---

Three-Dimensional Model

FIG. 1 gives the coordinates of a three-dimensional model of the *T. lanuginosus* lipase docked with a phospholipid as substrate: 1-palmetoyl-2-oleylglycero-sn-3-phosphocholine (POPC). This may be used as a starting point for building a similar model for any given fungal lipolytic enzyme. Using this model, the following amino acid residues are found to be within 10 Å, 7 Å and 5 Å of an atom of the substrate (LIP1 in the pdb structure shown in FIG. 1):

10 Å: 17-18, 20-23, 26, 37, 39, 62, 64, 80-96, 110-113, 144-151, 171-177, 200-211, 213, 215, 227, 253-261, 263-269.
7 Å: 21, 81-95, 110, 113, 145-148, 150, 172-175, 201-208, 213, 254-256, 258-259, 264-269.
5 Å: 21, 82-86, 89-90, 92-93, 95, 110, 113, 145-147, 174, 202-203, 206-208, 255, 258-259, 265-268.

More particularly, amino acid alterations may be made at one or more positions corresponding to the following amino acids in the *T. lanuginosus* lipase (SEQ ID NO: 14): Y212, R84, S85, E87, D96, V203, L206, L227, P253, D254, P256, P257 and/or Y261, particularly one or more alterations corresponding to Y21V/K, R84W/A/G/Y/S, S85D, E87A, D96F/K/G, V203I, L206F, P253Q, D254*, P256N, P257S and/or Y261Q.

Further, amino acid alterations may be made at one or more positions corresponding to H257, S142, S80, D263 and/or Y21 of the *F. oxysporum* lipase/phospholipase (SEQ ID NO: 7), particularly one or more corresponding to H257W, S142A, S80T, D263G and/or Y21W.

Also, amino acid alterations may be made at the C-terminal or at any position down-stream of L269 of SEQ ID NO: 14. Such alteration may be addition or deletion of a peptide extension or deletion of a peptide extension of one or more amino acids (e.g. 1-50 amino acids such as 2-15) at the C-terminal.

Amino Acid Alteration

The amino acid alteration may be substitution with a larger amino acid. The amino acid residues are ranked by size as follows from smallest to largest:

G, A, S, C, V, T, P, L, I, N, D, M, E, Q, K, H, R, F, Y, W

An amino acid residue within 10 Å (or 7 Å or 5 Å) of a C atom in the alkyl group R of R—COO attached to sn1 of the lyso-phospholipid may be substituted with an amino acid residue which is larger or more hydrophilic.

An amino acid residue within 10 Å (or 7 Å or 5 Å) of an atom (other than H) of the phosphate group attached to sn3 (i.e. the O atom at sn3 or any atom beyond that) may be substituted with an amino acid which is larger or more hydrophobic.

Amino acid residues are ranked as follows from most hydrophilic to most hydrophobic:

R, K, E, D, N, Q, H, S, T, Y, C, M, G, A, V, P, L, I, F, W

Lipolytic Enzyme Variant

Starting from a variant having phospholipase activity derived from the *T. lanuginosus* lipase, and improvement regarding increased ratio of lecithin/lysolecithin (sn1) activity and lowered activity against lysolecithin (sn1) of lysolecithin in general, or/and with improved sn1 lecithase activity may be achieved by use of the following concepts.

One concept is to lower the binding energy of sn1 acyl chain and in this way increase the ratio of activity lecithin/lysolecithin (sn1). Secondary to increase sn2 binding to favour lecithin rather than lysolecithin.

Thus, 206, 95, 203 and 93 may be made smaller and more hydrophilic. Also, positions 253, 255 and 256 may be made bigger. Some particular examples of such variants are:

L206V/S/T/A
V203T/S/A
F95I/L/Y
L93V/I/A/T

A doped library 206/203 and 95/93. appr. 90% wt and appr 10% variant may be used.

A second concept is to make libraries in the contacts to both acyl chains found docked structures, and in the regions close to the substrate found by comparison of good and bad lysolecithase active homologous enzymes. The regions will be doped according to the homologous enzymes sequence.

Thus, region 265-269 is of interest, e.g. P253. Some particular examples of such variants are:

A doped library 247-260 may be used, optionally together with doped I202P and L206V. The doping may be appr. 90% wt and appr. 10% variants.

P253TG/L
D254S/L
I255
P256L/A
A257D/A
L259
W260H
Proline removal(s):
P256X
P253X
together with I202P
L227D Library 247-260 and 206, 95, 203 and 93 may be combined.

Amino Acid Identity

The lipolytic enzyme of the invention and the parent lipolytic enzyme may have an amino acid identity of at least 50% (particularly at least 90%, e.g. more than 95% or more than 98%) with the *T. lanuginosus* lipase (SEQ ID NO: 14).

The degree of identity may be suitably determined by means of computer programs known in the art, such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443-45), using GAP with the following settings for polypeptide sequence comparison: GAP creation penalty of 3.0 and GAP extension penalty of 0.1.

Use of Lipolytic Enzyme Variant
Hydrolysis of Phospholipid

A variant with phospholipase activity can be used to prepare lysophospholipid (e.g. lyso-lecithin) by treating the corresponding phospholipid with the variant, e.g. as described in EP 870840, JP-A 10-42884, JP-A 4-135456 or JP-A 2-49593. The variant can also be used to make mayonnaise, e.g. as described in EP 628256, EP 398666 or EP 319064.

Advantageously, a low ratio of lysophospholipase/phospholipase activity can lead to a high degree of phospholipid hydrolysis with a low degree of lysophospholipid hydrolysis. This may allow the use of long reaction time and the use of phospholipid with a high lysophospholipid content, e.g. from cereals such as oats.

Baking

Lipolytic enzymes according to the invention have improved baking performance, e.g. a lower dough stickiness, a better dough extensibility and elasticity, a better dough stability, a better crumb structure of the baked product, a larger loaf volume and/or improved resistance to over-proofing or other abuse.

The invention provides a baking additive in the form of a granulate, an agglomerated powder or a stabilized liquid, comprising a lipolytic enzyme which:
  a) has phospholipase activity, and
  b) has a lysophospholipase to phospholipase ratio corresponding to PLARN below 500 or RLPLA (0.1/2,5). below 1.0.

The baking additive may have a narrow particle size distribution with more than 95% (by weight) of the particles in the range from 25 to 500 p.m.

Granulates and agglomerated powders may be prepared by conventional methods, e.g. by spraying the lipolytic enzyme onto a carrier in a fluid-bed granulator. The carrier may consist of particulate cores having a suitable particle size. The carrier may be soluble or insoluble, e.g. a salt (such as NaCl or sodium sulfate), a sugar (such as sucrose or lactose), a sugar alcohol (such as sorbitol), starch, rice, corn grits, or soy. Liquid enzyme preparations may, for instance, be stabilized by adding a polyol such as propylene glycol, a sugar or sugar alcohol, lactic acid or boric acid according to established methods.

The invention further relates to a pre-mix comprising flour and the lipolytic enzyme described above. The pre-mix may contain other dough-improving and/or bread-improving additives, e.g. any of the additives, including enzymes, mentioned above.

The invention also provides a method of preparing a dough or a baked product prepared from dough. The method may comprise preparing a variant by the above method and adding it to the dough. Alternatively, the method may comprise:
  a) testing at least one lipolytic enzyme for its hydrolytic activities towards intact phospholipid (PL) and lysophospholipid (LPL),
  b) selecting a lipolytic enzyme having a hydrolytic activity ratio for LPL/PL corresponding to PLARN below 500, and
  c) adding the selected lipolytic enzyme to the dough.

Dough

The dough generally comprises wheat meal or wheat flour and/or other types of meal, flour or starch such as corn flour, corn starch, rye meal, rye flour, oat flour, oat meal, soy flour, sorghum meal, sorghum flour, rice starch, rice flour, potato meal, potato flour or potato starch. The dough may be fresh, frozen or par-baked. It may particularly be a leavened dough.

The dough may also comprise other conventional dough ingredients, e.g.: proteins, such as milk powder, gluten, and soy; eggs (either whole eggs, egg yolks or egg whites); an oxidant such as ascorbic acid, potassium bromate, potassium iodate, azodicarbonamide (ADA) or ammonium persulfate; an amino acid such as L-cysteine; a sugar; a salt such as sodium chloride, calcium acetate, sodium sulfate or calcium sulfate.

The dough may comprise fat (triglyceride) such as granulated fat or shortening, but the invention is particularly applicable to a dough where less than 1% by weight of fat (triglyceride) is added, and particularly to a dough which is made without addition of fat.

The dough may further comprise an emulsifier such as mono- or diglycerides, diacetyl tartaric acid esters of mono- or diglycerides, sugar esters of fatty acids, polyglycerol esters of fatty acids, lactic acid esters of monoglycerides, acetic acid esters of monoglycerides, polyoxyethylene stearates, or lysolecithin, but the invention is particularly applicable to a dough which is made without addition of emulsifiers (other than optionally phospholipid).

Baked Product

The process of the invention may be used for any kind of baked product prepared from dough, either of a soft or a crisp character, either of a white, light or dark type. Examples are bread (in particular white, whole-meal or rye bread), typically in the form of loaves or rolls, French baguette-type bread, pita bread, tortillas, cakes, pancakes, biscuits, cookies, muffins, pie crusts, crisp bread, steamed bread, pizza and the like.

Additional Enzyme

Optionally, an additional enzyme may be used together with the lipolytic enzyme. The additional enzyme may be a second lipolytic enzyme (e.g. as described in PCT/DK01/00472), an amylase, particularly an anti-staling amylase, an amyloglucosidase, a cyclodextrin glucanotransferase, or the additional enzyme may be a peptidase, in particular an exopeptidase, a transglutaminase, a cellulase, a hemicellulase, in particular a pentosanase such as xylanase, a protease, a protein disulfide isomerase, e.g., a protein disulfide isomerase as disclosed in WO 95/00636, a glycosyltransferase, a branching enzyme (1,4-α-glucan branching enzyme), a 4-α-glucanotransferase (dextrin glycosyltransferase), a lactase (galactosidase), or an oxidoreductase, e.g., a peroxidase, a laccase, a glucose oxidase, a pyranose oxidase, a lipoxygenase, an L-amino acid oxidase or a carbohydrate oxidase.

The amylase may be a fungal or bacterial alpha-amylase, e.g. from *Bacillus*, particularly *B. licheniformis* or *B. amyloliquefaciens*, or from *Aspergillus*, particularly *A. oryzae*, a beta-amylase, e.g. from plant (e.g. soy bean) or from microbial sources (e.g. *Bacillus*). The amylase may be an anti-staling amylase, as described in WO 99/53769, i.e. an amylase that is effective in retarding the staling (crumb firming) of baked products, particularly a maltogenic alpha-amylase, e.g. from *Bacillus stearothermophilus* strain NCIB 11837.

Other Uses

The lipolytic enzyme variant may also be used in the production of pasta and noodles in analogy with EP 1057415.

A lipolytic enzyme variant with phospholipase activity may be used in cheese production as described in WO 00/54601.

EXAMPLES

Example 1

Variants Based on a *T. lanuginosus* Lipase Variant

A prior-art variant of the *T. lanuginosus* lipase with phospholipase activity was chosen as the starting point (parent lipolytic enzyme), and variants were prepared by introducing further amino acid alterations into the prior-art variant.

Experiment A

Activities of the new variants were determined with lecithin and lysolecithin (pure 1-phosphatidyl choline, 1-lysolecithin) as substrates by the methods described above. More specifically, 1.7 mL of the reaction mixture was shaken for between 15 and 90 min in an Eppendorf tube shaken at 1300 rpm by an "Eppendorf Thermomixer comfort". The enzyme was inactivated at 95 C for 5 min, and centrifuged at 14000 rpm by Eppendorf centrifuge 5417R. The liberated fatty acids were determined (relative to a control sample where the enzyme was inactivated before it was added to the substrate) by NEFA C test from Wako following the ACS-ACOD method described for the NEFA-C test.

Three variants were found to have phospholipase activity and a to have a lower ratio of lysophospholipase to phospholipase than the prior-art variant.

R84W+G91A+D96F+E99K+G263Q+L264A+I265T+ G266D+T267A+L269N

G91A+D96W+E99K+L227G+G263Q+L264A+I265T+ G266D+T267A+L269N

R84W+G91A+D96F+E99K+G263Q+L264A+I265T+ G266S+T267A+L269N+270A+271G+272G+273F+ 274S

Experiment B

Activities of further variants were determined with lecithin and lysolecithin (mixture of 1- and 2-lysolecithin) as substrates at 0.1 and 2.5 mg/ml by the RLPLA method described above. All variants were found to have a high activity on lysolecithin compared to lecithin.

Variants having the following amino acid alterations compared to SEQ ID NO: 14 were found to have phospholipase activity and a to have a lower ratio of lysophospholipase to phospholipase than the prior-art variant.

---

SPPCGRRP(-E) (SEQ ID NO: 17) + Y21K + E99N + N101S + E239C + Q249R
G91A + D96K + E99K + G263Q + L264A + I265T + G266D + T267A + L269N
Y21V + R84G + G91A + D96F + E99K + G263Q + L264A + I265T + G266D + T267A + L269N + 270A + 271G + 272G + 273F + 274S
V60G + D62W + R84W + G91A + D96F + E99K + G263Q + L264A + I265T + G266D + T267A + L269N
V60A + D62S + G91A + D96W + E99K + W221R + G263Q + L264A + I265T + G266D + T267A + L269N + 270A + 271G + 272G + 273F + 274S
R84A + S85D + E87A + G91A + D96G + K98E + E99D
G91A + D96W + E99K + P250N + G263Q + L264A + I265T + G266D + T267A + L269N + 270A + 271G + 272G + 273F + 274S
G91A + D96W + E99K + P256N + G263Q + L264A + I265T + G266D + T267A + L269N + 270A + 271G + 272G + 273F + 274S
R84W + G91A + D96W + E99K + Y261Q + G263Q + L264A + I265T + G266D + T267A + L269N + 270A + 271G + 272G + 273F + 274S
G91A + D96W + E99K + P250L + P253Q + D254DEL + P257S + G263Q + L264A + I265T + G266D + T267A + L269N + 270A + 271G + 272G + 273F + 274S
R84Y + G91A + D96F + E99K + G263Q + L264A + I265T + G266D + T267A + L269N
R84S + G91A + D96F + E99K + E129A + V203i + L206F + G263Q + L264A + I265T + G266D + T267A + L269N

---

Example 2

Variants of *F. oxysporum* Lipase/Phospholipase

Variants of the *F. oxysporum* lipase/phospholipase were prepared, having the following amino acid alterations compared to SEQ ID NO: 7:
H257W
S142A
V157D+S271P
S80T+A127T
D263G
Y21W
S80T The following variants with modified C-terminal sequences were prepared by making the substitutions R274A and/or R284A to remove one or two cleavage points for the Kex-2 protease:

R274A+275YRSAESVDKR (SEQ ID NO:15)

R274A+275YRSAESVDKAATMTDAELEKKLN-SYVQMDKEYVKNNQARS (SEQ ID NO:16)

Activities of the variants and the parent enzyme were determined as in Example 2. Compared to the parent enzyme, the variants were found to have lower activity on lysolecithin and a lower ratio of lysolecithin activity to lecithin activity.

Example 3

Preparation of Dough

Doughs were prepared from Meneba flour according to the European straight dough method (ABF-SP 1201.1) with 40 ppm Fungamyl Super MA (Novozymes), 40 ppm ascorbic acid, and different dosages of lipolytic enzyme.

The stickiness of the dough was evaluated an a 1-10 scale by the baker as the degree to which a dough adheres to ones hands or other surfaces, where 5 is identical to a control without addition of lipolytic enzyme, 1 is the lowest degree of stickiness and 10 is the highest degree of stickiness.

The extensibility of the dough was evaluated an a 1-10 scale by the baker as the degree to which a dough can be stretched without tearing, where 5 is identical to a control without addition of lipolytic enzyme, 1 indicates the lowest (shortest) extensibility and 10 indicates the highest (longest) extensibility The elasticity of the dough was evaluated an a 1-10 scale by the baker as the degree to which a dough tends to recover its original shape after release from a deforming force, where 5 is identical to a control without addition of lipolytic enzyme, 1 indicates the lowest (weakest) elasticity and 10 indicates the highest (strongest) elasticity.

A lipolytic enzymes prepared in Example 1 was tested, and the prior-art variant was tested for comparison. The results were as follows Experiment A

| Lipolytic enzyme | Dosage | PLARN ratio | Stickiness | Extensibility | Elasticity |
|---|---|---|---|---|---|
| Invention | 0.2 mg/kg dough | 690 | 5 | 6 | 4 |
| Prior art | 250 LU/kg dough | 5800 | 5 | 7 | 3 |

Experiment B

| Lipolytic enzyme | Dosage | RLPLA ratio | Stickiness | Extensibility | Elasticity |
|---|---|---|---|---|---|
| Invention | 0.2 mg/kg flour | 1.06 | 4 | 4 | 6 |
| Prior art | 250 LU/kg dough | 1.58 | 5 | 5 | 5 |

The results show that lipolytic enzymes with a lower ratio of lysolecithin activity to lecithin activity make doughs with a desirable combination of lower extensibility and higher elasticity than the prior-art lipolytic enzymes, and they furthermore tend to make a less sticky dough.

The invention claimed is:

1. An isolated lipolytic enzyme variant, comprising a polypeptide having at least 90% identity to the amino acid sequence of SEQ ID NO: 14 and comprises an amino acid substitution R84G, R84A, R84Y, R84S, or L206F of SEQ ID NO: 14, and wherein the variant has phospholipase activity and lysophospholipase activity, and has a lysophospholipase to phospholipase activity ratio (PLARN) below 1000, wherein phospholipase activity is determined at 30° C. using 4% (w/v) lecithin (phosphatidyl choline) in 50 mM sodium acetate, 5 mM CaCl$_2$, pH 5.0, and lysophospholipase activity is determined at 30° C. using 1% (w/v) lysolechitin in 50 mM sodium acetate, 5 mM CaCl$_2$, pH 5.0.

2. The lipolytic enzyme variant of claim 1, comprising the following amino acid alterations:
   a) Y21V+R84G+G91A+D96F+E99K+G263Q+L264A+I265T+G266D+T267A+L269N+270A+271G+272G+273F+274S,
   b) R84A+S85D+E87A+G91A+D96G+K98E+E99D,
   c) R84Y+G91A+D96F+E99K+G263Q+L264A+I265T+G266D+T267A+L269N, or
   d) R84S+G91A+D96F+E99K+E129A+V203i+L206F+G263Q+L264A+I265T+G266D+T267A+L269N.

3. The lipolytic enzyme variant of claim 1, further comprising the following amino acid alterations:
   a) R84W+G91A+D96F+E99K+G263Q+L264A+I265T+G266D+T267A+L269N,
   b) G91A+D96W+E99K+L227G+G263Q+L264A+I265T+G266D+T267A+L269N,
   c) R84W+G91A+D96F+E99K+G263Q+L264A+I265T+G266S+T267A+L269N+270A+271 G+272G+273F+274S,
   d) SPPCGRRP(-E)+Y21K+E99N+N101S+E239C+Q249R,
   e) G91A+D96K+E99K+G263Q+L264A+I265T+G266D+T267A+L269N,
   f) V60G+D62W+R84W+G91A+D96F+E99K+G263Q+L264A+I265T+G266D+T267A+L269N,
   g) V60A+D62S+G91A+D96W+E99K+W221R+G263Q+L264A+I265T+G266D+T267A+L269N+270A+271G+272G+273F+274S,
   h) G91A+D96W+E99K+P250N+G263Q+L264A+I265T+G266D+T267A+L269N+270A+271 G+272G+273F+274S,
   i) G91A+D96W+E99K+P256N+G263Q+L264A+I265T+G266D+T267A+L269N+270A+271G+272G+273F+274S,
   j) R84W+G91A+D96W+E99K+Y261Q+G263Q+L264A+I265T+G266D+T267A+L269N+270A+271G+272G+273F+274S, or
   k) G91A+D96W+E99K+P250L+P253Q+D254DEL+P257S+G263Q+L264A+I265T+G266D+T267A+L269N+270A+271G+272G+273F+274S.

4. The lipolytic enzyme variant of claim 1, which comprises an amino acid substitution R84G.

5. The lipolytic enzyme variant of claim 1, which comprises an amino acid substitution R84A.

6. The lipolytic enzyme variant of claim 1, which comprises an amino acid substitution R84Y.

7. The lipolytic enzyme variant of claim 1, which comprises an amino acid substitution R84S.

8. The lipolytic enzyme variant of claim 1, which comprises an amino acid substitution L206F.

9. A composition comprising the lipolytic enzyme variant of claim 1.

10. The composition of claim 9, further comprising a carrier selected from a salt, a sugar, a sugar alcohol, starch, rice, corn grits, or soy.

11. The composition of claim 9, wherein the composition is in the form of a granulate or agglomerated powder.

12. The composition of claim 11, wherein more than 95 weight % of the granulate or agglomerated powder has a particle size between 25 and 500 μm.

* * * * *